(12) United States Patent
Swayze et al.

(10) Patent No.: US 10,835,254 B2
(45) Date of Patent: Nov. 17, 2020

(54) POWERED SURGICAL CIRCULAR STAPLER

(71) Applicant: Ethicon LLC, Guaynabo, PR (US)

(72) Inventors: Jeffrey S. Swayze, West Chester, OH (US); Chester O. Baxter, III, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 59 days.

(21) Appl. No.: 16/156,077

(22) Filed: Oct. 10, 2018

(65) Prior Publication Data

US 2019/0105051 A1 Apr. 11, 2019

Related U.S. Application Data

(63) Continuation of application No. 15/268,684, filed on Sep. 19, 2016, which is a continuation of application
(Continued)

(51) Int. Cl.
*A61B 17/115* (2006.01)
*A61B 90/00* (2016.01)
*A61B 17/00* (2006.01)

(52) U.S. Cl.
CPC ........ *A61B 17/115* (2013.01); *A61B 17/1155* (2013.01); *A61B 2017/00017* (2013.01);
(Continued)

(58) Field of Classification Search
CPC .............. A61B 17/115; A61B 17/1155; A61B 2090/0811; A61B 2017/00017;
(Continued)

(56) References Cited

U.S. PATENT DOCUMENTS 4,805,823 A 2/1989 Rothfuss
4,930,674 A 6/1990 Barak
(Continued)

FOREIGN PATENT DOCUMENTS

CN 202044308 U 11/2011
CN 102940513 A 2/2013
(Continued)

OTHER PUBLICATIONS

Chinese Office Action, The First Office Action and Search Report dated Apr. 1, 2017 for Application No. CN 201380066025.5, 8 pgs.
(Continued)

*Primary Examiner* — Robert F Long
(74) *Attorney, Agent, or Firm* — Frost Brown Todd LLC

(57) ABSTRACT

A surgical instrument includes a stapling head assembly and a first locking feature. The stapling head assembly has a cartridge housing, a staple deck, a plurality of staples, a staple driver, a cylindraceous knife, and a trocar. The cartridge housing extends along a longitudinal axis that is configured to removably couple with a portion of a shaft assembly. The staple driver is configured to translate distally from a proximal driver position toward a distal driver position to thereby drive each of the plurality of staples distally from an annular array of staple pockets, respectively, for forming the plurality of staples in a tissue of a patient. The first locking feature is operatively connected to the cartridge housing and configured to removably couple against the portion of the shaft assembly for selectively coupling and decoupling the stapling head assembly relative to the portion of the shaft assembly.

20 Claims, 43 Drawing Sheets

Related U.S. Application Data

No. 13/716,308, filed on Dec. 17, 2012, now Pat. No. 9,445,816.

(52) U.S. Cl.
CPC ............... *A61B 2017/00115* (2013.01); *A61B 2017/00393* (2013.01); *A61B 2017/00398* (2013.01); *A61B 2017/00734* (2013.01); *A61B 2090/0811* (2016.02)

(58) Field of Classification Search
CPC ........... A61B 2017/00115; A61B 2017/00393; A61B 2017/00398; A61B 2017/00734
USPC ............................................ 227/175.1–182.1
See application file for complete search history.

(56) References Cited

U.S. PATENT DOCUMENTS

| | | |
|---|---|---|
| RE33,362 E | 10/1990 | Mongeon et al. |
| 5,205,459 A | 4/1993 | Brinkerhoff et al. |
| 5,271,543 A | 12/1993 | Grant et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,361,473 A | 11/1994 | Landes |
| 5,389,098 A | 2/1995 | Tsuruta et al. |
| 5,415,334 A | 5/1995 | Williamson, IV et al. |
| 5,417,700 A | 5/1995 | Egan |
| 5,465,895 A | 11/1995 | Knodel et al. |
| 5,533,661 A | 7/1996 | Main et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,711,472 A | 1/1998 | Bryan |
| 5,814,055 A | 9/1998 | Knodel et al. |
| 6,050,472 A | 4/2000 | Shibata |
| 6,159,146 A * | 12/2000 | El Gazayerli ........ A61B 17/068 600/104 |
| 6,258,107 B1 | 7/2001 | Balázs et al. |
| 6,443,973 B1 * | 9/2002 | Whitman ......... A61B 17/07207 606/219 |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,032,798 B2 | 4/2006 | Whitman et al. |
| 7,077,856 B2 * | 7/2006 | Whitman ......... A61B 17/07207 606/219 |
| 7,143,923 B2 | 12/2006 | Shelton, IV et al. |
| 7,252,660 B2 | 8/2007 | Kunz |
| 7,303,106 B2 | 12/2007 | Milliman et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,431,188 B1 * | 10/2008 | Marczyk ............ A61B 17/0686 227/175.1 |
| 7,434,715 B2 | 10/2008 | Shelton, IV et al. |
| 7,434,717 B2 | 10/2008 | Shelton, IV et al. |
| 7,549,563 B2 | 6/2009 | Mather et al. |
| 7,588,176 B2 | 9/2009 | Timm et al. |
| 7,669,746 B2 | 3/2010 | Shelton, IV |
| 7,721,930 B2 | 5/2010 | McKenna et al. |
| 7,731,072 B2 * | 6/2010 | Timm .............. A61B 17/07207 227/175.1 |
| 7,740,159 B2 | 6/2010 | Shelton, IV et al. |
| 7,766,207 B2 | 8/2010 | Mather et al. |
| 7,794,475 B2 | 9/2010 | Hess et al. |
| 7,845,537 B2 * | 12/2010 | Shelton, IV ..... A61B 17/00234 227/180.1 |
| 7,862,502 B2 * | 1/2011 | Pool ........................ A61F 5/003 600/37 |
| 7,918,377 B2 | 4/2011 | Fuchs et al. |
| 7,922,063 B2 | 4/2011 | Zemlok et al. |
| 7,959,050 B2 | 6/2011 | Smith et al. |
| 8,025,199 B2 | 9/2011 | Whitman et al. |
| 8,037,591 B2 | 10/2011 | Spivey et al. |
| 8,066,167 B2 | 11/2011 | Measamer et al. |
| 8,286,846 B2 | 10/2012 | Smith et al. |
| 8,292,150 B2 | 10/2012 | Bryant |
| 8,322,590 B2 | 12/2012 | Patel et al. |
| 8,360,296 B2 | 1/2013 | Zingman |
| 8,573,465 B2 | 11/2013 | Shelton, IV |
| 8,622,275 B2 | 1/2014 | Baxter, III et al. |
| 8,632,462 B2 | 1/2014 | Yoo et al. |
| 8,733,614 B2 | 5/2014 | Ross et al. |
| 8,752,749 B2 | 6/2014 | Moore et al. |
| 8,808,319 B2 | 8/2014 | Houser et al. |
| 8,827,903 B2 | 9/2014 | Shelton, IV et al. |
| 8,899,466 B2 | 12/2014 | Baxter, III et al. |
| 8,925,783 B2 * | 1/2015 | Zemlok .................. G06F 19/00 227/176.1 |
| 8,955,732 B2 | 2/2015 | Zemlok et al. |
| 9,072,536 B2 | 7/2015 | Shelton, IV et al. |
| 9,113,884 B2 | 8/2015 | Shelton, IV et al. |
| 9,289,207 B2 | 3/2016 | Shelton, IV |
| 9,420,967 B2 | 8/2016 | Zand et al. |
| 9,445,816 B2 | 9/2016 | Swayze et al. |
| 9,463,022 B2 | 10/2016 | Swayze et al. |
| 9,498,222 B2 | 11/2016 | Scheib et al. |
| 9,532,783 B2 | 1/2017 | Swayze et al. |
| 9,572,573 B2 | 2/2017 | Scheib et al. |
| 9,597,081 B2 | 3/2017 | Swayze et al. |
| 9,724,100 B2 | 8/2017 | Scheib et al. |
| 9,737,357 B2 | 8/2017 | Dycus et al. |
| 10,105,140 B2 | 10/2018 | Malinouskas et al. |
| 10,117,656 B2 | 11/2018 | Sgroi et al. |
| 10,135,242 B2 | 11/2018 | Baber et al. |
| 10,485,616 B2 * | 11/2019 | Auld ........................ A61B 34/32 |
| 10,548,603 B2 * | 2/2020 | Swayze ............. A61B 17/1155 |
| 2003/0040765 A1 * | 2/2003 | Breznock .......... A61B 17/32053 606/184 |
| 2005/0006434 A1 | 1/2005 | Wales et al. |
| 2005/0154411 A1 * | 7/2005 | Breznock ........ A61B 17/320016 606/184 |
| 2005/0267555 A1 | 12/2005 | Marnfeldt et al. |
| 2007/0021766 A1 * | 1/2007 | Belagali ............. A61B 17/1622 606/180 |
| 2007/0135803 A1 * | 6/2007 | Belson .................... A61B 5/064 606/1 |
| 2007/0179408 A1 | 8/2007 | Soltz |
| 2008/0082124 A1 * | 4/2008 | Hess ..................... A61B 17/064 606/219 |
| 2008/0223903 A1 * | 9/2008 | Marczyk ............... A61B 17/105 227/175.1 |
| 2008/0255413 A1 | 10/2008 | Zemlok et al. |
| 2008/0272172 A1 * | 11/2008 | Zemlok ................ A61B 17/105 227/175.1 |
| 2008/0308607 A1 * | 12/2008 | Timm .............. A61B 17/07207 227/176.1 |
| 2009/0001121 A1 | 1/2009 | Hess et al. |
| 2010/0010512 A1 * | 1/2010 | Taylor ................. A61B 17/0469 606/144 |
| 2010/0012702 A1 * | 1/2010 | Marczyk ........... A61B 17/07207 227/175.1 |
| 2011/0022032 A1 | 1/2011 | Zemlok et al. |
| 2011/0208174 A1 | 8/2011 | Baust et al. |
| 2011/0208236 A1 | 8/2011 | Ward et al. |
| 2011/0257635 A1 | 10/2011 | Whitman et al. |
| 2011/0290855 A1 * | 12/2011 | Moore ............. A61B 17/07207 227/180.1 |
| 2012/0074201 A1 * | 3/2012 | Baxter, III ........ A61B 17/07207 227/180.1 |
| 2012/0089131 A1 | 4/2012 | Zemlok et al. |
| 2012/0104071 A1 | 5/2012 | Bryant |
| 2012/0205421 A1 * | 8/2012 | Shelton, IV ......... A61B 17/068 227/177.1 |
| 2012/0223121 A1 | 9/2012 | Viola et al. |

(56) References Cited

U.S. PATENT DOCUMENTS

| | | |
|---|---|---|
| 2012/0238829 A1 | 9/2012 | Shelton, IV et al. |
| 2013/0090642 A1 | 4/2013 | Shadduck et al. |
| 2013/0098968 A1 | 4/2013 | Aranyi et al. |
| 2013/0102843 A1 | 4/2013 | Feuer et al. |
| 2014/0025046 A1* | 1/2014 | Williams ......... A61B 17/07207 606/1 |
| 2014/0158747 A1 | 6/2014 | Measamer et al. |
| 2015/0076205 A1* | 3/2015 | Zergiebel ....... A61B 17/32001 227/175.1 |
| 2015/0374373 A1 | 12/2015 | Rector et al. |
| 2016/0066911 A1* | 3/2016 | Baber .................... A61B 90/70 307/52 |
| 2017/0000487 A1 | 1/2017 | Swayze et al. |
| 2017/0281184 A1* | 10/2017 | Shelton, IV ......... A61B 17/072 |
| 2017/0281187 A1* | 10/2017 | Shelton, IV ....... A61B 17/3211 |
| 2017/0333035 A1* | 11/2017 | Morgan ................. A61B 34/76 |
| 2018/0125601 A1 | 5/2018 | Cabrera |
| 2018/0168613 A1* | 6/2018 | Shelton, IV ......... A61B 17/072 |

FOREIGN PATENT DOCUMENTS

| | | |
|---|---|---|
| EP | 1 813 211 A2 | 8/2007 |
| EP | 1 982 657 A2 | 10/2008 |
| EP | 2 044 888 A2 | 4/2009 |
| EP | 2 055 243 A2 | 5/2009 |
| JP | 2004-532704 A | 10/2004 |
| JP | 2009106752 A | 5/2009 |
| JP | 2012505046 A | 3/2012 |
| SU | 1225540 A2 | 4/1986 |
| WO | WO 2016/057225 A1 | 4/2016 |

OTHER PUBLICATIONS

European Exam Report dated Jan. 17, 2017 for Application No. EP 13821021.6, 4 pgs.
European Exam Report dated Aug. 28, 2018 for Application No. EP 13821021.6, 3 pgs.
International Search Report and Written Opinion dated Jul. 17, 2014 for Application No. PCT/US2013/075240, 18 pgs.
Japanese Office Action, Notification of Reasons for Refusal, dated Aug. 1, 2017 for Application No. JP 2015-548029, 7 pgs.
Japanese Office Action, Decision to Grant a Patent, dated Jan. 9, 2018 for Application No. JP 2015-548029, 3 pgs.
Brazilian Office Action and Search Report dated Nov. 29, 2019 for Application No. BR112015014002-5, 4 pages.
Mexican Office Action dated Aug. 30, 2018 for Application No. MX/a/2015/007737, 2 pages.
Russian Search Report dated Nov. 17, 2017 for Application No. 2015129029, 2 pages.
Russian Office Action dated Jun. 7, 2018 for Application No. 2015129029, 3 pages.

\* cited by examiner

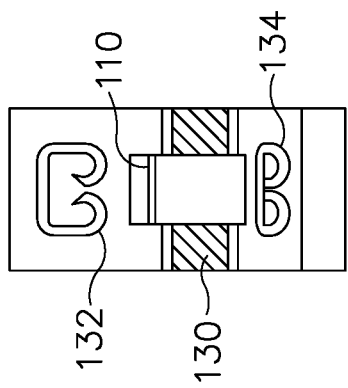
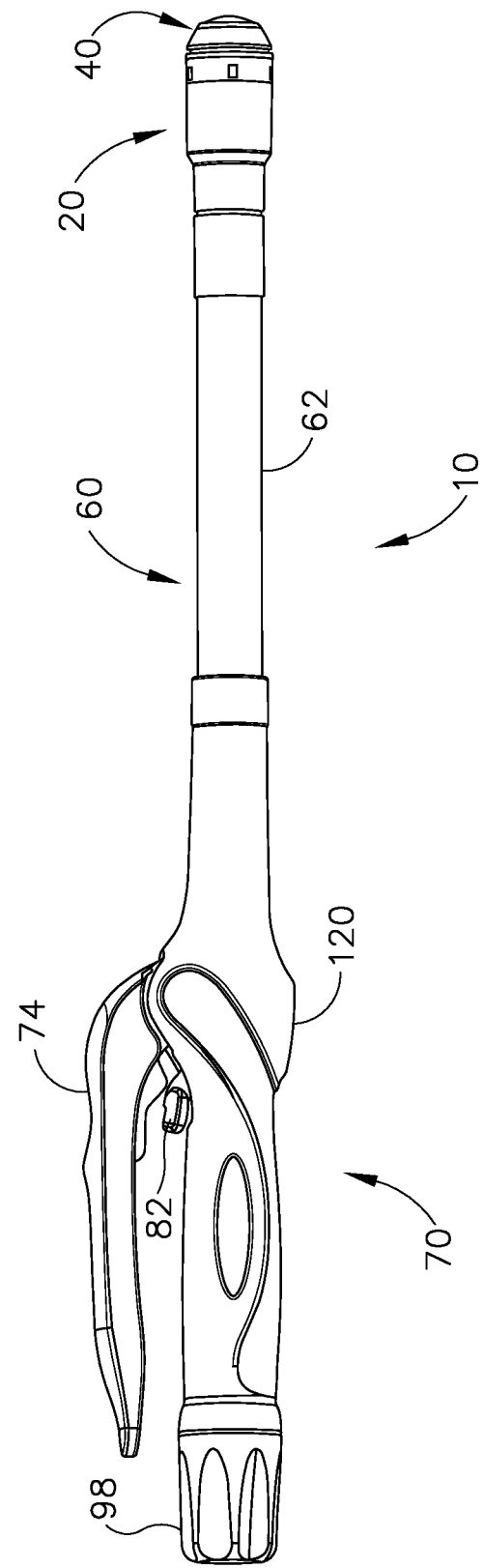

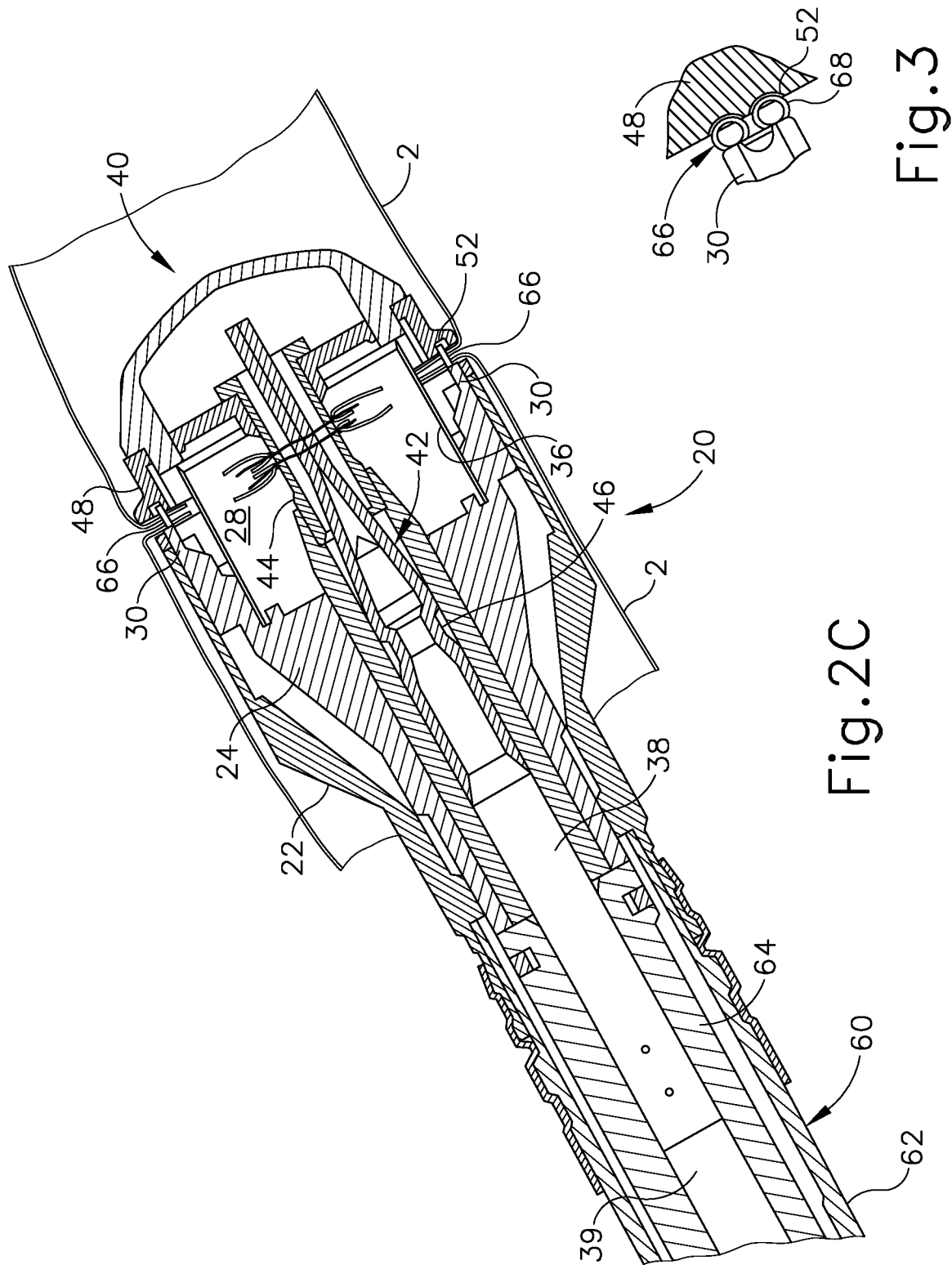

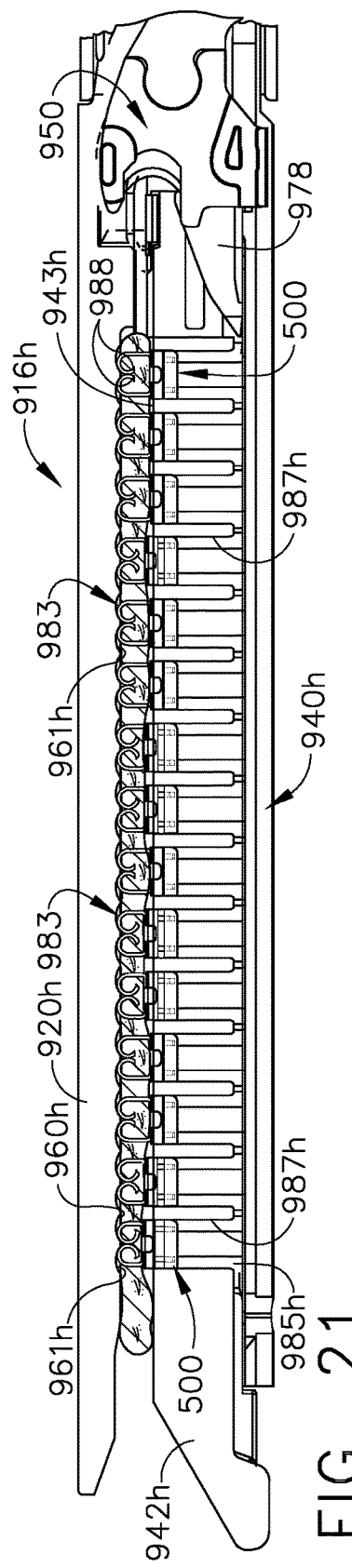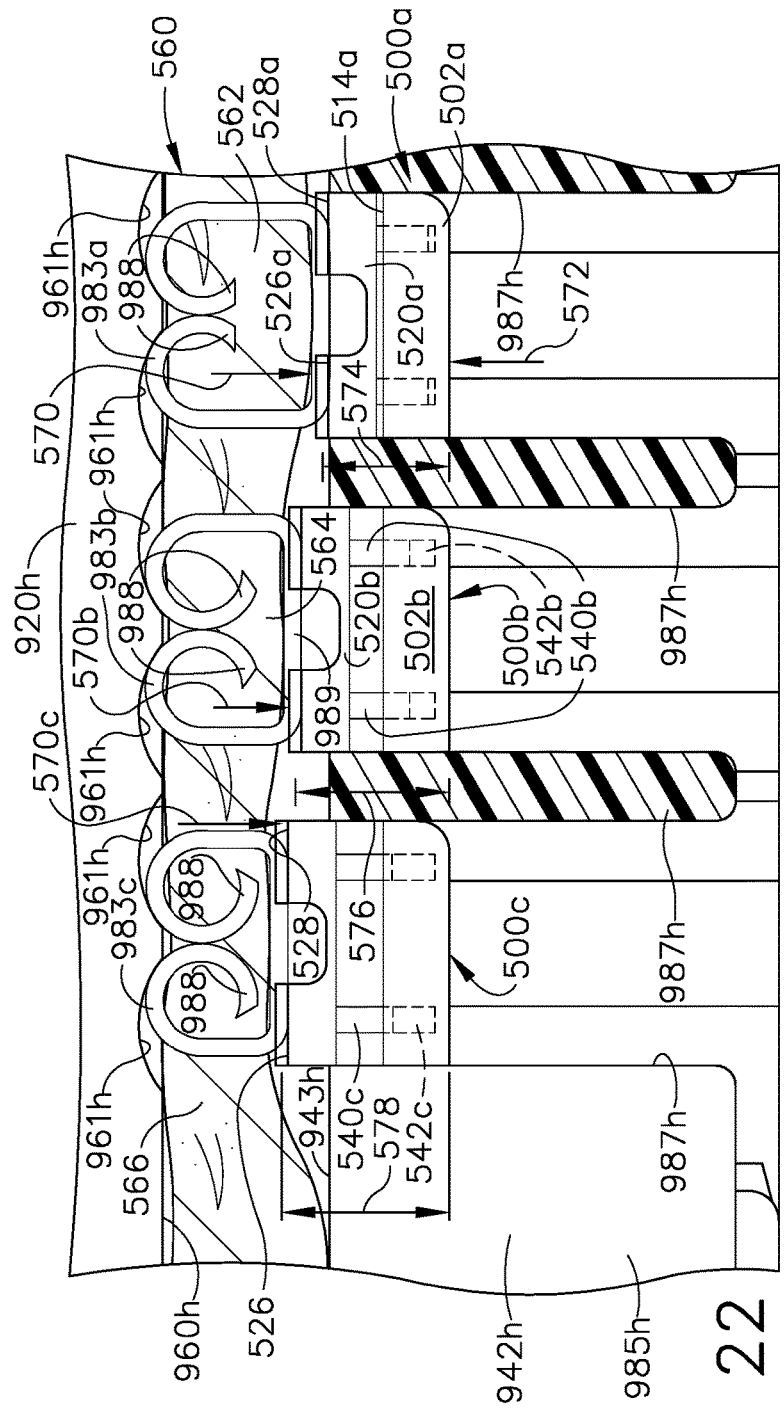
FIG. 21
FIG. 22

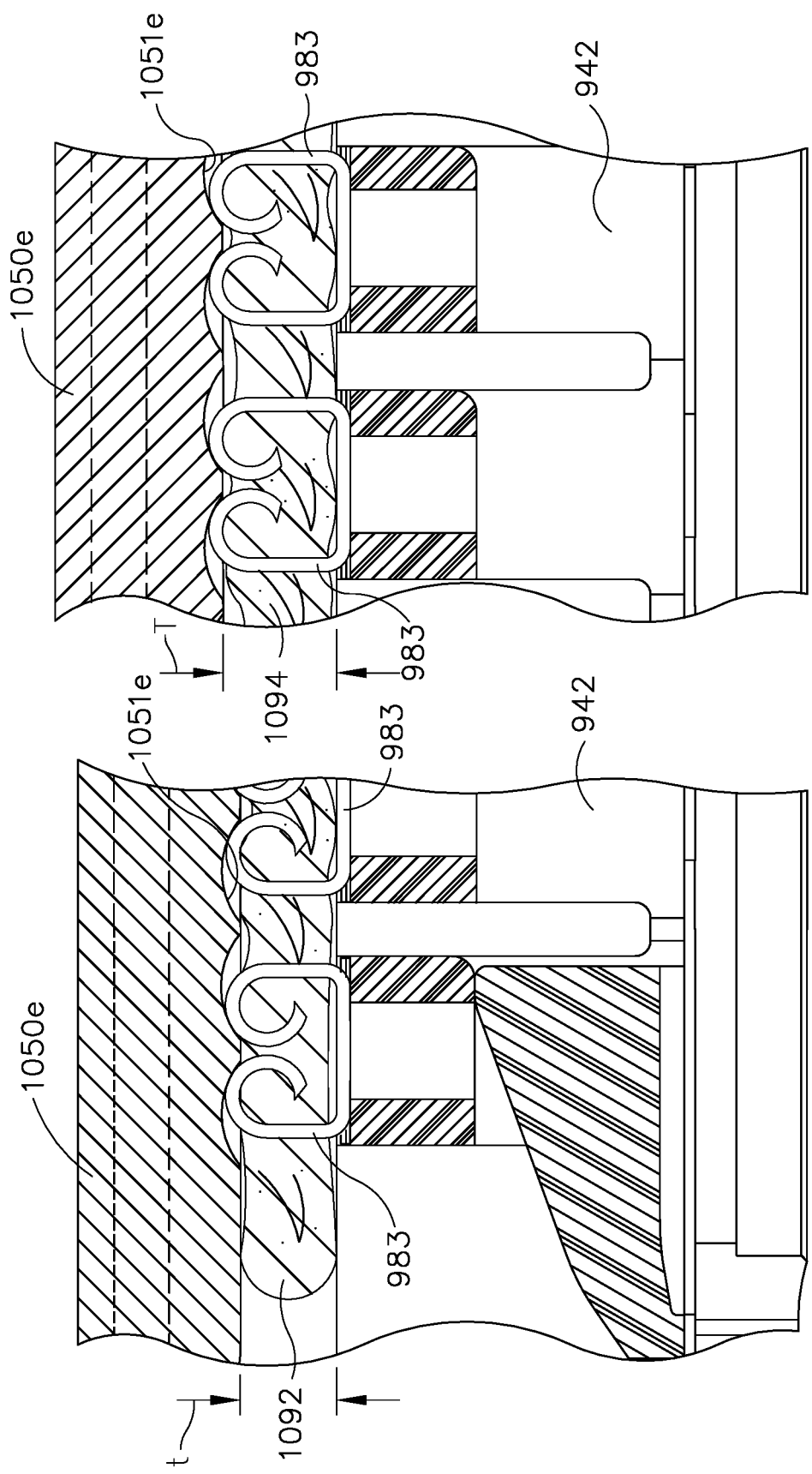

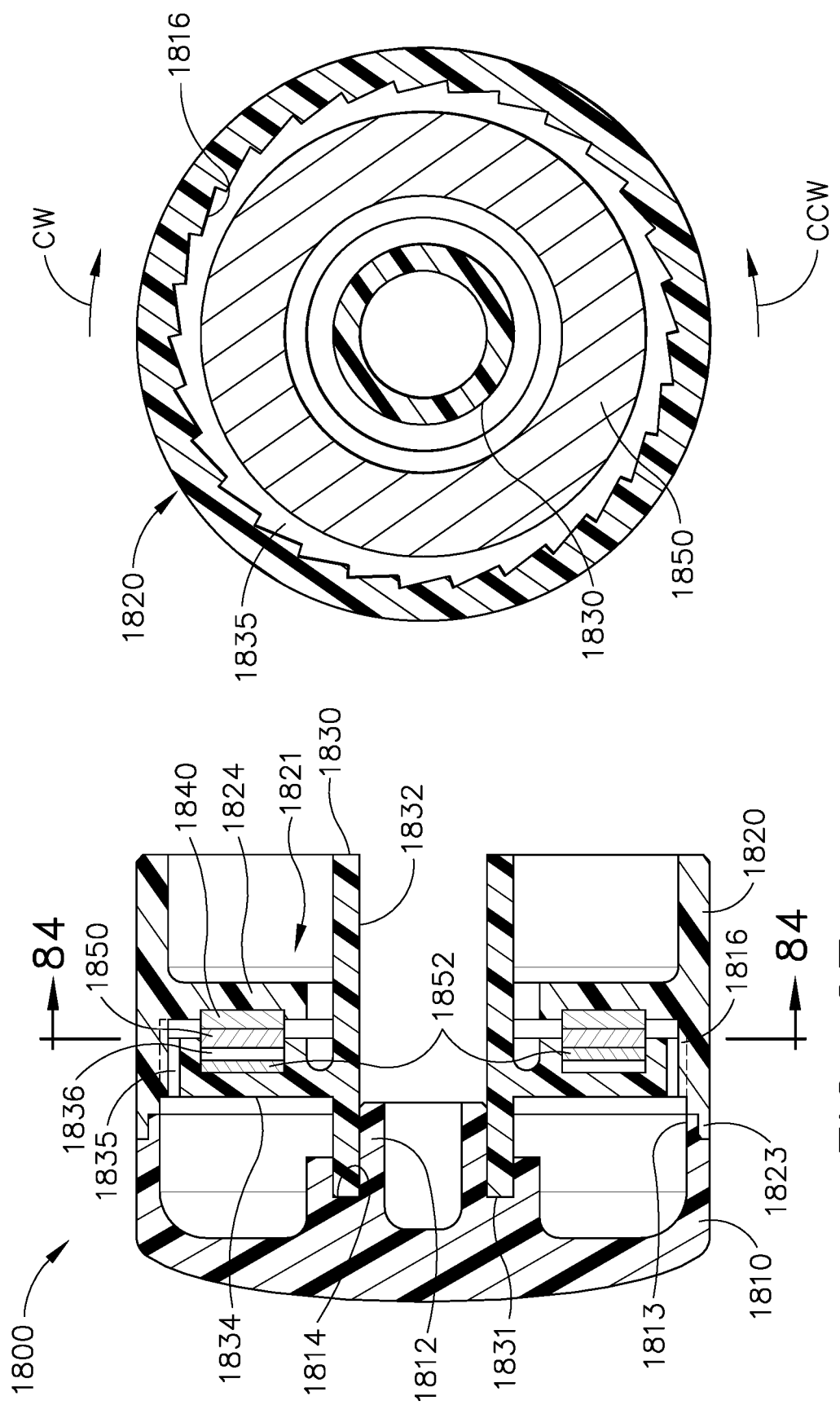

POWERED SURGICAL CIRCULAR STAPLER

This application is a continuation of U.S. Non-Provisional application Ser. No. 15/268,684, filed Sep. 19, 2016, now abandoned, entitled "Powered Surgical Circular Stapler" which is a continuation of U.S. Non-Provisional application Ser. No. 13/716,308, filed Dec. 17, 2012, entitled "Circular Stapler with Selectable Motorized and Manual Control," issued as U.S. Pat. No. 9,445,816 on Sep. 20, 2016.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

FIG. 21 is a longitudinal cross-sectional view of a staple applying assembly of other embodiments of the present invention wherein tissue of varying thickness is clamped therein;

FIG. 22 is an enlarged cross-sectional view of a portion of the staple applying assembly of FIG. 21;

FIG. 23 is an enlarged cross-sectional view of a portion of the endocutter depicted clamping a thin piece of tissue;

FIG. 24 is another enlarged cross-sectional view of a portion of the endocutter depicted in FIG. 23 clamping a thicker piece of tissue;

FIG. 27 is a cross-sectional view of a knob assembly embodiment of the present invention;

FIG. 28 is a cross-sectional view of the knob assembly of FIG. 27 taken along line 84-84 in FIG. 27;

Figure 2A:
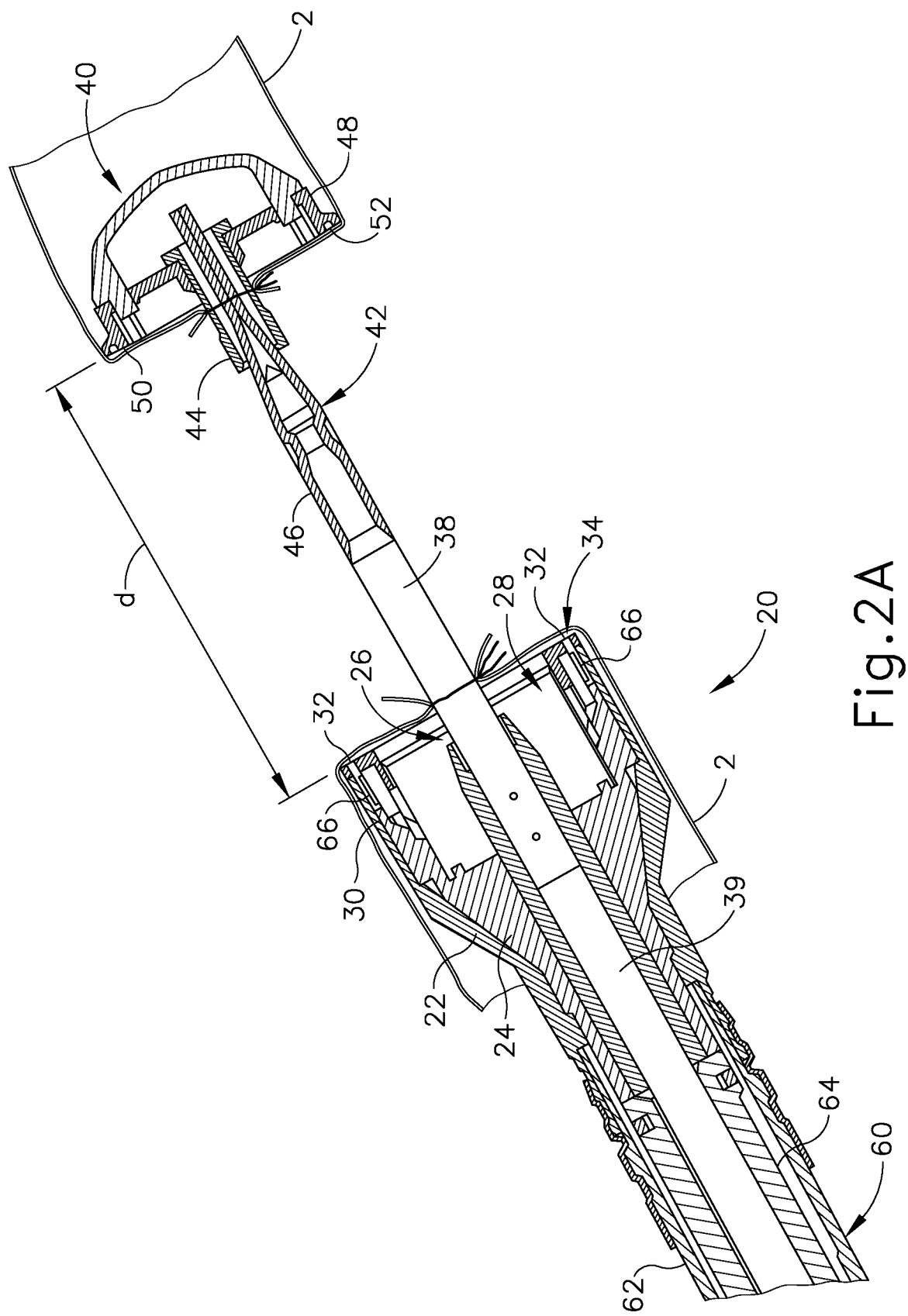
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2B:
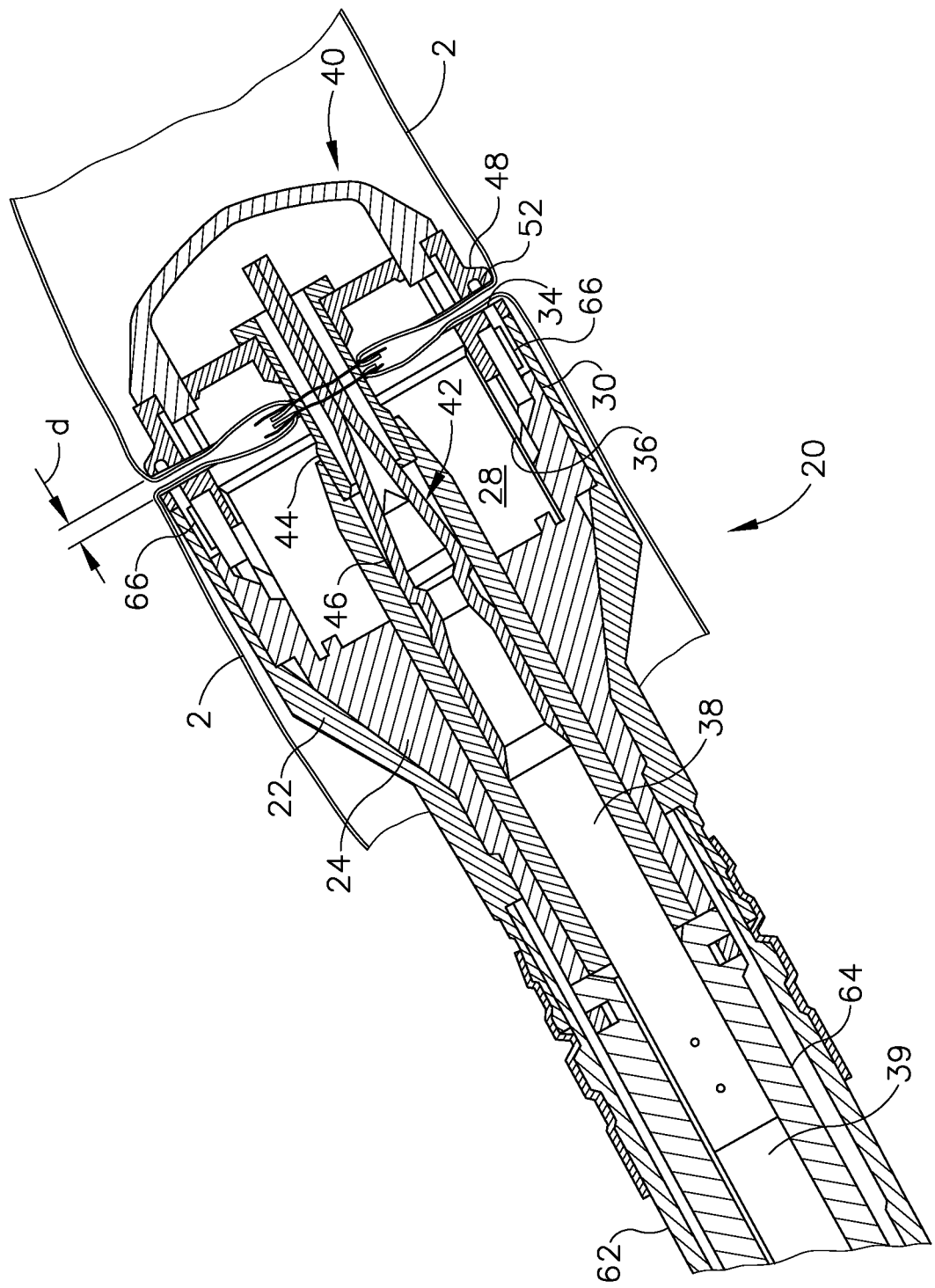
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
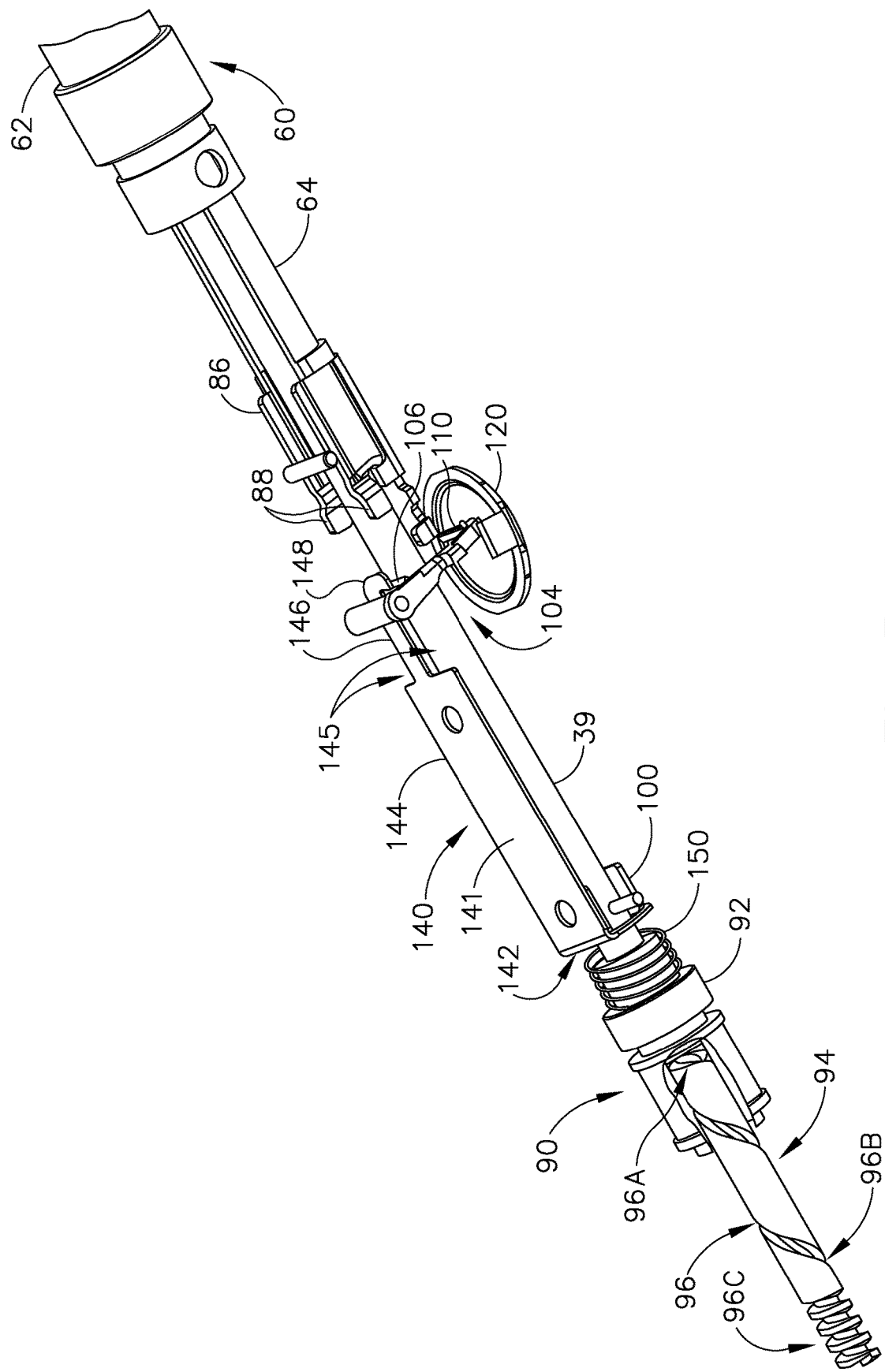
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70).

As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285, 945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40)

and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
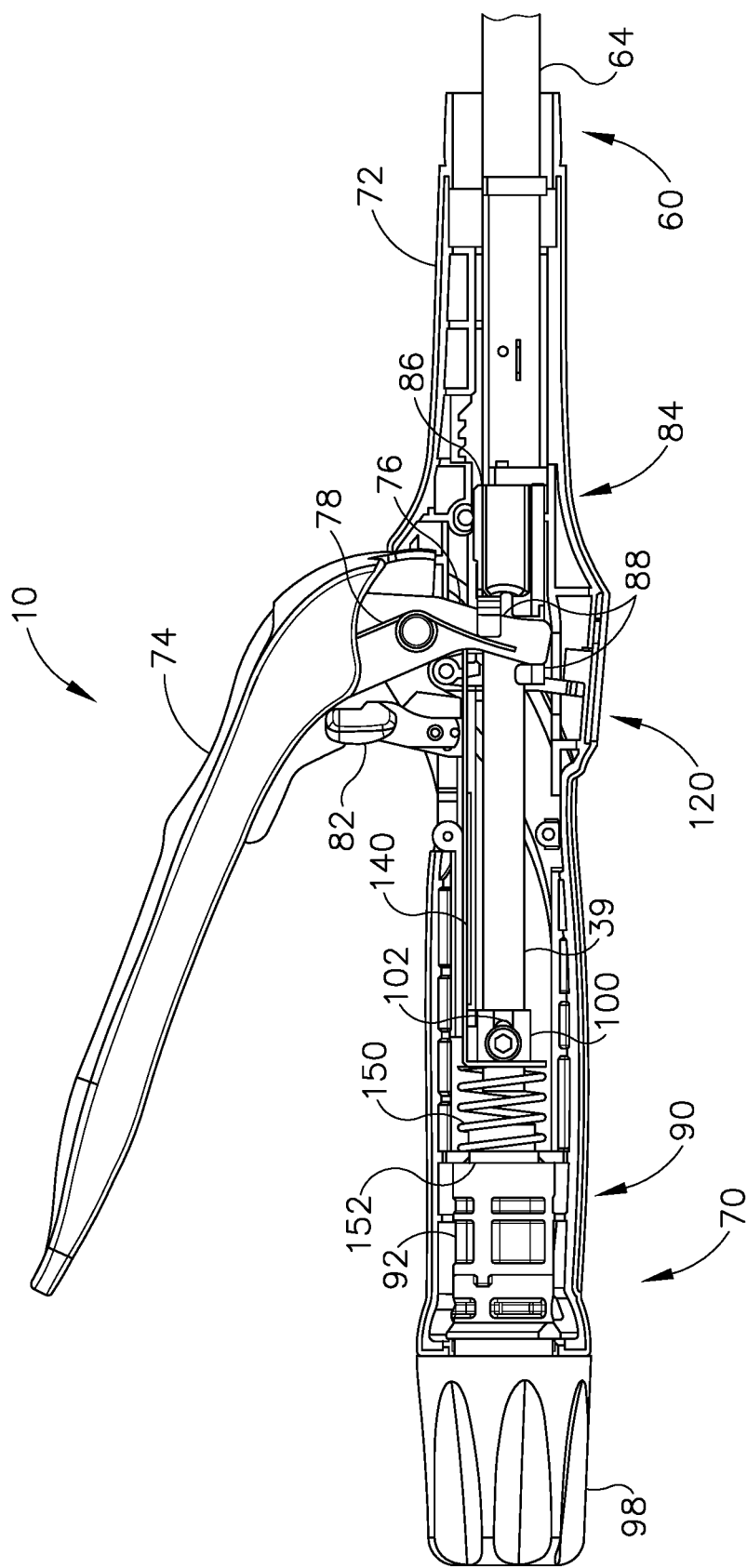
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
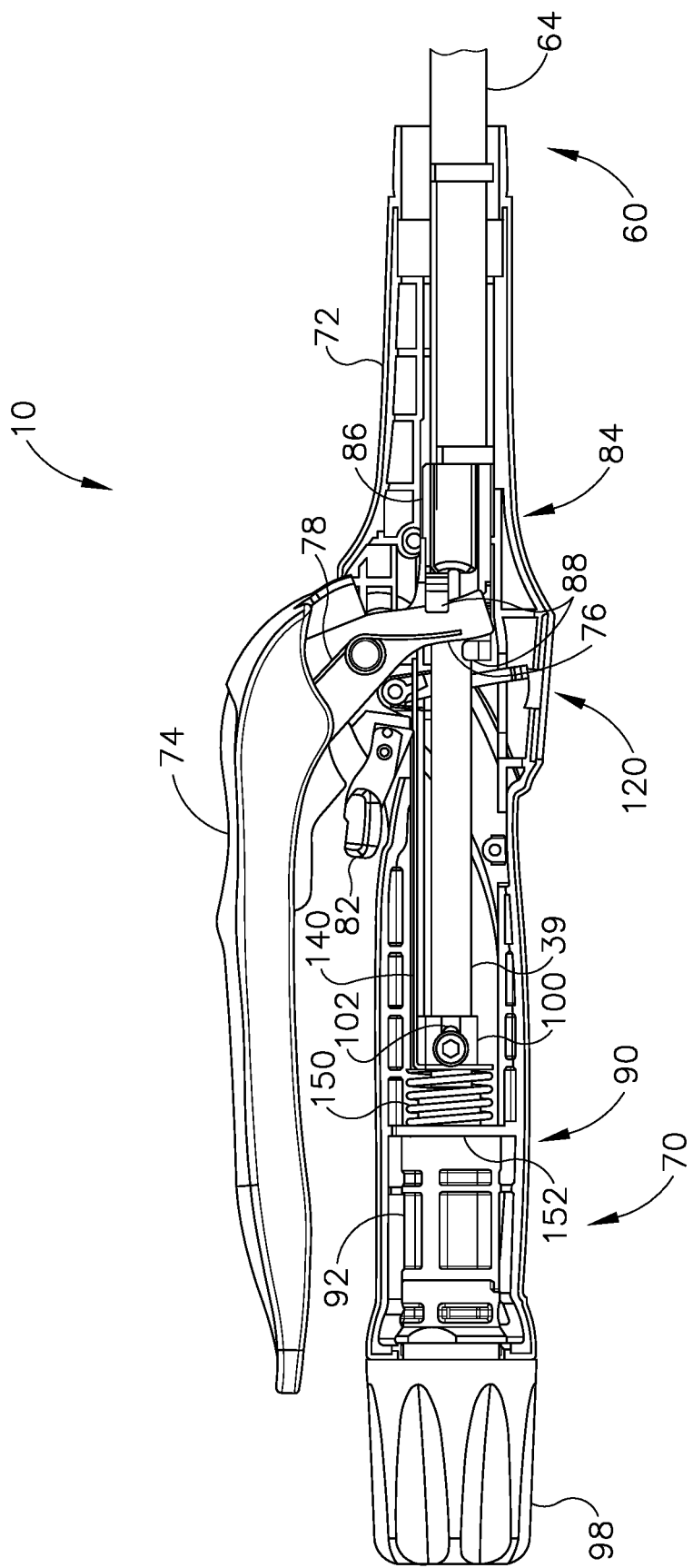
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Motorized Circular Stapling Surgical Instrument with Selectable Control In some instances, it may be desirable to provide motorized control of instrument (10). It may further be desirable to enable a user to select between either motorized control or manual control of a motorized version of circular surgical stapling instrument (10). For example, instrument (10) may include an operational mode selection assembly that allows the user to disengage an automated, motorized rotary actuation system and provide manual actuation of that system. It may also be desirable to provide a switch assembly for changing the mode of a single rotary drive between a tissue clamping mode and a tissue cutting/stapling mode. In other words, such a switch assembly may enable a single rotary drive to either actuate anvil (40) clamping features or actuate knife (36) and staple driving features of instrument (10). The examples below include merely illustrative versions of instrument (10) where a single motor can be used to control both clamping and cutting/stapling of tissue via a single rotary drive; where the operator can select between motorized operation and manual operation; and a stapling head cartridge assembly that is responsive to the single rotary drive in motorized and manual operation.

A. Exemplary Operational Mode Selection Assembly

Figure 7:
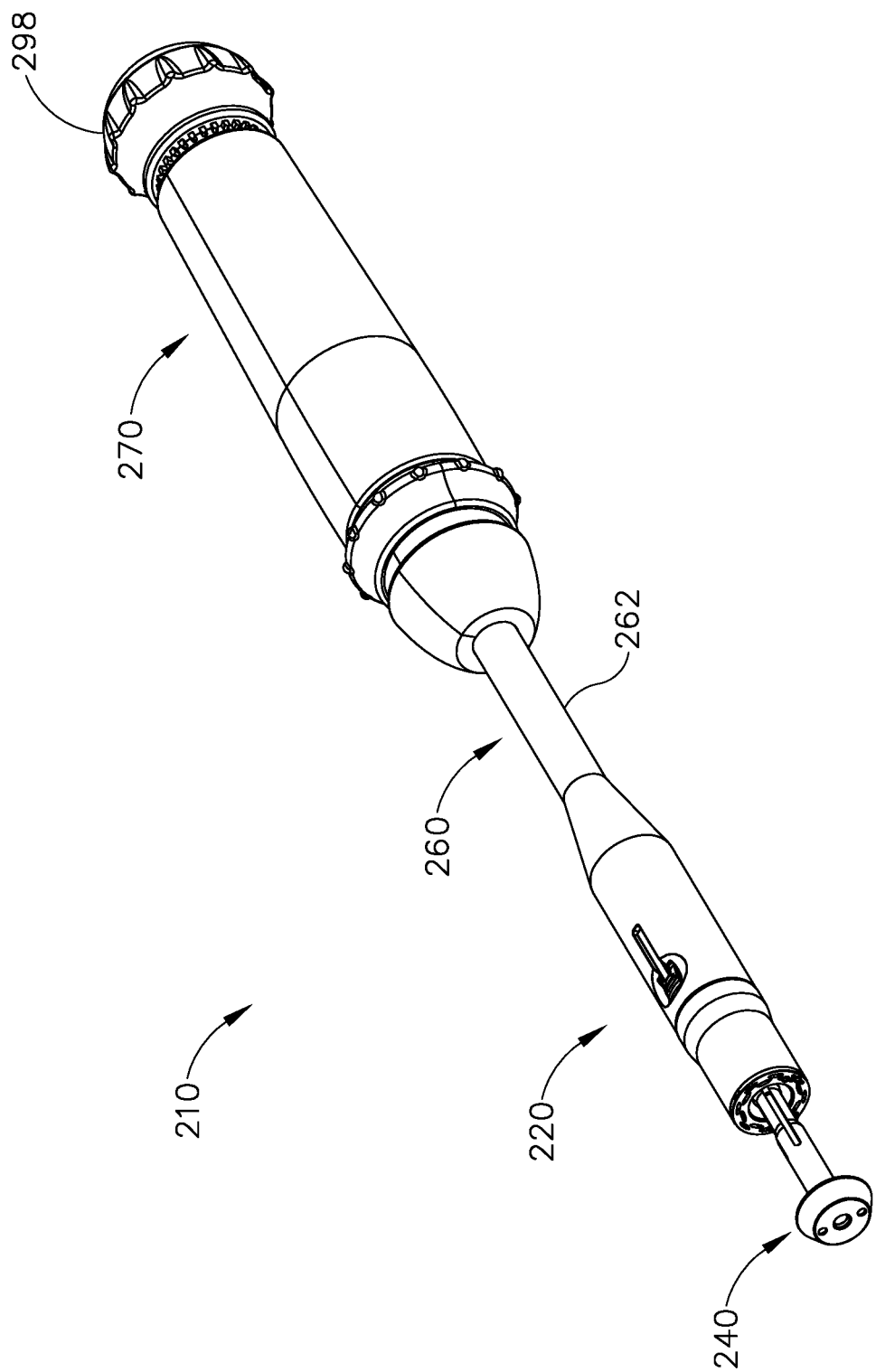
FIG. 7 depicts a perspective view of another exemplary circular stapling surgical instrument.

FIG. 7 shows another exemplary circular stapling instrument (210), which is a selectively motorized variation of instrument (10). Instrument (210) of this example comprises a stapling head assembly (220), an anvil (240), a shaft assembly (260), and a handle assembly (270). Stapling head assembly (220) is similar to stapling head assembly (20) in that stapling head assembly (220) selectively couples with anvil (240). Stapling head assembly (220) is operable to clamp tissue between staple pockets (32) and staple forming pockets (52) of anvil (240). Stapling head assembly (220) comprises a cylindrical knife (36) that is operable to sever tissue captured between stapling head assembly (220) and anvil (240). Stapling head assembly (220) drives staples (66) through the tissue captured between stapling head assembly (220) and anvil (240). Stapling instrument (210) may be used to create a secure anastomosis (e.g., an end-to-end anastomosis) within a gastro-intestinal tract of a patient or elsewhere.

Stapling head assembly (220) differs from stapling head assembly (20) in that stapling head assembly (220) is operable to clamp tissue, sever tissue, and staple tissue all in response to a single rotary input communicated via shaft assembly (260). Accordingly, actuation inputs translated linearly through shaft assembly (260) are not required for stapling head assembly (220), though stapling head assembly (220) may comprise a translating clutch feature. By way of example only, at least part of stapling head assembly (220) may be configured in accordance with at least some of the teachings of U.S. patent application Ser. No. 13/716,318, entitled "Motor Driven Rotary Input Circular Stapler with Modular End Effector," filed on Dec. 17, 2012, and issued as U.S. Pat. No. 9,597,081 on Mar. 21, 2017, the disclosure of which is incorporated by reference herein. Other suitable configurations for stapling head assembly (220) will be apparent to those of ordinary skill in the art in view of the teachings herein.

Shaft assembly (260) is similar to shaft assembly (60) in that shaft assembly (260) couples handle assembly (270) with stapling head assembly (220). Shaft assembly (260) differs from shaft assembly (60) in that shaft assembly (260) comprises a single actuation feature, rotary driver actuator (264) shown in FIG. 8. Driver actuator (264) is operable to drive stapling head assembly (220) to clamp tissue, sever tissue, and staple tissue. Accordingly, linear actuation through shaft assembly (260) is not required, though rotary driver actuator (264) may translate longitudinally to shift between a tissue clamping mode and a tissue cutting/stapling mode. For instance, driver actuator (264) may translate from a first longitudinal position, in which rotation of driver actuator (264) provides clamping of tissue at stapling head assembly (220), to a second longitudinal position, in which rotation of driver actuator (264) provides cutting and stapling of tissue at stapling head assembly (220). Some versions of shaft assembly (260) may include one or more flexible sections. An example of a shaft assembly that is configured with flexible sections and that may be incorporated into shaft assembly (260) is disclosed in U.S. patent application Ser. No. 13/716,323, entitled "Motor Driven Rotary Input Circular Stapler with Lockable Flexible Shaft," filed on Dec. 17, 2012, and issued as U.S. Pat. No. 9,463,022 on Oct. 11, 2016, the disclosure of which is incorporated by reference herein. Alternatively, shaft assembly (260) may be rigid along the length of shaft assembly (260) or have one or more flexible sections configured in some other fashion.

Figure 8:
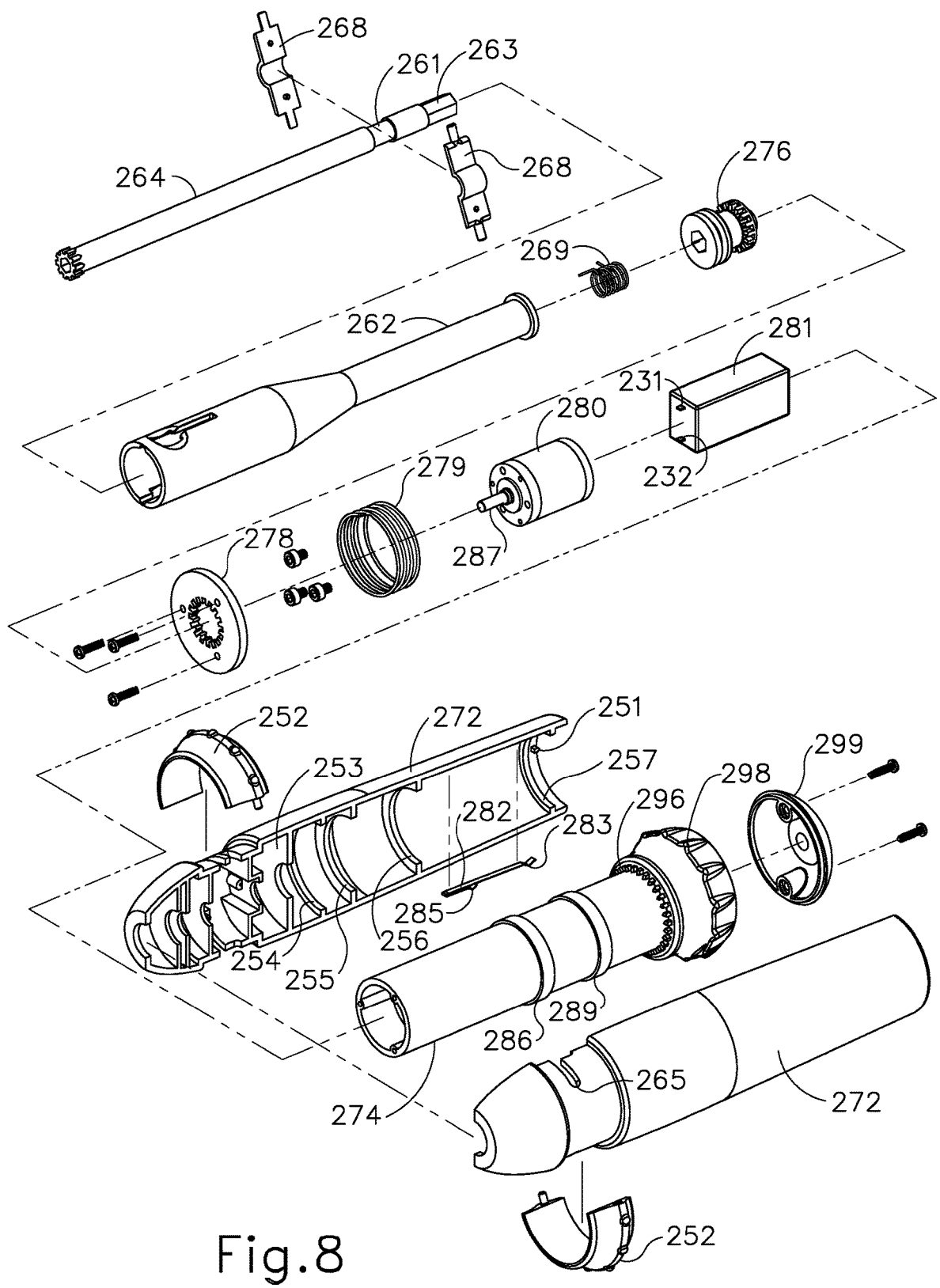
FIG. 8 depicts an exploded view of the handle and shaft assemblies of the instrument of FIG. 7.
Figure 9:
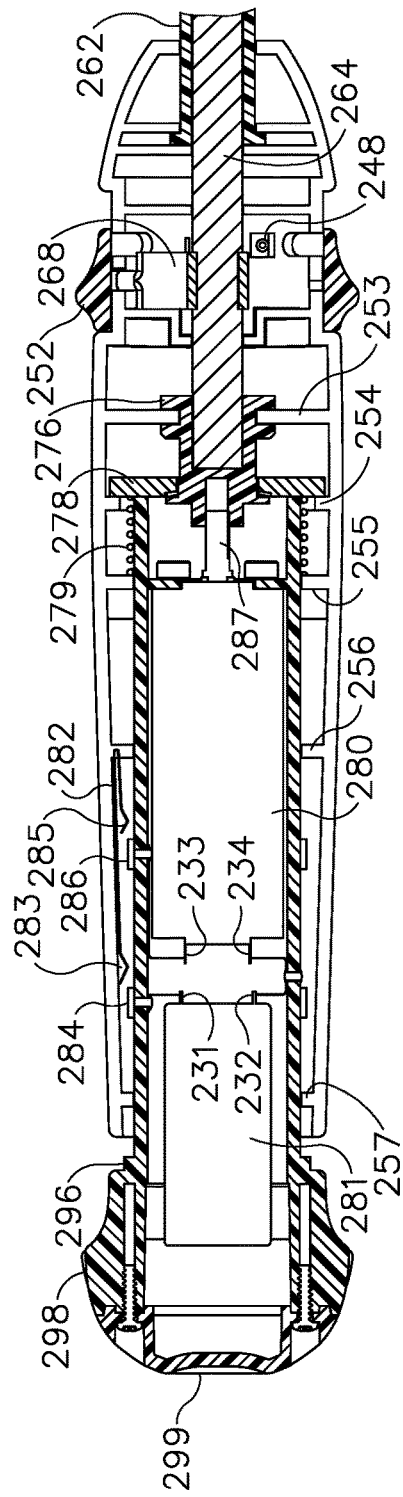
FIG. 9 depicts a cross sectional view of the handle assembly of the instrument of FIG. 7.
Figure 10:
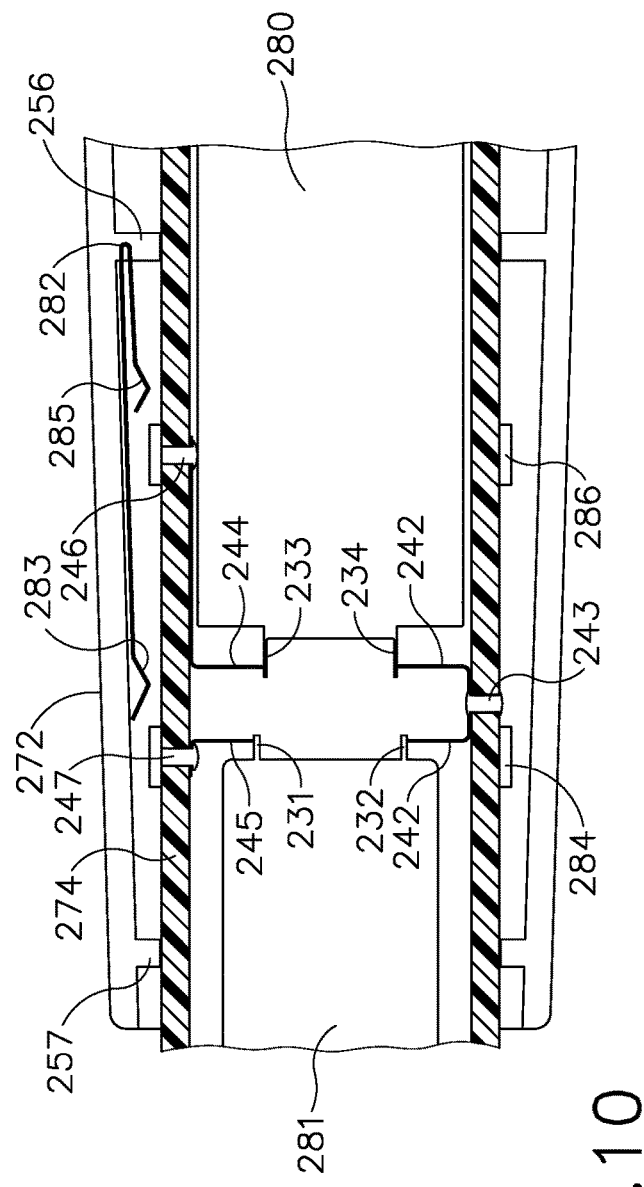
FIG. 10 depicts an enlarged, partial cross sectional view of the motor and battery assemblies of FIG. 7.
Figure 11A:
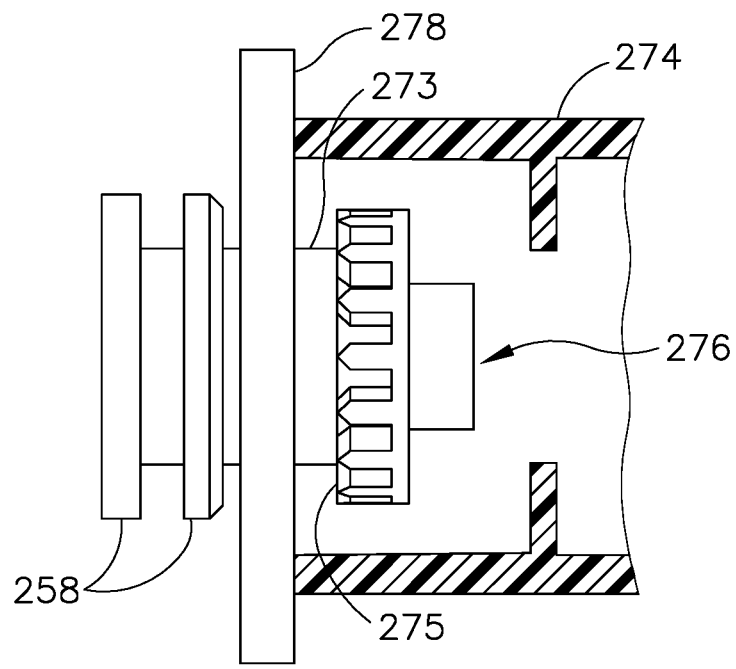
FIG. 11A depicts a side elevational view of an operational mode selection assembly of the instrument of FIG. 7, with a first gear disengaged from a second gear.
Figure 11B:
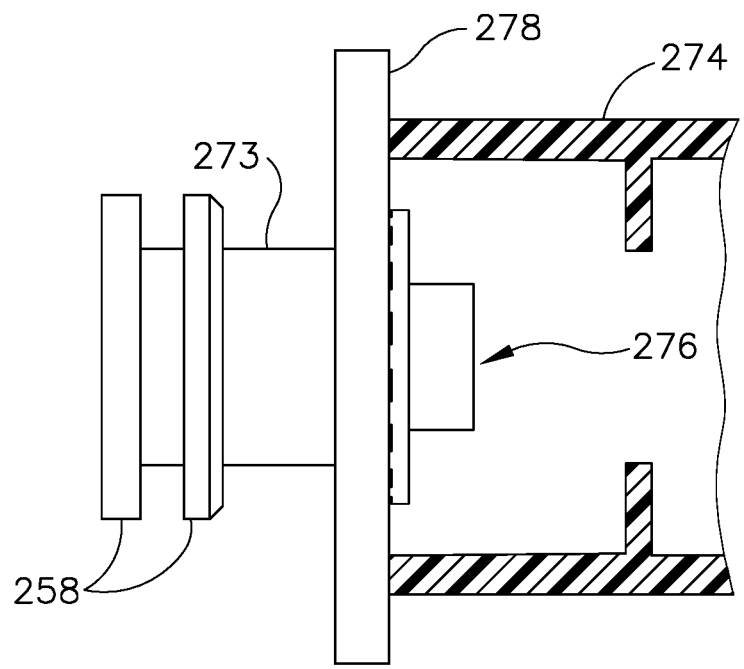
FIG. 11B depicts a side elevational view of the operational mode selection assembly of FIG. 11A, with the first gear engaged with the second gear.

Handle assembly (270) is shown in FIGS. 8-10. Handle assembly (270) comprises a handle housing (272), a motor housing (274), a motor (280), a battery (281), a rotation knob (298), an operational mode selection assembly (which is shown in FIGS. 11A-11B), and a firing ring (252). Motor housing (274) is positioned within handle housing (272). Handle housing (272) comprises ribs (255, 256, 257) extending inwardly into handle housing (272) to support motor housing (274), as shown in FIG. 9. Battery (281) is positioned proximal to motor (280) within motor housing (274). Battery (281) may be removed from motor housing (274) to be replaced, discarded, or recharged. As best seen in FIG. 10, battery (281) comprises electrical contacts (231, 232) extending distally from battery (281). Motor (280) comprises electrical contacts (233, 234) extending proximally from motor (280). Battery electrical contact (232) and motor electrical contact (234) are coupled via conductive metal band (242). Screw (243) couples band (242) to motor housing (274) to fix the position of band (242) relative to motor housing (274). Accordingly, band (242) is configured to constantly couple battery electrical contact (232) and motor electrical contact (234).

As shown in FIG. 10, battery electrical contact (231) is coupled to a conductive metal band (245). Metal band (245) is secured to motor housing (274) via a conductive screw (247). Motor electrical contact (233) is coupled to a conductive metal band (244). Metal band (244) is secured to motor housing (274) via a conductive screw (246). Motor housing (274) is formed of an electrically insulative material (e.g., plastic) and comprises annular contacts (284, 286) wrapped around motor housing (274). Screws (246, 247) are each coupled with a respective annular contact (284, 286) to electrically couple battery electrical contact (231) and motor electrical contact (233) to annular contacts (284, 286), respectively.

Another conductive metal band (282) is secured to handle housing (272). Each end of metal band (282) forms a respective spring contact (283, 285). Motor housing (274) translates proximally and/or distally relative to handle housing (272) to selectively couple and/or decouple spring contacts (283, 285) with annular contacts (284, 286). In particular, when motor housing (274) is in a distal position (FIG. 15A), spring contact (283) engages annular contact (284) and spring contact (285) engages annular contact (286) to couple battery (281) with motor (280) and supply power to motor (280). It should be understood that, since spring contacts (283, 285) are part of the same conductive metal band (282), and since contacts (232, 234) are already coupled via band (242), the engagement between spring contacts (283, 285) and annular contacts (284, 286) completes a circuit between battery (281) and motor (280). This positioning is used to provide motorized actuation of stapling head assembly (220) as will be described in greater detail below. When motor housing (274) is in a proximal position (FIG. 17A), spring contacts (283, 285) are decoupled from annular contacts (284, 286), such that battery (281) is decoupled from motor (280) and motor (280) does not receive power. This positioning is used to provide manual actuation of stapling head assembly (220) as will be described in greater detail below. The annular shape of annular contacts (284, 286) enables proper contact between spring contacts (283, 285) and annular contacts (284, 286) regardless of the angular position of motor housing (274) within handle housing (272). In some versions, band (282) may include a break that is coupled with an external switch, such that a user may actuate the external switch in order to complete the coupling between battery (281) and motor (280) after motor housing (274) is in the distal position.

A proximal end of motor housing (274) is fixedly secured to rotation knob (298), as shown in FIG. 8. Rotation knob (298) protrudes proximally from handle housing (272) and comprises splines (296) extending distally from rotation knob (298). Handle housing (272) comprises corresponding teeth (251) to selectively engage splines (296). Rotation knob (298) is pulled and/or pushed to translate motor housing (274) within handle housing (272). When rotation knob (298) is in a proximal position (FIG. 17A), splines (296) are disengaged from handle housing (272) such that rotation knob (298) and motor housing (274) are free to rotate relative to handle housing (272). This positioning is used to provide manual actuation of stapling head assembly (220) as will be described in greater detail below. When rotation knob (298) is in a distal position (FIG. 15A), splines (296) engage corresponding teeth (251) in handle housing (272) to lock rotation knob (298) and motor housing (274) from rotating relative to handle housing (272). Splines (296) and teeth (251) thus provide a mechanical ground for motor housing (274) relative to handle housing (272). This positioning is used to provide motorized actuation of stapling head assembly (220) as will be described in greater detail below. Rotation knob (298) is biased to the distal position by a resilient member (279) in handle housing (272). In particular, resilient member (279) extends distally from rib (255) of handle housing (272) to a first gear (278), which is unitarily secured to the distal end of motor housing (274). When rotation knob (298) is in the proximal position, resilient member (279) compresses between first gear (278) and rib (255) to resiliently bias handle housing (272) to the distal position.

Figure 12:
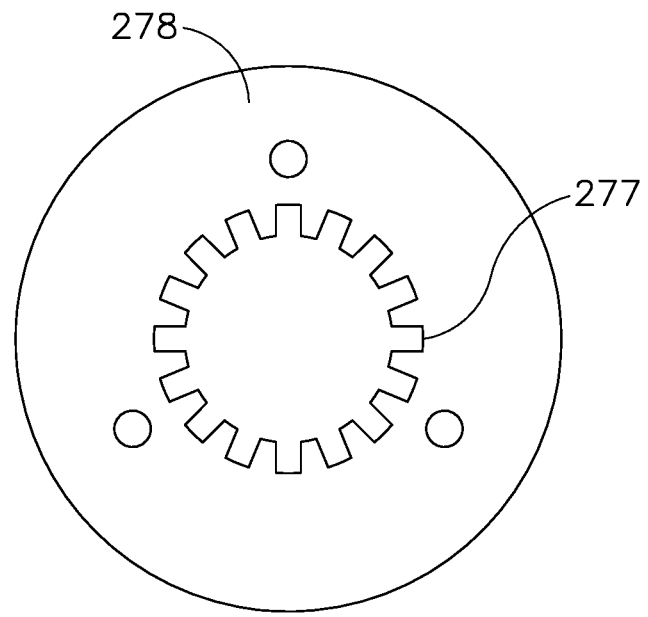
FIG. 12 depicts a front elevational view of the first gear of the operational mode selection assembly of FIG. 11A.
Figure 13:
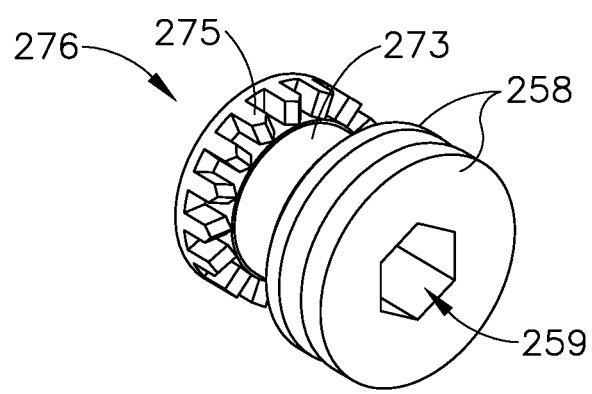
FIG. 13 depicts a perspective view of the second gear of the operational mode selection assembly of FIG. 11A.

An operational mode selection assembly is positioned distal to motor housing (274) within handle housing (272). As shown in FIGS. 11-13, the operational mode selection assembly comprises a first gear (278) and a second gear (276), with first gear (278) being coaxially and slidably disposed about second gear (276). First gear (278) comprises square teeth (277) aligned around an inner opening of first gear (278), as shown in FIG. 12. Teeth (277) define a circumferentially spaced array of recesses. Second gear (276) comprises a shaft (273), splines (275), and annular flanges (258), as shown in FIG. 13. Shaft (273) has a distally presented opening (259). Distally presented opening (259) is hexagonal to receive proximal end (263) of driver actuator (264), which is also hexagonal (FIG. 8). Shaft (273) also has a proximally presented opening (not shown) that is semi-circular to complement and receive drive shaft (287) extending distally from motor (280). Other suitable shapes and configurations of shafts (263, 287) may used to couple second gear (276) with shafts (263, 287).

Splines (275) of second gear (276) are positioned on a proximal end of shaft (273) and extend distally. Splines (275) correspond to teeth (277) of first gear (278), such that splines (275) are configured to fit within the recesses defined between teeth (277). A pair of annular flanges (258) are positioned at a distal end of shaft (273) and extend outwardly to engage an inwardly extending annular rib (253) of handle housing (272), thereby fixing the longitudinal position of second gear (276) within handle housing (272). While annular rib (253) fixes the longitudinal position of second gear (276) within handle housing (272), annular rib (253) nevertheless allows second gear (276) to rotate relative to handle housing (272). Other suitable engagement features to longitudinally fix second gear (276) will be apparent to one with ordinary skill in the art based on the teachings herein.

Figure 17A:
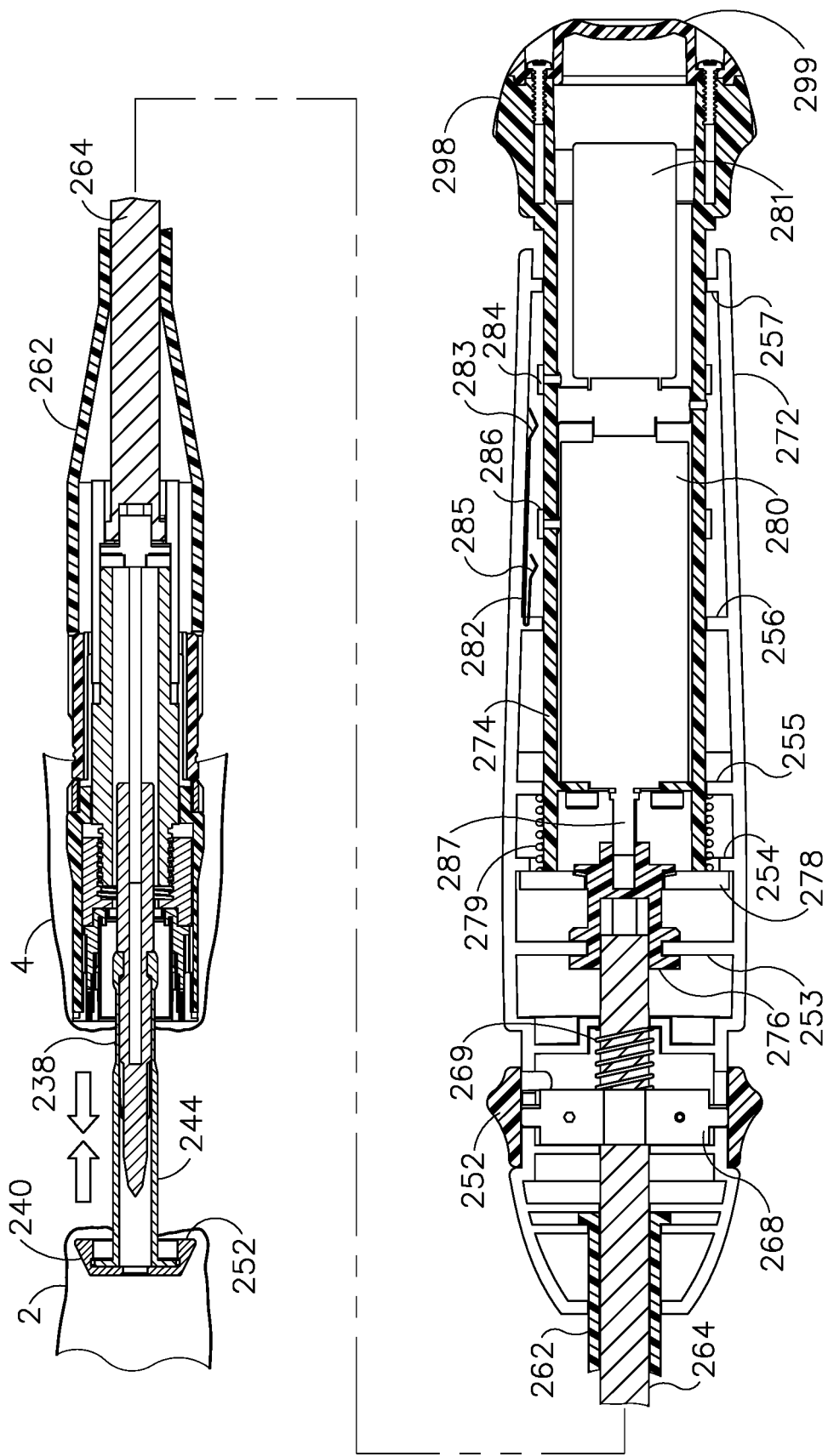
FIG. 17A depicts a cross sectional view of the instrument of FIG. 7, with a manual operational mode selected, showing an anvil being coupled to a trocar.

First gear (278) is positioned around second gear (276), as shown in FIGS. 11A-11B. First gear (278) is fixedly coupled to a distal end of motor housing (274) such that first gear (278) translates and rotates unitarily with motor housing (274). When motor housing (274) is in a proximal position, as shown in FIGS. 11B and 17A, motor (280) and first gear (278) are also in a proximal position. In this position, drive shaft (287) of motor (280) is disengaged from second gear (276) and teeth (277) of first gear (278) engage splines (275) of second gear (276). Thus, when rotation knob (298) rotates, motor housing (274) and first gear (278) also rotate. This positioning thereby provides manual actuation of stapling head assembly (220), as will be described in greater detail below. With teeth (277) of first gear (278) engaged with splines (275), rotation knob (298) thereby rotates second gear (276) relative to motor housing (274). When motor housing (274) is in a distal position, as shown in FIGS. 11A and 15B, motor (280) and first gear (278) are also in a distal position. Motor (280) is engaged with second gear (276) via shafts (287, 273). First gear (278) slides over shaft (273) of second gear (276) to disengage splines (275). Thus, the rotation of drive shaft (287) of motor (280) thereby rotates second gear (276). This positioning thereby provides motorized actuation of stapling head assembly (220), as will be described in greater detail below. In other words, when knob (298) and motor housing (274) are in a distal position as shown in FIGS. 11A and 15B, motor (280) rotates second gear (276). When knob (298) and motor housing (274) are in a proximal position as shown in FIGS. 11B and 17A, knob (298) rotates second gear (276).

Figure 14:
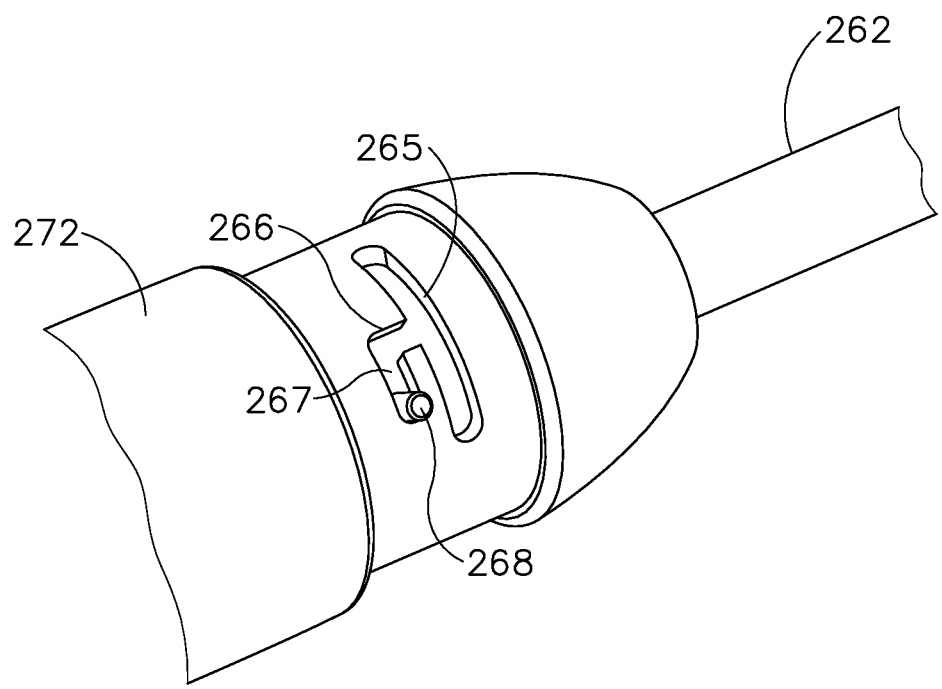
FIG. 14 depicts an enlarged, partial perspective view of the handle assembly of the instrument of FIG. 7.

Referring back to FIGS. 8-9, a distal end of second gear (276) is coupled to driver actuator (264), such that rotation of second gear (276) rotates driver actuator (264). Driver actuator (264) is similar to driver actuator (64). Accordingly, when second gear (276) is rotated, driver actuator (264) is rotated to adjust the gap distance d between anvil (240) and stapling head assembly (220). Handle housing (272) further comprises firing ring (252) and coupling member (268). Coupling member (268) is secured around recess (261) of driver actuator (264), as shown in FIG. 8. Accordingly, coupling member (268) translates with driver actuator (264), but driver actuator (264) is free to rotate within coupling member (268). Coupling member (268) comprises protrusions extending outwardly that connect coupling member (268) to firing ring (252). The protrusions of coupling member (268) extend through slots (265, 266, 267) of housing assembly (272), as shown in FIG. 14. Slot (265) extends circumferentially about part of handle assembly (272). Slot (266) extends proximally from slot (265). Slot (267) extends transversely from slot (266) and is substantially parallel with slot (265). Firing ring (252) is wrapped around handle housing (272) and is rotatable and translatable relative to handle housing (272) to manually drive the protrusions of coupling member (268) through slots (265, 266, 267).

When firing ring (252) is in a distal position, protrusions of coupling member (268) are positioned within slot (265) of handle housing (272). When coupling member (268) is positioned within slot (265), coupling member (268) couples driver actuator (264) with features in stapling head assembly (220) operable to adjust the gap distance d between anvil (240) and stapling head assembly (220). For instance, if coupling member (268) is rotated clockwise within slot (265), the gap distance d is decreased to close anvil (240) relative to stapling head assembly (220). If coupling member (268) is rotated counterclockwise within slot (265), the gap distance d is increased to open anvil (240) relative to stapling head assembly (220). A resilient member (269) is positioned proximal to coupling member (268) to bias coupling member (268) distally (FIG. 8). Coupling member (268) of firing ring (252) may then be translated proximally through slot (266) to slot (267). When firing ring (252) is in the proximal position, protrusions of coupling member (268) are positioned within slot (267). When coupling member (268) is positioned within slot (267), coupling member (268) couples driver actuator (264) with features in stapling head assembly (220) that drive knife (36) and staples (66) in response to rotation of driver actuator (264). For instance, if coupling member (268) is rotated clockwise within slot (267), stapling head assembly (220) drives knife (36) and staples (66). The configuration of slot (367) prevents coupling member (268) from being rotated counterclockwise.

Other suitable coupling member (268) rotation configurations will be apparent to one with ordinary skill in view of the teachings herein.

As shown in FIG. 9, a switch (248) is positioned in handle housing (272) to align with coupling member (268). When the motorized operational mode is selected, switch (248) is configured to electrically couple motor (280) and battery (281) when switch (248) is depressed, and switch (248) is configured to electrically decouple motor (280) and battery (281) when switch (248) is not depressed. Coupling member (268) is configured to engage and depress switch (248) when coupling member (268) is rotated. For instance, when coupling member (268) is in a neutral position (e.g., when coupling members (268) are aligned with respective slots (266)), switch (248) is not depressed and motor (280) is decoupled from battery (281). When coupling member (268) is rotated away from the neutral position, coupling member (268) engages switch (248) to depress switch (248) and couple motor (280) with battery (281) to operate instrument (210). It should be understood that housing (272) may include three switches (248). For instance, one switch (248) may be positioned for activation when firing ring (252) is rotated clockwise while in the proximal position (e.g., with coupling member (268) in slot (267)); with another switch (248) being positioned for activation when firing ring (252) is rotated clockwise while in the distal position (e.g., with coupling member (268) in slot (265)); with yet another switch (248) being positioned for activation when firing ring (252) is rotated counterclockwise while in the distal position. A control logic may be in communication with the switches (248) that are activated when firing ring (252) is rotated while in the distal position. Such a control logic may be operable to selectively reverse the direction of rotation by motor (280), to thereby provide selective advancement or retraction of trocar (238) and anvil (240) to adjust the gap distance d, depending on the direction in which firing ring (252) is rotated.

It should be understood that firing ring (252) and coupling member (268) act as a clutch control to shift driver actuator (264) from an anvil clamping mode (when coupling member (268) is in the distal position) to a cutting/stapling mode (when coupling member (268) is in the proximal position). An example of a stapling head assembly (220) responsive to such changes in driver actuator (264) positioning is disclosed in U.S. patent application Ser. No. 13/716,318, entitled "Motor Driven Rotary Input Circular Stapler with Modular End Effector," filed on Dec. 17, 2012, and issued as U.S. Pat. No. 9,597,081 on Mar. 21, 2017, the disclosure of which is incorporated by reference herein. Other suitable forms that stapling head assembly (220) may take will be apparent to those of ordinary skill in the art in view of the teachings herein. Outer tubular member (262) is coupled to actuator handle assembly (270). Outer tubular member (262) is similar to outer tubular member (62) to provide a mechanical ground between stapling head assembly (220) and handle assembly (270).

1. Motorized Operation

Figure 15A:
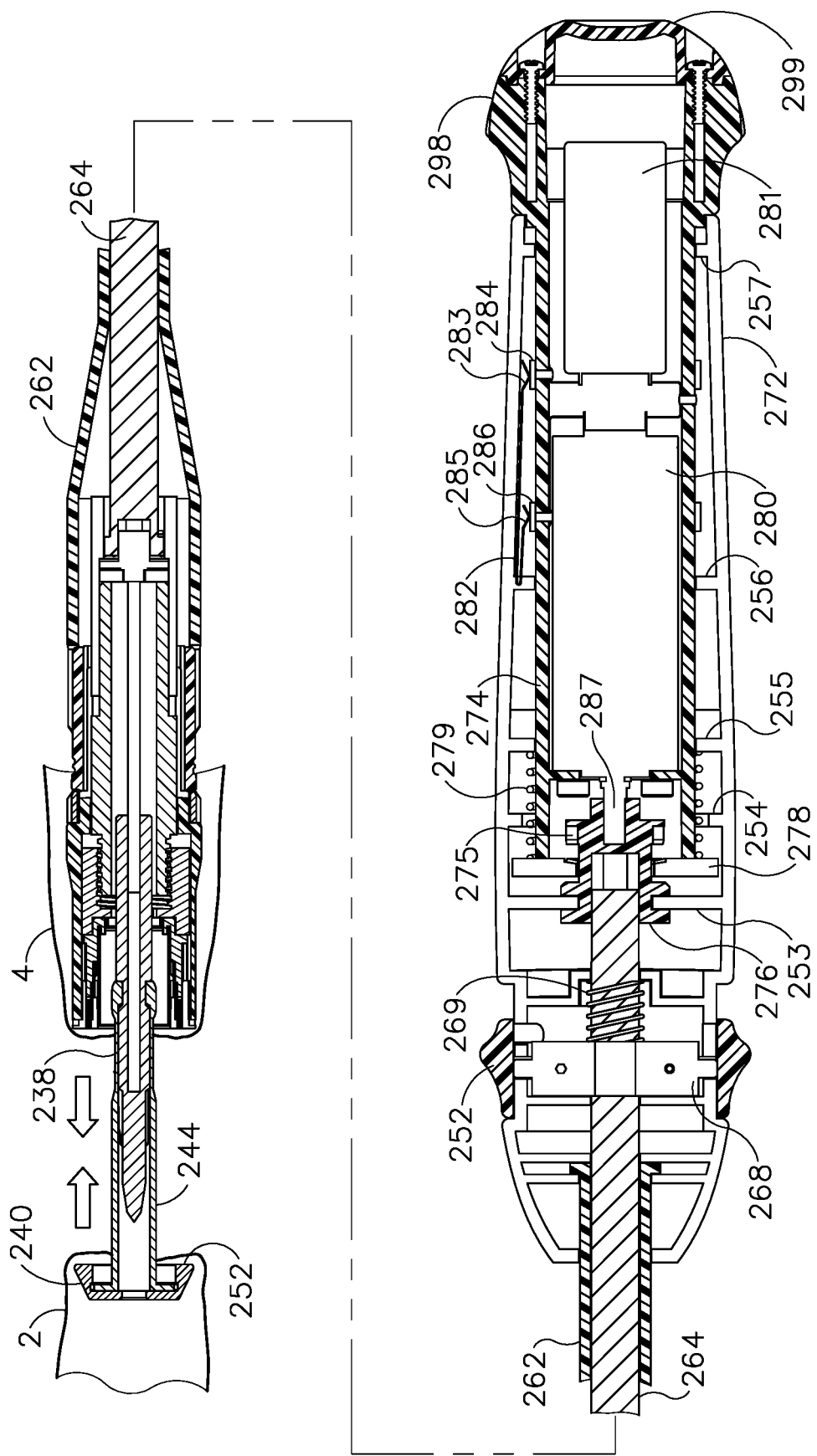
FIG. 15A depicts a cross sectional view of the instrument of FIG. 7, with a motorized operational mode selected, showing an anvil being coupled to a trocar.
Figure 15B:
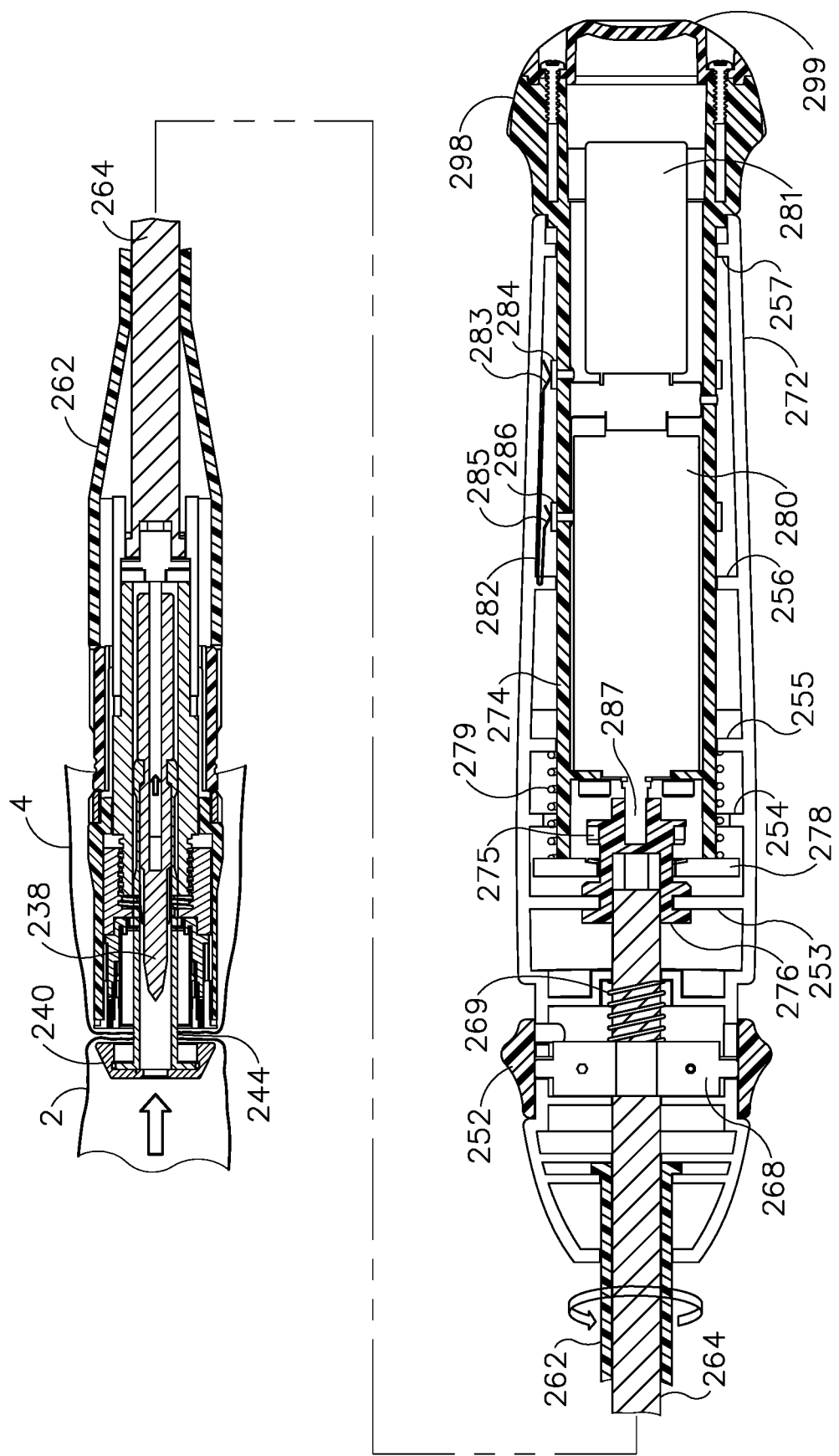
FIG. 15B depicts a cross sectional view of the instrument of FIG. 7, with a motorized operational mode selected, in a tissue clamping position.
Figure 15C:
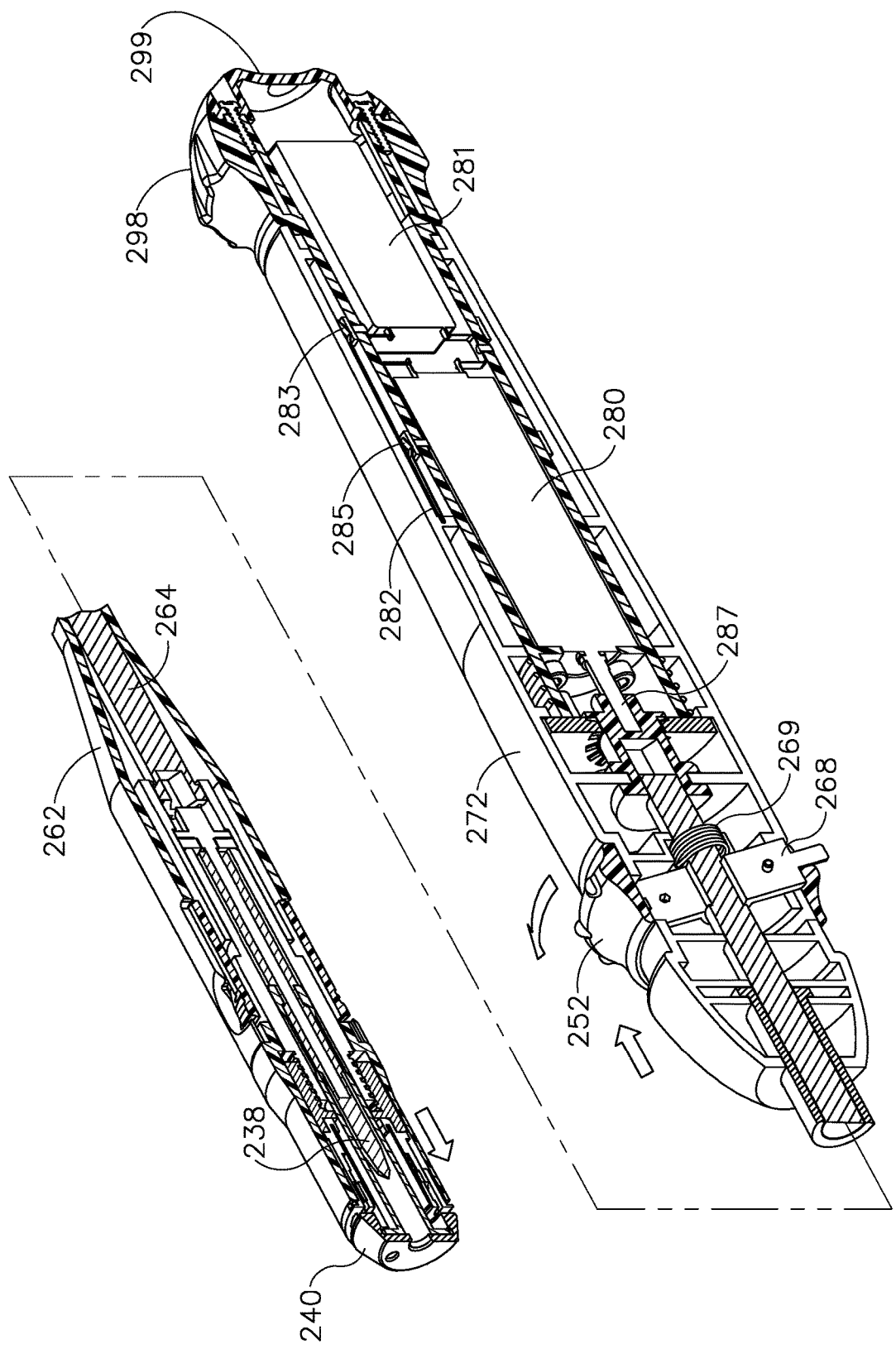
FIG. 15C depicts a cross sectional view of the instrument of FIG. 7, with a motorized operational mode selected, in a fired position.

FIGS. 15A-15C show instrument (210) during motorized operation. FIG. 15A shows anvil (240) being coupled to trocar (238). Anvil (240) couples with trocar (238) in a manner similar to that described above with respect to anvil (40) and trocar (38). When motorized operation is selected, rotation knob (298) is in a distal position. In the distal position, splines (296) of rotation knob (298) engage corresponding teeth (251) in handle housing (272) to lock rotation knob (298) from rotating relative to handle housing (272). When rotation knob (298) is in the distal position, motor housing (274) is also in a distal position. When motor housing (274) is in the distal position, spring contacts (283, 285) are aligned with annular contacts (284, 286) to couple electrical contact (231) of battery (281) with electrical contact (233) of motor (280). Power is supplied from battery (281) to motor (280) when coupling member (268) is rotated to depress switch (248). Motor (280) is engaged with second gear (276) via shafts (287, 273) and first gear (278) is disengaged from splines (275), thereby permitting second gear (276) to rotate relative to first gear (278), motor housing (274), and handle housing (272). Protrusions of coupling member (268) are positioned distally within slot (265) of handle housing (272) to lock the longitudinal position of firing ring (252) and driver actuator (264).

As shown in FIG. 15B, firing ring (252) is rotated clockwise to translate coupling member (268) within slot (267). As coupling member (268) is rotated, switch (248) is depressed to couple motor (280) and battery (281) and supply power to motor (280). Motor (280) is thus activated to rotate shaft (287). Shaft (287) thereby rotates second gear (276). Because second gear (276) is coupled to driver actuator (264), the rotation of second gear (276) also rotates driver actuator (264). This rotation of driver actuator (264) drives features in stapling head assembly (220) to adjust the gap distance d between anvil (240) and stapling head assembly (220). Once anvil (240) is in a desired position relative to stapling head assembly (220), firing ring (252) is rotated counterclockwise to a neutral position to release switch (248) such that motor (280) is decoupled from battery (281). Instrument (210) may then be fired, as shown in FIG. 15C. Firing ring (252) is translated to position coupling member (268) out of slot (265) to the proximal position in slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Firing ring (252) is rotated clockwise within slot (267) to depress switch (248) to again couple battery (281) with motor (280) to supply power to motor (280). Motor (280) is again rotated with coupling member (268) and driver actuator (264) in the proximal position. This rotation is communicated to driver actuator (264) via drive shaft (287) and second gear (276), and is thereby communicated to driver actuator (264) to cut and staple tissue (2, 4). Firing ring (252) may then be rotated counterclockwise within slot (267) to the neutral position to release switch (248) and decouple motor (280) from battery (281).

2. Selection of Operation Mode

Figure 16:
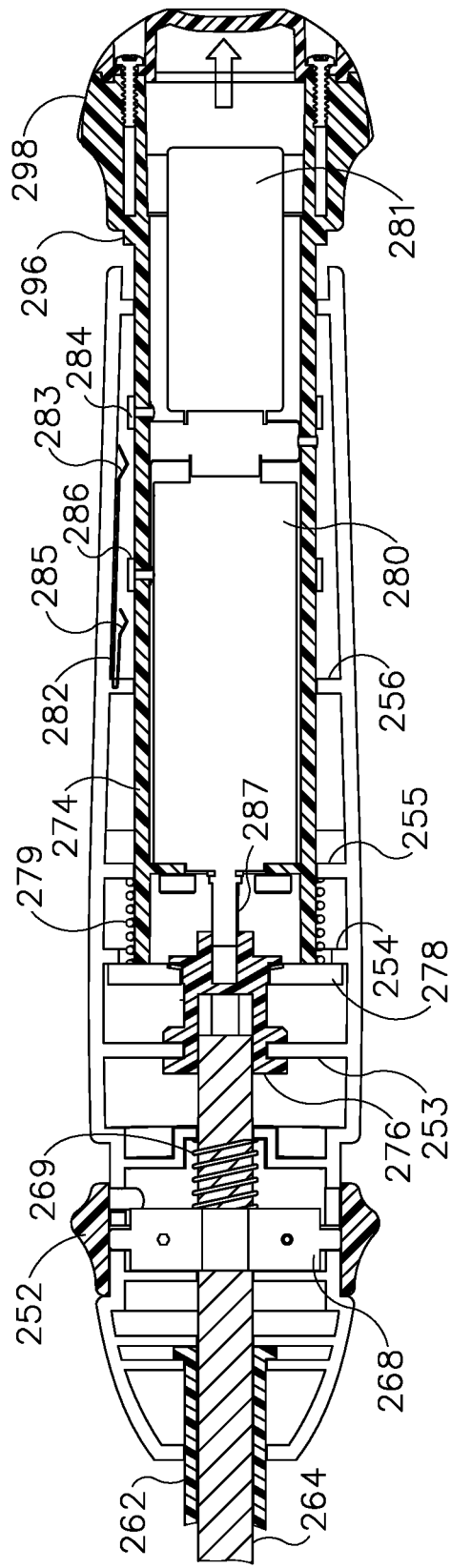
FIG. 16 depicts a cross sectional view of the handle assembly of the instrument of FIG. 7 showing the manual operational mode being selected.

As shown in FIG. 16, instrument (210) is switched from motorized operation to manual operation. A user may grasp rotation knob (298) to translate rotation knob (298) from the distal position to the proximal position. In the proximal position, splines (296) of rotation knob (298) disengage from corresponding teeth (251) in handle housing (272) to allow rotation knob (298) to rotate relative to handle housing (272). This also allows motor housing (274) and first gear (278) to rotate relative to handle housing (272). When rotation knob (298) is in the proximal position, motor housing (274) is also in a proximal position. When motor housing (274) is in the proximal position, spring contacts (283, 285) are offset from annular contacts (284, 286) to decouple battery (281) from motor (280) such that no power is supplied to motor (280). First gear (278) translates proximally to engage splines (275) of second gear (276). Thereby, rotation of rotation knob (298) rotates motor housing (274), first gear (278), second gear (276), and driver actuator (264). A user may also push rotation knob (298) back distally to reselect motorized operation. By using rotation knob (298) as an actuator to select between motorized and manual operation, the need for lockouts or switches to simultaneously remove power to motor (280) is eliminated. Rotation knob (298) thus provides a "bailout" system of motorized operation, while allowing instrument (210) to be fully operational in the manual operational mode. It should therefore be understood that even if an operator initially uses instrument (210) in a motorized mode, the operator may quickly and easily convert instrument (210) to a manually operated mode simply by pulling on rotation knob (298), without sacrificing essential functionality of instrument (210).

3. Manual Operation

Figure 17B:
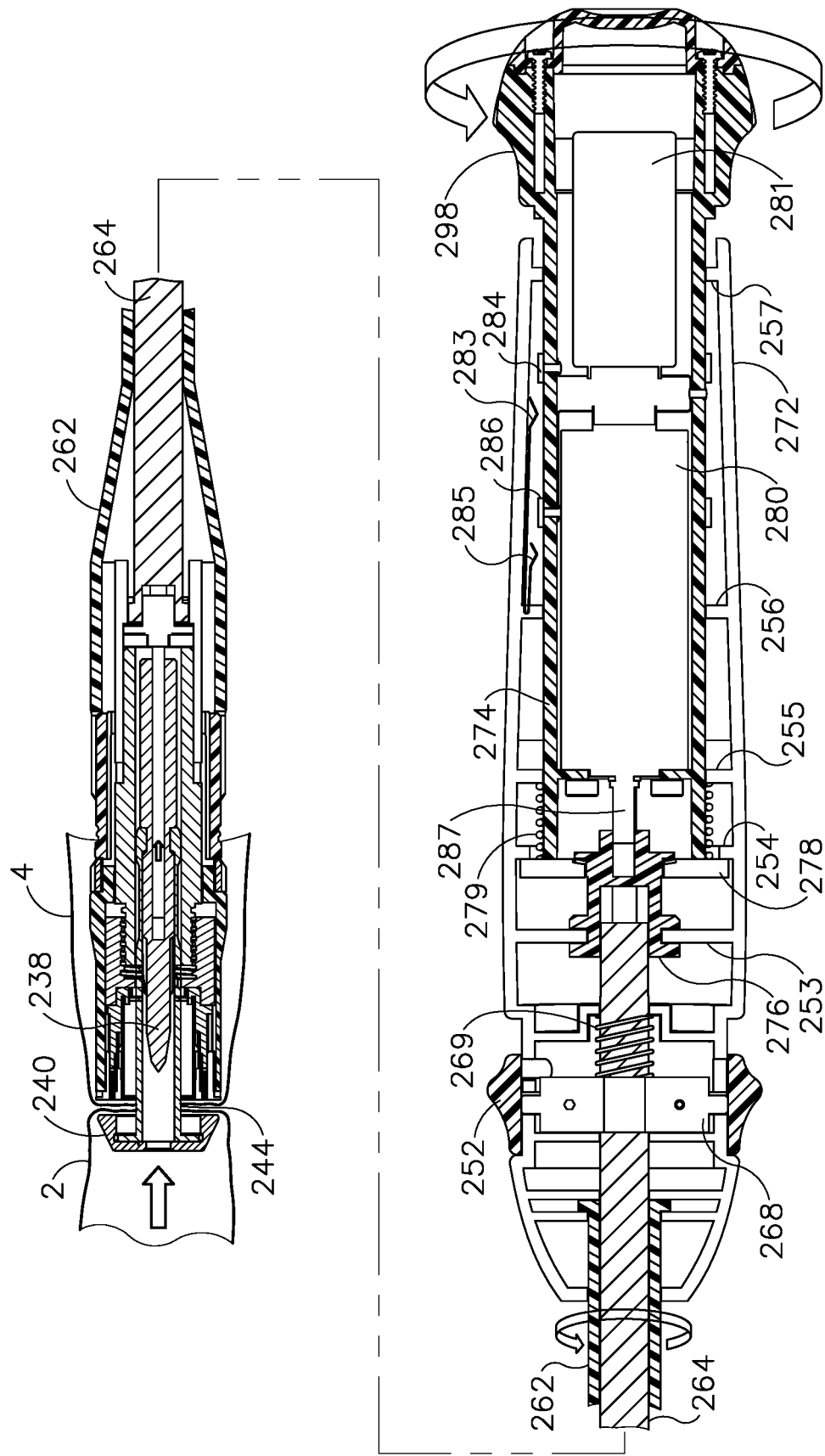
FIG. 17B depicts a cross sectional view of the instrument of FIG. 7, with a manual operational mode selected, in a tissue clamping position.
Figure 17C:
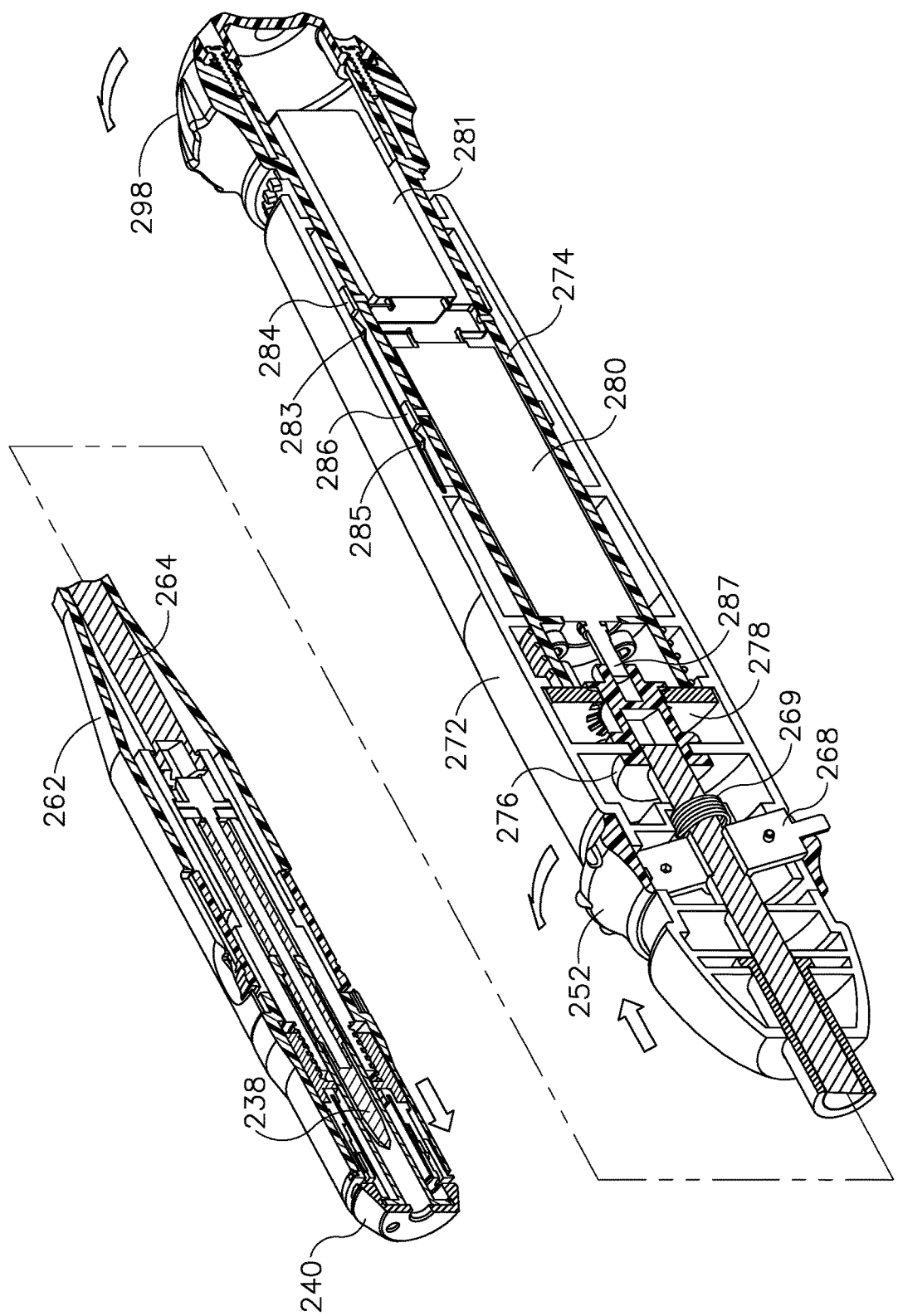
FIG. 17C depicts a cross sectional view of the instrument of FIG. 7, with a manual operational mode selected, in a fired position.

FIGS. 17A-17C show instrument (210) during manual operation. FIG. 17A shows anvil (240) being coupled to trocar (238). Rotation knob (298) is in the proximal position, as described above. As shown in FIG. 17B, rotation knob (298) is rotated to rotate motor housing (274) relative to handle housing (272). Motor housing (274) thereby rotates first gear (278). First gear (278) is engaged with splines (275) to rotate second gear (276). Because second gear (276) is coupled to driver actuator (264), the rotation of second gear (276) also rotates driver actuator (264). This rotation of driver actuator (264) rotates features in stapling head assembly (220) to adjust the gap distance d between anvil (240) and stapling head assembly (220). Once anvil (240) is in a desired position relative to stapling head assembly (220), instrument (210) may be fired, as shown in FIG. 17C. Firing ring (252) is translated from the distal position and out of slot (265) to the proximal position with slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Rotation knob (298) is again rotated with coupling member (268) and driver actuator (264) in the proximal position. This rotation is communicated to driver actuator (264) via first gear (278) and second gear (276), and is thereby communicated to driver actuator (264) to cut and staple tissue (2, 4).

4. Control Assembly

Figure 18:
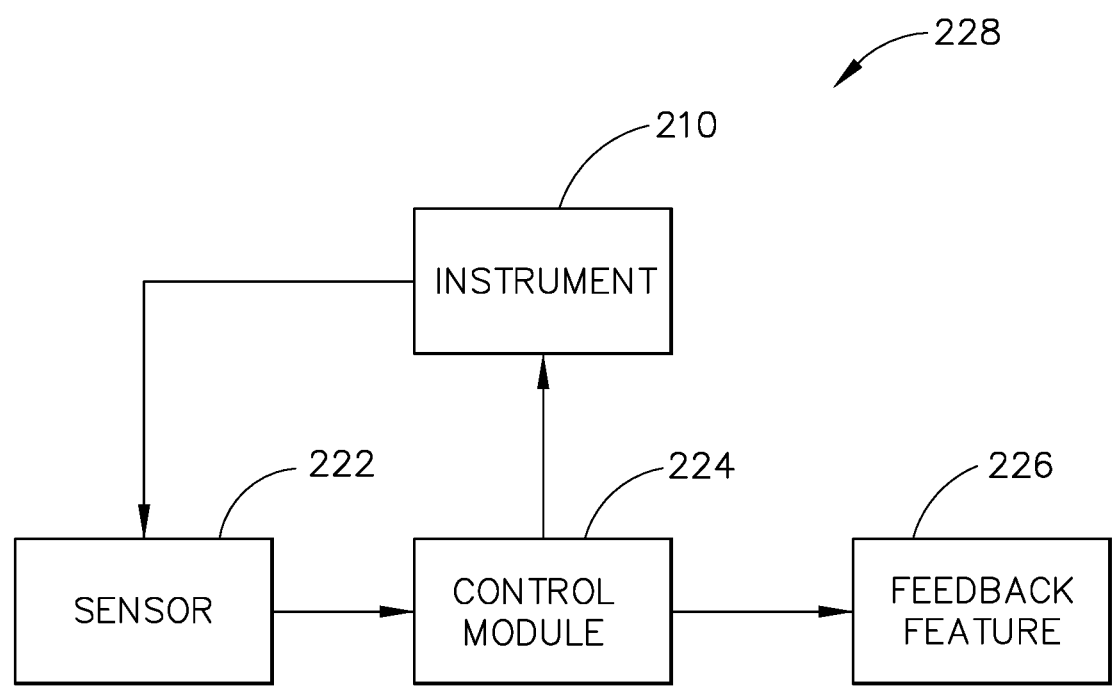
FIG. 18 depicts a schematic of an exemplary control assembly for use with the instrument of FIG. 7.

FIG. 18 shows an exemplary control assembly (228) for use with instrument (210). Control assembly (228) comprises a sensor (222), a control module (224), and a feedback feature (226). Feedback feature (226) may be operable to provide visual, audio, and/or haptic feedback (LED lights, LED display, speaker, vibration generator, etc.). Sensor (222) is coupled to instrument (210) and is configured to detect movement within the drive train of instrument (210). For example, sensor (222) may comprise an encoder positioned to detect rotation of driver actuator (264) or some other rotating component of drive train (e.g, a component that rotates but does not also translate). Sensor (222) is coupled with control module (224) to provide the sensed signal to control module (224). Control module (224) is configured to process the sensed signal and may determine the selected operational mode of instrument (210), the gap distance d between anvil (240) and stapling head assembly (220), and/or the firing of knife (36) and staples (66). In the present example, control module (224) is coupled with instrument (210) and feedback feature (226). However, control module (224) may be coupled with either of instrument (210) or feedback feature (226). Control module (224) may also be coupled with switch (248) to actuate motor (280) when switch (248) is depressed. Each of sensor (222), control module (224), and feedback feature (226) may be located within instrument (210) or remotely from instrument (210).

Based on the sensed signal, control module (224) is operable to actuate instrument (210) and/or feedback feature (226). For example, control module (224) may actuate feedback feature (226) to indicate the selected operational mode of instrument (210). In some versions, feedback feature (226) may have a first LED corresponding to the motorized operational mode and a second LED corresponding to the manual operational mode. Sensor (222) may detect the proximal and/or distal position of rotation knob (298) and/or motor housing (274) and provide the information to control module (224). Control module (224) may then illuminate the first LED if sensor (222) detects the proximal position to indicate the motorized operational mode is selected. Control module (224) may illuminate the second LED if sensor (222) detects the distal position to indicate the manual operational mode is selected. Alternatively, feedback feature (226) may have only one LED which is either illuminated or not to indicate the operational mode, or feedback feature (226) may have a speaker to provide a sound when the operational mode is changed.

In some versions, control module (224) may actuate feedback feature (226) to indicate the selected mode of stapling assembly (220). Feedback feature (226) may have a first LED corresponding to the tissue clamping mode and a second LED corresponding to the firing mode. Sensor (222) may detect the proximal and/or distal position of firing ring (252), coupling member (268) and/or driver actuator (264) and provide the information to control module (224). Control module (224) may then illuminate the first LED if sensor (222) detects the distal position to indicate the tissue clamping mode is selected. Control module (224) may illuminate the second LED if sensor (222) detects the proximal position to indicate the firing mode is selected. Alternatively, feedback feature (226) may have only one LED which is either illuminated or not to indicate stapling head assembly (220) mode, or feedback feature (226) may have a speaker to provide a sound when stapling head assembly (220) mode is changed.

In addition or in the alternative, control module (224) may actuate feedback feature (226) to indicate the gap distance d between anvil (240) and stapling head assembly (220). Sensor (222) may detect the number of rotations of driver actuator (264). Control module (224) may then determine the gap distance d based on the sensed signal and actuate feedback feature (226). Feedback feature (226) may comprise a plurality of LEDs that individually illuminate to indicate the gap distance d. As gap distance d increases, LEDs may illuminate to correspond to the gap distance d. As gap distance d decreases, LEDs may turn off to correspond to the gap distance d. As another merely illustrative example, feedback feature (226) may comprise an LED display screen that provides a real-time indication of the gap distance d. Feedback feature (226) may also have a speaker that emits a sound that changes in either pitch or volume to indicate the corresponding gap distance d. Alternatively, one LED may be used to indicate when a particular gap distance d has been reached, or a sound may be provided when the particular gap distance d has been reached.

In versions where feedback feature (226) includes the capability of providing haptic feedback to the operator, it should be understood that various conventional components may be incorporated into handle assembly (270) to provide such haptic feedback. It should also be understood that haptic feedback may be provided through motor (280). By way of example only, feedback feature (226) may be configured to provide a sine wave signal to motor (280) to essentially rotate drive shaft (287) slightly clockwise and then immediately rotating it slightly counterclockwise the exact same amount. The net result would be zero rotational displacement of drive shaft (287). When this sequence is repeated (e.g., in a rapid succession), the movement of drive shaft (287) may cause handle assembly (270) to vibrate or otherwise shake enough for the operator to feel it through the hand that grasps handle assembly (270). With the zero net movement of drive shaft (287) through this feedback algorithm, the haptic feedback may result in no net actuation of anything in head assembly (220), regardless of whether driver actuator (264) is in the distal position or the proximal position. Such haptic feedback may be provided to indicate the end of a stapling stroke, to indicate a lockout condition, and/or to indicate some other condition. Various other suitable ways in which audio, visual, and/or haptic feedback may be provided will be apparent to those of ordinary skill in the art in view of the teachings herein.

In some versions, control module (224) may actuate instrument (210). Sensor (222) may be configured to detect when knife (36) and staples (66) have been fired. Control module (224) may thus automatically reverse motor (280) once knife (36) and staples (66) have been fired. Control module (224) may also actuate feedback feature (226) to indicate to a user that instrument (210) has been fired. Other suitable ways in which sensors (222), control module (224), and feedback feature (226) may be used will be apparent to those of ordinary skill in the art in view of the teachings herein. It should also be understood that such features may be simply omitted if desired.

B. Exemplary Switch Assembly

Figure 19:
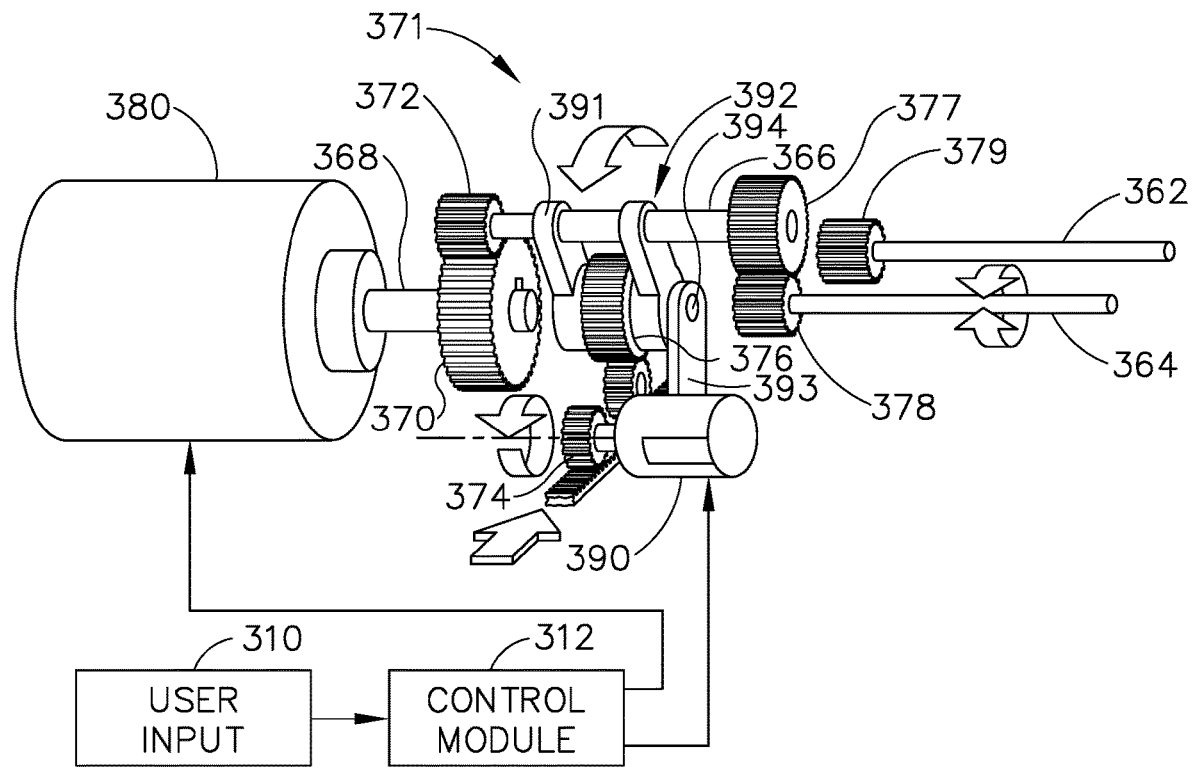
FIG. 19 depicts a partial perspective view of another exemplary operational mode selection assembly.
Figure 20:
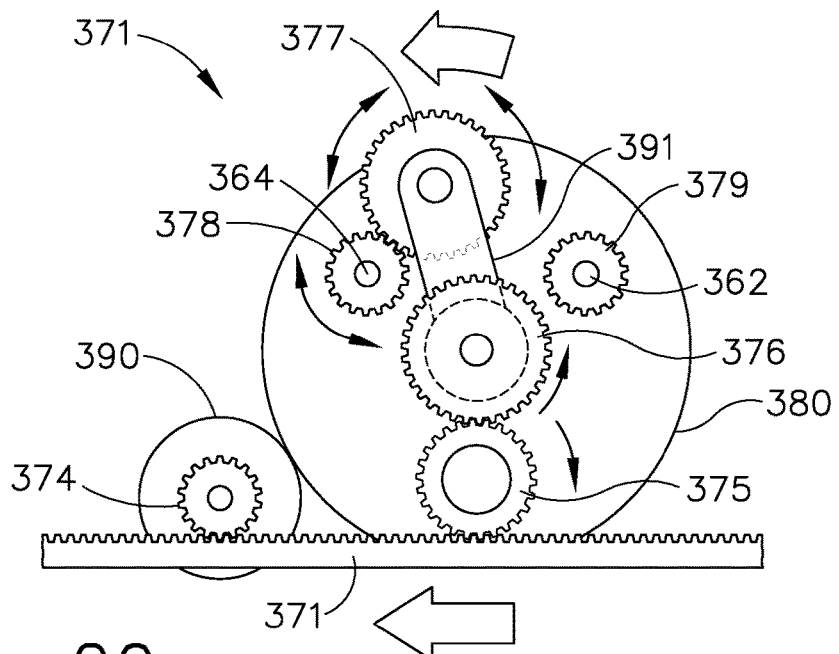
FIG. 20 depicts a front view of the operational mode selection assembly of FIG. 19.

As described above, surgical stapling instrument (10, 210) has two sub-systems, a closure sub-system (to clamp tissue between anvil (40, 240) and stapling head assembly (20, 220)) and a firing sub-system (to drive knife (36) and staples (66) distally toward anvil (40, 240)), in order to create an anastomosis. It may be desirable to power both sub-systems with a single rotary motor to eliminate the cost and packaging of an additional motor and transmission. FIGS. 19-20 show an exemplary drive assembly (371) configured to power two sub-systems with a single rotary motor (380). While instrument (210) provided closure and firing with a single rotary drive shaft, drive assembly (371) of this example provides closure and firing through two separate rotary drive shafts driven by a single motor (380). Drive assembly (371) comprises a motor (380), a transmission shaft (392), a solenoid (390), a closure rod (364), and a firing rod (362). Motor (380) comprises a shaft (368) extending from motor (380) and a gear (370) coupled to shaft (368). Transmission shaft (392) comprises a gear (372) engaged with gear (370) of motor (380). A gear (377) is positioned on the opposing end of transmission shaft (392).

A pivoting swing arm (391) is wrapped around transmission shaft (392) such that transmission shaft (392) may freely rotate relative to swing arm (391), as shown in FIG. 18. Swing arm (391) extends from transmission shaft (392) and comprises a gear (376). Gear (376) is fixedly secured to swing arm (391). A pin (394) extends from swing arm (391) and is coaxial with gear (376). Pin (394) is pivotally supported by a bracket (393), such that swing arm (391) is pivotable about pin (394) relative to bracket (393) in response to rotation of gear (376). Solenoid (390) comprises a gear (374) coupled to a rack (371). Rack (371) is also coupled to a gear (375), which engages gear (376) of swing arm (391). Alternatively, gear (374) of solenoid (390) may directly couple to gear (376) of swing arm (391). Closure rod (364) comprises a gear (378). Firing rod (362) is positioned adjacent to and substantially parallel with closure rod (364). Firing rod (362) comprises a gear (379). Gear (377) of transmission shaft (392) selectively swings to engage either gear (378) of closure rod (364) or gear (379) of firing rod (362).

As shown in FIGS. 19-20, transmission shaft (392) is positioned to engage closure rod (364). Accordingly, when motor (380) is activated, shaft (368) rotates gear (370). Gear (370) thereby rotates gear (372) and transmission shaft (392) to rotate gear (377). Because gear (377) is engaged with gear (378), transmission shaft (392) thereby rotates closure rod (364). Closure rod (364) may be used to adjust the gap distance d between anvil (40, 240) and stapling head assembly (20, 220). If a user desires to switch to the firing sub-system, solenoid (390) may be actuated. When solenoid (390) is actuated, solenoid (390) rotates gear (374) to translate rack (371). Rack (371) then rotates gear (375) and gear (376) of swing arm (391). Gear (376) thereby pivots swing arm (391). As swing arm (391) pivots, swing arm (391) translates transmission shaft (392) such that transmission shaft (392) disengages closure rod (364) and engages firing rod (362). Accordingly, when motor (380) is activated, shaft (368) rotates gear (370). Gear (370) thereby rotates gear (372) and transmission shaft (392) to rotate gear (377). Because gear (377) is now engaged with gear (379), transmission shaft (392) thereby rotates firing rod (362). Firing rod (364) may be used to drive knife (36) and staples (66) distally toward anvil (40, 240). Solenoid (390) may then be actuated again such that switch assembly (371) switches to the closure sub-system via swing arm (391).

Solenoid (390) may be button activated or be otherwise manually activated. Alternatively, switching assembly (371) may incorporate logic such that solenoid (390) is activated automatically. For instance, a user may actuate drive assembly (371) by inputting a user input (310) into a control module (312), as shown in FIG. 19. Control module (312) is coupled to motor (380) and solenoid (390) to selectively actuate motor (380) and/or solenoid (390) based on user input (310). Control module (312) may be integral with instrument (10, 210), or control module (312) may be a separate assembly. Suitable control module (312) configurations will be apparent to one with ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein. Various suitable ways in which such teachings may be combined will be apparent to those of ordinary skill in the art.

As described in U.S. Pat. No. 7,794,475, FIGS. 21-22 depict a unique and novel collapsible or compressible staple driver arrangement that enables the various staple drivers to accommodate different tissue thicknesses by collapsing or compressing in response to compression forces that the driver encounters during the firing process. As used herein, the term "firing process" refers to the process of driving the staple drivers towards the staple forming undersurface of the anvil. As was mentioned above, prior staple drivers were fabricated from stiff/rigid material designed to resist deflection and deformation when encountering compression forces during the firing process. A variety of such driver configurations are known. For example, some staple drivers are configured to support a single staple and others are designed to support multiple staples. A discussion of single and double staple drivers and how they may be operably supported and fired within a staple cartridge is found in U.S. patent application Ser. No. 11/216,562, filed Aug. 31, 2005, issued as U.S. Pat. No. 7,669,746 on Mar. 2, 2010, entitled Staple Cartridges For Forming Staples Having Differing Formed Staple Heights to Frederick E. Shelton, IV, the disclosure of which is herein incorporated by reference.

FIG. 21 depicts a staple applying assembly (916h) that includes an elongate channel (940h) that has an anvil (920h) pivotally coupled thereto in a known manner. The elongate channel (940h) is configured to operably support a staple cartridge (942h) therein. The anvil (920h) has a staple forming undersurface (960h) thereon that is adapted to confront the upper surface (943h) of the staple cartridge (942h) when the anvil (920h) is pivoted to the closed position shown in FIG. 21. The staples (983) are each supported on a corresponding staple driver (500), the construction of which will be discussed in further detail below.

Each staple driver (500) may be movably supported within a corresponding staple channel (987h) provided in the cartridge body (985h) as shown in FIGS. 21 and 22. Also operably supported within the cartridge body (985h) is a driving member or wedge sled (978) that is oriented for engagement by the E-beam firing member (950) during the firing process. As the E-beam firing member (950) and wedge sled (978) are driven distally through the elongate channel (940h) and staple cartridge (942) in a known manner, the wedge sled (978) drives the staple drivers (500) upwardly within the cartridge body (985h). As the staple drivers (500) are driven upwardly toward the staple forming undersurface (960h) of the anvil (920h), they carry with them their respective staple (983) or staples which are driven into forming engagement with the corresponding staple forming pockets (961h) in the staple forming undersurface (960h) of the anvil (920h). As the ends (988) of the staple (983) contact the forming pockets (961h), they are bent over thus providing the staple (983) with a shape that somewhat resembles a "B". While the various embodiments of the present invention have been described herein in connection with E-beam firing members, it is conceivable that these various embodiments may also be successfully employed with a variety of different firing member and driving member arrangements without departing from the spirit and scope of the present invention.

One collapsible staple driver embodiment of the present invention is depicted in FIGS. 21 and 22. As can be seen in those Figures, the collapsible or compressible staple driver (500) includes a base portion (502) and a staple supporting portion (520) that is movable from a first uncollapsed position relative to the base portion (502) in response to compression forces generated during the firing process. In various embodiments, the base portion (502) may have a forward support column segment and a rearward support column segment that is spaced from the forward support column segment and is substantially integrally formed therewith. The base portion (502) may also have an upstanding side portion that has a rib protruding from a backside therefrom. The upstanding side portion serves to define a receiving ledge (514) in the base portion (502) for receiving the staple supporting portion (520) thereon. Those of ordinary skill in the art will understand that when the staple supporting portion (520) is received on the ledge (514), the staple driver (500) is unable to collapse or compress any further.

The staple supporting portion (520) of the staple driver (500) may similarly include a forward support column segment and rearward support column segment that is spaced from the forward support column segment. When the staple supporting portion (520) is received on the base portion (502), the forward support column segments serve to form a forward column portion and the reward column segments form a rearward column portion. A forward staple receiving groove (526) is formed in the forward support column segment and a rearward staple receiving groove (528) is formed in the rearward support column segment. The forward staple receiving groove (526) and the rearward staple receiving groove (528) serve to support a staple (983) therein as illustrated in FIG. 22. The rib and the forward column and rearward column may cooperate with corresponding channels (not shown) in the staple cartridge body (985) to provide lateral support to the staple driver (500) while permitting the driver to be driven upward within the cartridge body (985) during the firing process.

In various embodiments, a resistive attachment structure is provided to support the staple supporting portion (520) in a first uncompressed or uncollapsed orientation relative to the base portion prior to encountering any compressive forces during the firing operation and to permit the staple supporting portion (520) and the base portion to move towards each other (collapse or compress) in response to the magnitude of the compression forces applied to the staple supporting portion (520) and base portion (520) during the staple firing operation. As can be seen in FIGS. 21 and 22, the resistive attachment structure in various embodiments may comprise a pair of attachment rods (540) that protrude from the bottom of the staple supporting portion (520) and correspond to holes or apertures (542) in the base portion (502). The rods (540) are sized and shaped relative to the holes (542) to establish an interference fit or "light press fit" (i.e., an interference of approximately 0.001 inches) therebetween such that when the staple supporting portion (520) and base driver portion (502) are compressed together during the staple firing operation as will be discussed in further detail below, the staple supporting portion (520) and the base portion (502) can compress toward each other to reduce the overall height of the staple driver (500) in relation to the amount of compression force encountered during the firing process. In various embodiments, for example, the staple supporting portion (520) and base portion (520) may be fabricated from the same material such as, for example, plastic material such as ULTEM®. In other embodiments, the base portion (502) and the staple supporting portion (520) may be fabricated from different materials. For example, staple supporting portion (520) may be fabricated from ULTEM® and base portion (502) may be fabricated from glass or mineral filled ULTEM®. However, other materials could also be employed. For example, the base portion (502) could be fabricated from Nylon 6/6 or Nylon 6/12.

In various embodiments, a frictional or an interference fit of approximately 0.001 inch may be established between the attachment rods (540) and their corresponding holes (542). However, other degrees of interference fit may be employed to attain the desired amount and rate of driver compression in proportion to the magnitude of compression forces encountered when stapling a particular type/thickness of tissue. For example, in one embodiment, the degree of interference fit between the attachment rods (540) and their respective holes (542) may be approximately 0.002 to 0.005 inches for stapling tissues wherein it is anticipated that compression forces on the order of 2-5 pounds may be generated during the firing operation.

FIG. 22 illustrates various ranges of travel and compression that the staple drivers (500) may experience when encountering tissues of varying thicknesses. More specifically, FIG. 22 illustrates a portion of tissue (560) clamped between the upper surface (943h) of the staple cartridge (942h) and the staple forming undersurface (960h) of the anvil (920h). As illustrated in FIG. 22, the tissue (560) has three thicknesses. The thickest portion of tissue is designated as (562) and comprises the portion of tissue that is on the right side of the Figure. The next thickness portion of tissue is designated as (564) and the thinnest portion of tissue (560) is designated as (566) and is on the left side of the Figure. For the purposes of this explanation, the staple driver associated with tissue portion (562) is designated as staple driver (500a). The staple driver associated with tissue portion (564) is designated as staple driver (500b) and the staple driver associated with tissue portion (566) is designated as (500c). It will be understood that staple drivers (500a, 500b, 500c), may be identical in construction to staple driver (500) as described above.

Turning to staple driver (500a) first, as the staple driver (500a) is driven upwardly towards the staple forming undersurface (960h) of the anvil (920h) by the wedge sled (not shown in FIG. 22), it encounters the thick tissue portion (562) which resists the upward movement of the staple driver (500a). Such resistive force (represented by arrow 570) opposes the drive force (represented by arrow 572) generated by the wedge sled and serves to overcome the amount of interference established between the attachment rods (540) and their respective holes (542) and forces the rods (540) deeper into their respective holes (542) to thereby permit the staple supporting portion (520a) of the staple driver (500a) and base portion (502a) to move toward each other. This movement of the staple supporting portion (520a) and base portion (502a) towards each other under a compressive force generated during the staple firing operation is referred to herein as "collapsing" or "compressing". When in the completely compressed position wherein the staple supporting portion (520a) is received on the ledge (514a) of the base portion (502a), the staple supporting ledges (526a, 528a) on the staple supporting portion (520a) may preferably support the bottom cross member (989) of the staple (983) above the upper surface (943h) of the staple cartridge (942h) to avoid catching the staple (983) on the staple cartridge (942h) when the staple applying assembly (16h) is withdrawn. The compressed height of the staple driver (500a) is designated by arrow 574 in FIG. 22.

Turning next to staple driver (500b) which corresponds to tissue portion (564), because the tissue portion (564) is not as thick as tissue portion (562), the resistive force (570b) encountered by the staple driver (500b) during the firing operation is not as great as resistive force (570). Therefore, the attachment pins (540b) of staple driver (500b) are not advanced into their respective holes (542b) as far as the pins (540) of staple driver (500a) were advanced into their respective holes (542). Thus, the compressed height (576) of staple driver (500b) is greater than the compressed height (574) of staple driver (500a). As can also be seen in FIG. 22, the bottom portion (989) of the staple (983) supported in staple driver (500b) is supported above the upper surface (943h) of the staple cartridge (942h).

Staple driver (500c) is associated with the thinnest tissue portion (566). Thus, the resistive force (570c) encountered by the staple driver (500c) during the staple firing operation is less than the resistive force (570b) that was encountered by staple driver (500b). Thus, the pins (540c) of staple driver (500c) are not advanced into their respective holes (542c) as far as the pins (540b) of staple driver (500b) were advanced into their respective holes (542b). Thus, the compressed height (578) of staple driver (500c) is greater than the compressed height (576) of staple driver (500b).

As can be further seen in FIG. 22, because the compressed height (578) of staple driver (500c) is greater than the compressed height (576) of staple driver (500b), the staple (983c) supported by staple driver (500c) was compressed to a greater extent than the staple (983b) that was supported by staple driver (500b). Thus, the formed height of staple (983c) is less than the formed height of staple (983b) which is less than the formed height of staple (983a) as illustrated in FIG. 22.

Those of ordinary skill in the art will appreciate that the number, shape, composition and size of the attachment rods and their respective holes can vary from embodiment to embodiment without departing from the spirit and scope of the present invention. Such interrelationship between the attachment rods and their respective holes serves to establish an amount of frictional interference therebetween which can be overcome in relation to various compression forces encountered when clamping/stapling different thicknesses of tissue. In an alternative version, the attachment to rods (540) may be formed on the base portion (502) and the holes provided in the staple supporting portion (520).

FIGS. 23-24 illustrate another unique and novel endocutter implement portion of various embodiments of the present invention that includes an elongate channel and an anvil arrangement (1050e) that are "self adjusting" with respect to tissue thickness. In various embodiments, the proximal end of the anvil (1050e) is pivotally attached to the proximal end of the elongate channel by mounting members which may comprise trunnions movably received in corresponding elongate slots formed in the proximal end of the elongate channel. FIG. 23 also illustrates the position of the anvil (1050e) relative to the staple cartridge (942) and tissue (1092) that has a thickness "t". FIG. 24 also illustrates the anvil (1050e) relative to the staple cartridge (942) and tissue (1094) that has a thickness "T". As can be seen in FIGS. 23 and 24, the staples (983) in the thinner tissue (1092) are more tightly formed than the staples (983) extending through the thicker tissue (1094).

Figure 25:
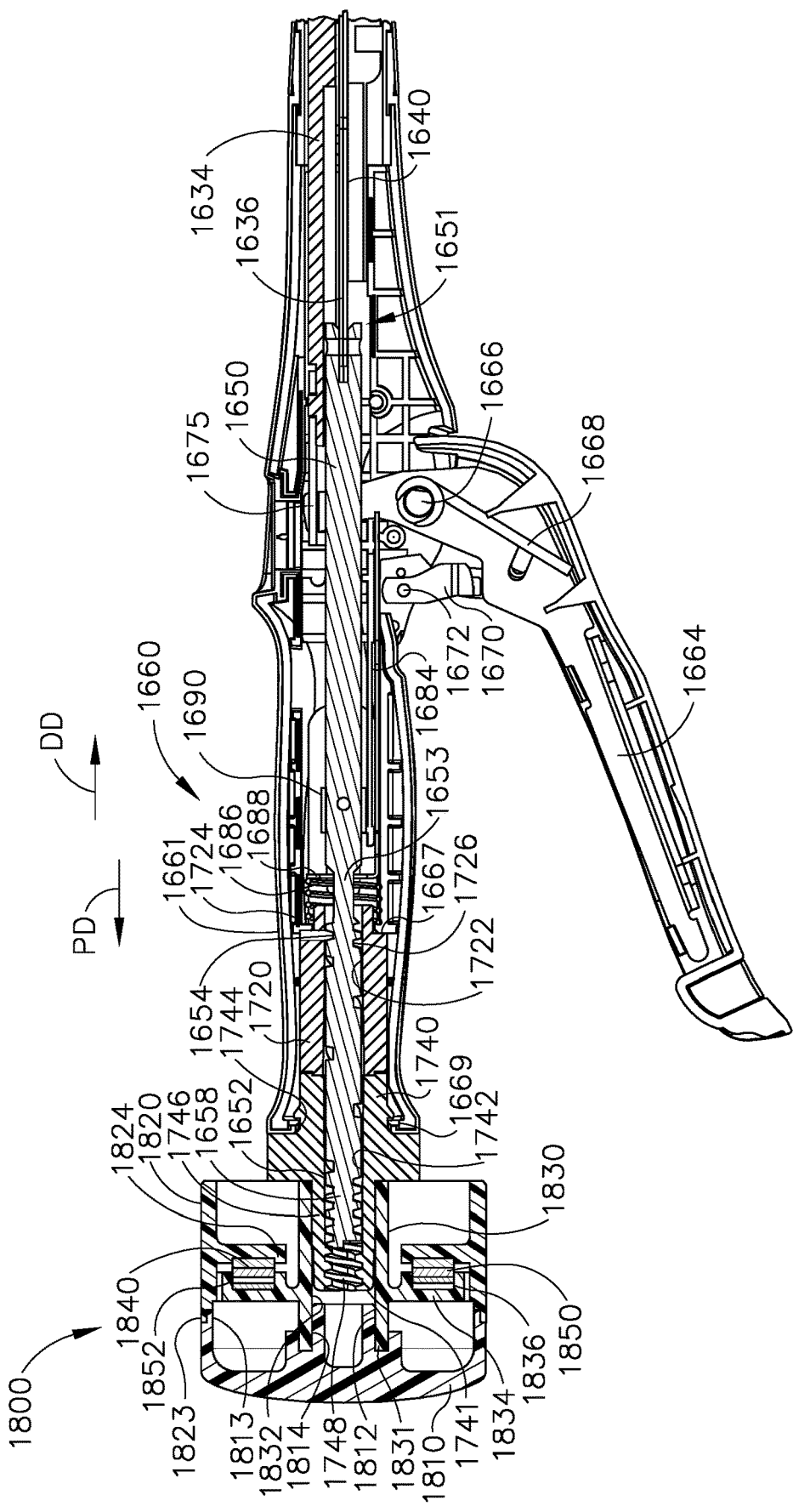
FIG. 25 is a cross-sectional view of the handle assembly and closure knob assembly of various embodiments of the present invention.
Figure 26:
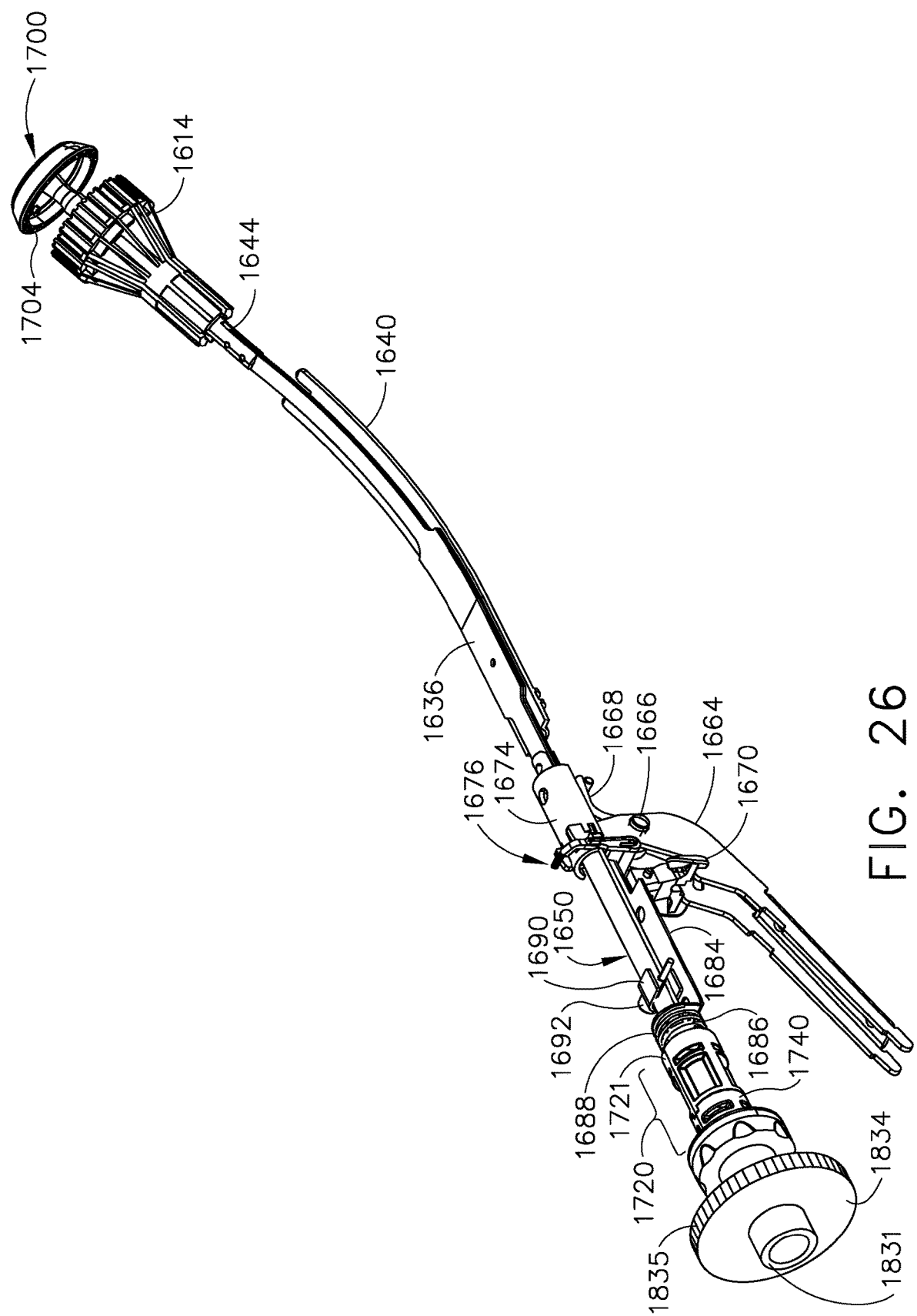
FIG. 26 is a perspective view of the shaft assembly, trigger assembly, staple driver, anvil and closure knob assembly with the handle housing, head casing and outer tubular shroud removed therefrom.

As can be seen in FIG. 25, the adjustment shaft (1650) has a distal portion (1651) that is attached to the top and bottom tension bands (1636, 1638) and a proximal portion (1652) that is adjoined to the distal portion (1651) by a reduced diameter segment (1653). The proximal portion (1652) is axially received within an axial passage (1722) in the distal closure nut (1720) that is keyed onto or otherwise attached to a proximal closure nut (1740) to form a closure nut assembly generally designated as (1721) such that the distal closure nut (1720) and the proximal closure nut (1740) may rotate together. The distal closure nut (1720) may further have a distally extending hub portion (1724) that abuts an inwardly extending retainer flange (1667) formed inside the handle assembly (1660). Such arrangement permits the distal closure nut (1720) to freely rotate within the handle assembly (1660), but is unable to move axially therewithin. Likewise, the proximal end portion (1652) of the adjustment shaft (1650) is axially received within an axial passage (1742) within the proximal closure nut (1740). A circumferentially extending groove (1744) may be provided in the outer surface of the proximal closure nut (1740) for receiving an inwardly protruding proximal retainer flange (1669) formed on the proximal end of the handle assembly (1660). Such arrangement serves to permit the proximal closure nut (1740) to freely rotate relative to the handle assembly (1660).

Also in various embodiments, the closure knob assembly (1800) is attached to the proximal end (1741) of the proximal closure nut (1740). In one embodiment for example, the proximal end (1741) of the proximal closure nut (1740) may be formed with a proximally extending tapered hub portion (1746) that is adapted to be nonrotatably received in an axial passage (1832) in a clutch hub portion (1830). The tapered hub portion (1746) also be formed with a key or spline arrangement to non-rotatably affix the hub portion (1746) with the clutch hub portion (1830). Other fastener arrangements and methods may be employed to non-movably attach the hub portion (1746) of the proximal closure nut (1740) to the clutch hub portion (1830). Thus, rotation of the clutch hub portion (1830) will cause the proximal closure nut (1740) and distal closure nut (1720) to also rotate.

As can also be seen in FIGS. 25, 27, and 28, the knob assembly (1800) may further include a proximal cap portion (1810) and a distal cap portion (1820). The proximal end (1831) of the clutch hub portion may be received in a circular slot (1814) formed in a distal end of the proximal cap portion (1810). The slot (1814) may be sized to permit the proximal cap portion (1810) to rotate about the proximal end (1831) of the clutch hub portion (1830). In addition, the proximal cap portion (1810) may have a protrusion (1812) that rotatably extends into the axial passage (1832) in the clutch hub portion (1830). Also in various embodiments, the closure knob assembly (1800) may comprise a distal cap portion (1820) that is rigidly and non-rotatably coupled to the proximal cap portion (1810). Those of ordinary skill in the art will understand that the closure knob assembly (1800) may be fabricated in multiple parts for ease of assembly of various components of the instrument. In various embodiments, the mating ends of the proximal cap portion (1810) and distal cap portion (1820) may be configured with complementary flanged portions (1813, 1823), respectively as shown in FIGS. 25 and 27, that are interconnected by adhesive, welding, etc. or other fastener arrangements may be employed. Thus, when fastened together, the proximal cap portion (1810) and the distal cap portion (1820) rotate together as a unit.

As can further be seen in FIGS. 25 and 27, various embodiments may comprise a slip clutch assembly generally designated as (1821). The slip clutch assembly (1821) may take various forms that are supported by or are integrally formed in the adjustment knob assembly (1800). In one embodiment, for example, the distal cap portion (1820) may be provided with an inwardly extending cap flange (1824) that is in confronting orientation with an outwardly extending clutch flange (1834) formed on the clutch hub portion (1830). A first friction pad (1840) is non-rotatably affixed to the inwardly extending cap flange (1824). A pad cavity (1836) may be formed within the clutch flange (1834) for movably receiving a second friction pad (1850) and a wave spring (1852) therein. The second friction pad (1850) may be provided with splines or keys (not shown) to prevent rotation thereof in the cavity (1836), but facilitate some axial travel thereof within the cavity (1836). In various embodiments, the first and second friction pads (1840, 1850) may be fabricated from, for example, liquid crystal polymer, Nylon, ULTEM®, polycarbonate, aluminum, etc.

In various embodiments, the proximal portion (1652) of the adjustment shaft (1650) has a low pitch thread segment (1654) formed therein that communicates with a higher pitched threaded segment (1657). As can be seen in FIG. 25, a drive pin (1726) protrudes inwardly into the axial passage (1722) for "driving" engagement with the threaded segments (1654, 1657) in the adjustment shaft (1650). In addition, the proximal end (1652) of the adjustment shaft (1650) has a threaded section (1658) adapted for threaded engagement with a threaded cavity (1748) in the tapered hub portion (1746) of the proximal closure nut (1740). In various embodiments, the drive pin (1726) is oriented in the distal closure nut (1720) such that when the drive pin (1726) is still engaged with the low pitched distal thread segment (1654) of the adjustment shaft (1650), the threaded end (1658) of the adjustment shaft (1650) has sufficiently threadedly engaged the threaded cavity (1748) in the tapered hub portion (1746) of the proximal closure nut (1740) for threaded travel therein as the closure knob assembly (1800) is rotated. In particular, as the closure knob assembly (1800) is rotated in the counterclockwise ("CC") direction, the adjustment shaft (1650) is moved in the distal direction ("DD") by virtue of the engagement of the drive pin (1726) with the threaded segments (1654 and 1657) formed in the attachment rod (1650). Those of ordinary skill in the art will appreciate that rotation of the distal closure nut (1720) when the drive pin (1726) is engaged with the distal threaded segment (1654) will result in fastener axial movement of the adjustment shaft (1650) than when the drive rod (1726) is engaged with the threaded segment (1567) which has a larger pitch than the threaded segment (1564). Axial movement of the adjustment shaft (1650) moves the top and bottom tension bands (1636, 1638), the trocar tip (1644) and the anvil (1700) (when attached to the trocar tip (1644) in the distal ("DD") direction away from the head (1610).

To close the anvil (1700) or move it toward the head (1610) and staple cartridge (1616) supported therein in the ("PD") direction, the surgeon begins to turn the closure knob assembly (1800) in the clockwise ("CW") direction. The frictional forces generated between the first and second friction pads (1840, 1850) serves to retain the closure knob assembly (1800) in frictional engagement with the clutch hub (1830) which is non-rotatably attached to the proximal closure nut (1740). Because the proximal closure nut (1740) is non-rotatably affixed to the distal closure nut (1720), the distal closure nut (1720) is also rotated in the clockwise direction. Rotation of the distal closure nut (1720) results in the driving engagement of the drive pin (1726) with either of the thread segments (1654, 1657) (depending upon the position of the adjustment shaft (1650) relative thereto) and causes the adjustment shaft (1650) to be drawn in the proximal direction ("PD"). As the adjustment shaft (1650) is drawn in the proximal direction, the threaded end (1658) of the adjustment shaft (1650) threadably engages the threaded cavity (1748) of the tapered threaded hub portion (1746) of the proximal closure nut (1740) and reduced diameter segment (1653) moves adjacent to the drive pin such that the drive pin is no longer in driving engagement with the adjustment shaft (1650). Now, the threaded end (1652) is in full threaded engagement with the threaded hole (1748) in the proximal closure nut (1740). Further rotation of the closure knob assembly (1800) in the clockwise direction continues to draw the adjustment shaft (1650) in the proximal direction ("PD"). As the adjustment shaft (1650) is drawn in the proximal direction, the anvil (1700) is moved towards the cartridge (1616) supported in the staple driver assembly (1614) to clamp an amount of tissue therebetween. As the anvil (1700) continues to move toward the staple cartridge (1616), the tissue is compressed therebetween and resists further travel of the anvil (1700) in the proximal direction.

In various embodiments, to prevent the tissue from being over compressed which could result in damaging or killing the tissue to be stapled, the composition of the first and second friction pads (1840, 1850) and the size of the spring (1852) are selected such that when a predetermined amount of tissue compression is attained, the friction pads (1840, 1850) begin to slip to prevent further rotation of the closure knob assembly (1800) from being transferred to the clutch hub (1830). Thus, even if the surgeon continues to rotate the closure knob assembly (1800) after the tissue has been adequately compressed, such further rotation will not result in continued movement of the adjustment shaft (1650) (and anvil (1700)) in the proximal direction to avoid over compressing the tissue. For example, in various embodiments, the instrument may be constructed such that the maximum amount of compression forces that may be applied to the tissue between the anvil (1700) and the cartridge (1616) may be approximately 150 pounds per square inch. For such applications, the first and second friction pads (1840, 1850) and the wave spring (1852) may be so configured to permit slippage between the first and second friction pads (1840, 1850) if the closure knob assembly (1800) continues to be rotated after that maximum amount of compression force has been attained. In such example, the rotation of the closure knob assembly (1800) may generate an approximate amount of torque of, for example, 15 inch pounds which overcomes the frictional forces that are established when the maximum amount of desirable compression has been attained (which serves to retain the first and second friction pads (1840, 1850) in frictional engagement with each other) and permit the desired slippage between the first and second friction pads. In various embodiments, to ensure that the adjustment shaft (1650) is moved distally when the closure knob assembly (1800) is rotated in a counterclockwise direction, a series of circumferentially extending ratchet teeth (1816) may be formed in the interior of the closure knob assembly (1800) for engagement with circumferentially extending engagement teeth (1835) formed on the circumference of the clutch flange (1834). See FIGS. 27 and 28. The teeth (1816, 1835) may be configured such that when the closure knob assembly (1800) is rotated in the clockwise direction to move the anvil (1700) toward the cartridge (1616), the teeth (1816) on the closure knob assembly (1800) slip over the teeth (1835) formed on the clutch flange (1834). However, when the closure knob assembly (1800) is rotated in the counterclockwise direction, the teeth (1816) engage teeth (1845) on the clutch flange (1834) to cause the clutch hub (1830) and the proximal and distal closure nuts (1720, 1740) to rotate therewith to move the anvil (1700) away from the cartridge (1616).

As indicated above, various embodiments may be provided with a safety yoke (1670) that prevents actuation of the trigger assembly (1664) when the safety yoke (1670) is in a "safe" or engaged position. In various embodiments, a safety spring (1686) may be journaled on the adjustment shaft (1650) and be received on the hub portion (1724) of the distal closure nut (1720). The spring (1686) may be oriented between the distal closure nut (1720) and an upstanding end wall portion (1688) of the safety release (1684). See FIG. 25. The safety spring (1686) serves to bias the safety release (1684) in the distal direction and into contact with the safety yoke (1670) to prevent the safety yoke from being pivoted to an off position wherein the trigger (1664) may be actuated. Also in these variations, a rod clip (1690) may be attached to the adjustment shaft (1650) by and adjusting screw (1692) that extends through a slot (not shown) in the rod clip (1690). The rod clip (1690) may be so located on the adjustment shaft (1650) such that when the adjustment shaft (1650) has been axially positioned in its most proximal position which results in the maximum amount of desirable compression being applied to the tissue or in a position wherein the anvil (1700) has begun to clamp the tissue, but has not yet attained the predetermined maximum amount of compression force, the rod clip (1690) has contacted the upstanding end wall (1688) and moved it proximally a sufficient distance to move the distal end (1685) of the safety release (1684) out of retaining engagement with the safety yoke (1670). The surgeon may then pivot the safety yoke (1670) to the off position thereby enabling the trigger (1664) to be depressed.

Figure 29:
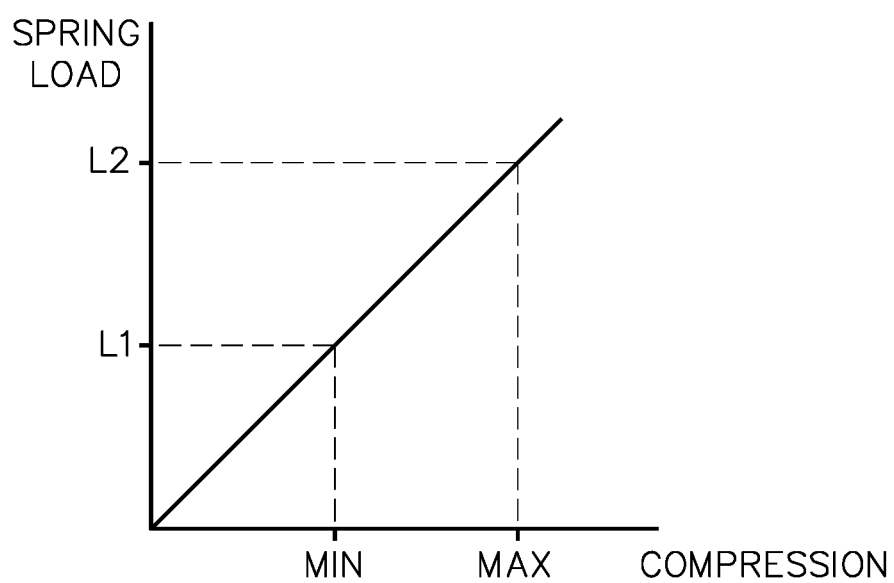
FIG. 29 is a graph illustrating the relationship between a compression force and resistive load generated by a variable force generator that may be used in connection with various embodiments of the present invention.

In various embodiments, the amount of spring load ("L1") necessary to attain a minimum amount of tissue compression ("Min") may be determined as well as the amount of spring load "(L2") required to attain a maximum amount of tissue compression ("Max") may also be determined. In addition, the distance "D1" that the proximal cap portion must be rotated from the neutral position to generate spring load L1 and the distance "D2" that the proximal cap portion must be rotated to generate spring load "L2" may be determined. The graph depicted in FIG. 29 illustrates an example of a relationship between these parameters. Those of ordinary skill in the art will appreciate that such relationships may change depending upon the spring used and various other factors such as, for example, frictional forces encountered by the moving components of the device.

Similarly, at least some of the teachings herein may be readily combined with one or more teachings of U.S. patent application Ser. No. 13/693,430, entitled "Trans-Oral Circular Anvil Introduction System with Dilation Feature," filed Dec. 4, 2012, now U.S. Pat. No. 9,572,573, issued Feb. 21, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,951, entitled "Surgical Staple with Integral Pledget for Tip Deflection," filed Nov. 29, 2012, now U.S. Pat. No. 9,289,207, issued Mar. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/706,827, entitled "Surgical Stapler with Varying Staple Widths Along Different Circumferences," filed Dec. 6, 2012, now abandoned, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,992, entitled "Pivoting Anvil for Surgical Circular Stapler," filed Nov. 29, 2012, now U.S. Pat. No. 9,498,222, issued Nov. 22, 2016, the disclosure of which is incorporated by reference herein. Various suitable ways in which such teachings may be combined will be apparent to those of ordinary skill in the art.

Figure 30A:
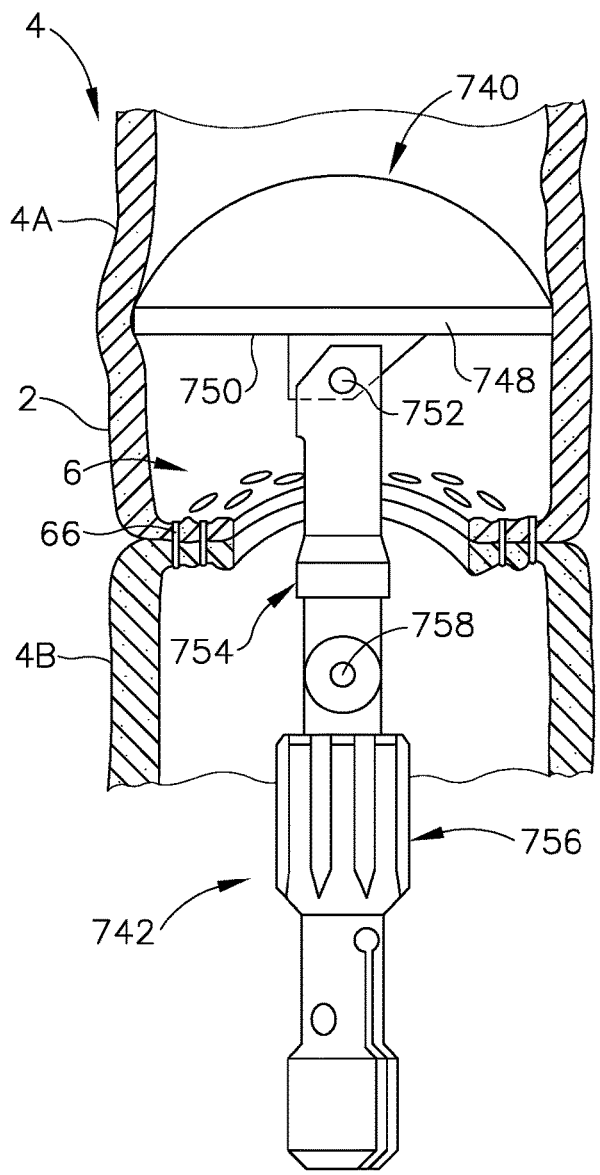
FIG. 30A depicts a partial, cross-sectional perspective view of an exemplary anvil in a first position in which the anvil has interacted with a stapling head assembly to create an anastomosis.
Figure 30B:
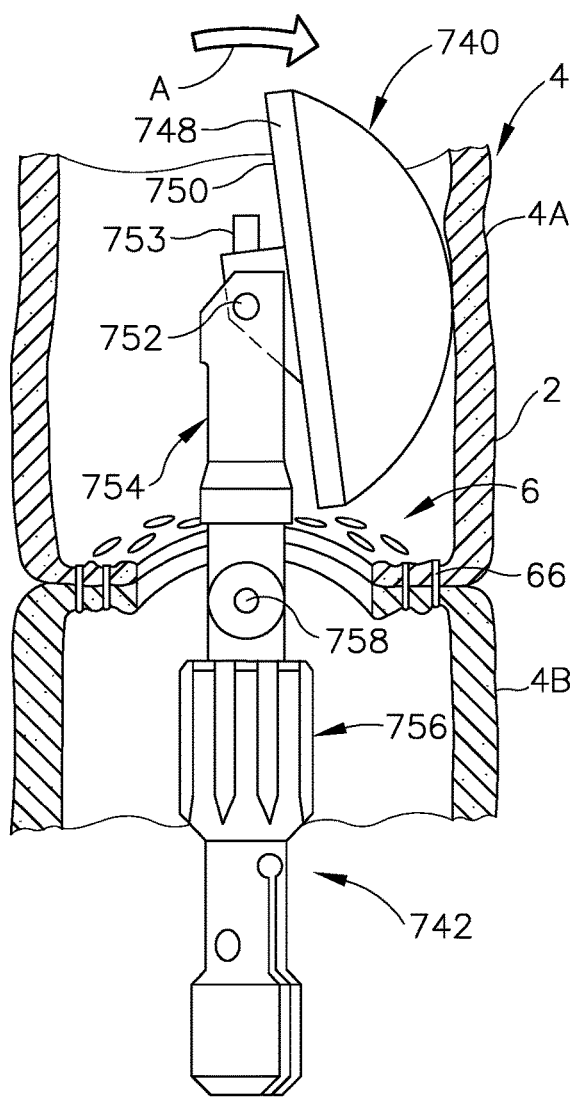
FIG. 30B depicts a partial, cross-sectional perspective view of the anvil of FIG. 30A in a second position in which an anvil head of the anvil has been tilted away from a link and an anvil shaft portion.
Figure 30C:
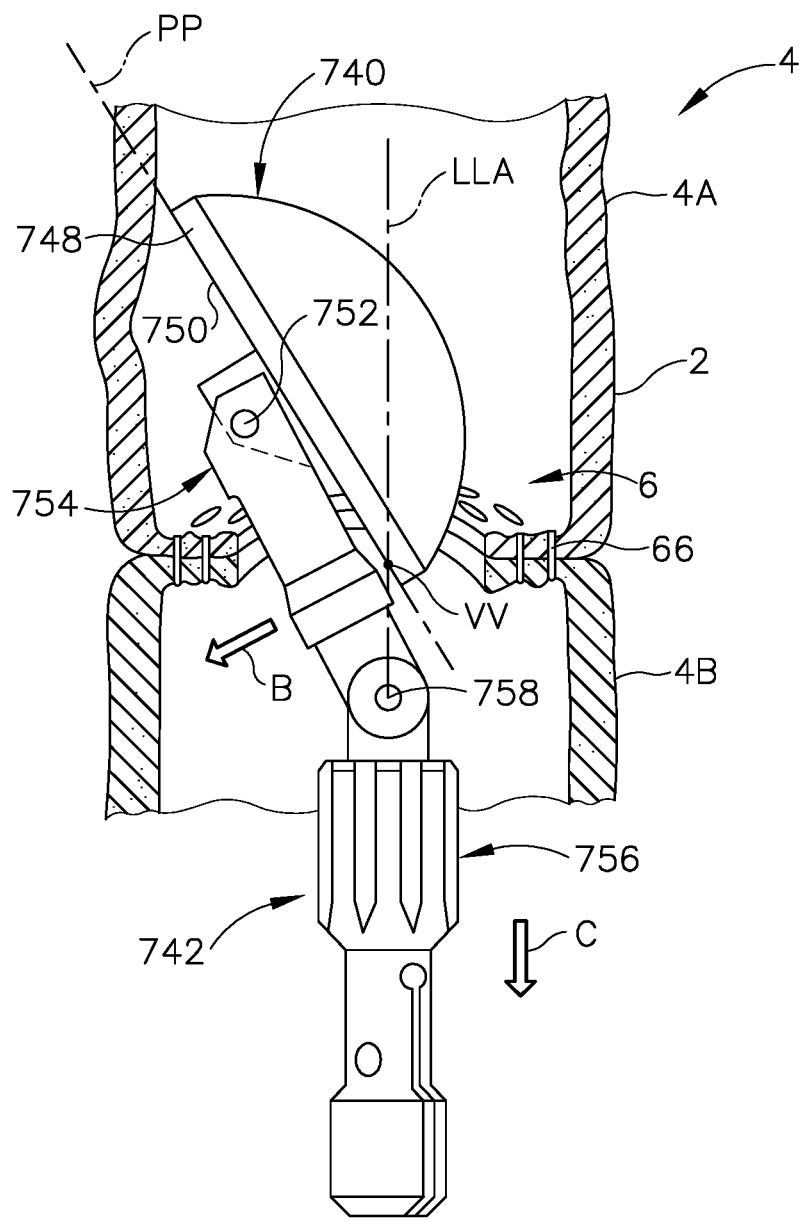
FIG. 30C depicts a partial, cross-sectional perspective view of the anvil of FIG. 7A in a third position in which a link of the anvil shaft is tilted away from the anvil shaft portion.

As described in U.S. patent application Ser. No. 13/688, 992, issued as U.S. Pat. No. 9,498,222 on Nov. 22, 2016, and as shown in FIGS. 30A-30C, an exemplary first tilting anvil (740) includes anvil head (748) and a proximal shaft (742) extending proximally from anvil head (748). Proximal shaft (742) is attachable to trocar (38) in a manner as described above with respect to proximal shaft (42) or as will be apparent to one of ordinary skill in the art in view of the teachings herein. Proximal shaft (742) comprises a flexible material, a rigid material, or any suitable material as will be apparent to one of ordinary skill in the art in view of the teachings herein. Anvil head (748) is similar to anvil head (48), described above, and includes a plurality of staple forming pockets (not shown) formed in a proximal face (750) of anvil head (748). Anvil head (748) operates with staples (66) in a similar manner as described above for anvil head (48).

Anvil head (748) is linked to proximal shaft (742). Proximal shaft (742) includes link (754) and shaft portion (756). Link (754) and shaft portion (756) are linked together via linking pivot (758). Link (754) is rotatable about a longitudinal axis of linking pivot (758). Anvil head (748) is linked to link (754) via head pivot (752). Anvil head (748) is rotatable about a longitudinal axis of head pivot (752) in the direction of arrow (A), as shown in FIG. 30B. Link (754) of proximal shaft (742) is rotatable about linking pivot (758) in the direction of arrow (B), as shown in FIG. 30C. Head pivot (752), and other pivots of the present disclosure, may be comprised of, for example, pins received through channels or other suitable structures as will be apparent to those of ordinary skill in the art in view of the teachings herein.

As shown in FIG. 30B, driver rod (753) is disposed and translatable within proximal shaft (742). When driver rod (753) is advanced to a distal position, driver rod (753) engages an off-center point of proximal face (750) of anvil (740) with sufficient force to tilt anvil head (748) about head pivot (752) in the direction of arrow (A). Driver rod (753) keeps anvil head (748) in the tilted position while driver rod (753) is in the distal position. In some versions, driver rod (753) is retracted proximally before link (754) rotates about linking pivot (758) as shown in FIG. 30C. In some other versions, driver rod (753) stays in the distal position when link (754) rotates about linking pivot (758). It should therefore be understood that driver rod (753) may either proximally terminate distal to linking pivot (758); or driver rod may flex through linking pivot (758).

In some versions, the longitudinal position of driver rod (753) relative to anvil head (748) is based on the position of anvil (740) in relation to stapling head assembly (20). For instance, driver rod (753) may be configured to remain in the distal position whenever anvil (740) is decoupled from trocar (38) of stapling head assembly (20). In some such versions, driver rod (753) may automatically retract proximally upon coupling anvil (740) with trocar (38). Alternatively, driver rod (753) may be configured to remain in the distal position even after anvil (740) is coupled with trocar (38), when anvil (740) is still spaced significantly from stapling head assembly (20) (e.g., before anvil (740) is drawn toward stapling head assembly (20) by trocar (38) to clamp tissue between anvil (740) and stapling head assembly (20), etc.). In some such versions, a feature in anvil (740) and/or a feature in stapling head assembly (20) may be configured to retract driver rod (753) proximally, thereby allowing anvil head (748) to pivot to the position shown in FIG. 30A, when anvil (740) is retracted within a certain distance relative to stapling head assembly (20). For instance, a camming feature of proximal shaft (742) may interact with a complementary feature of stapling head assembly (20) when proximal shaft (742) is retracted to a certain position within stapling head assembly (20). Instead of automating the retraction of driver rod (753), a separate actuator may extend along shaft assembly (60) to actuator handle assembly (70), enabling the operator to selectively advance/retract driver rod (753) independently. As still another variation, driver rod (753) may be integral with shaft portion (756), and the combination of driver rod (753) and shaft portion (756) may selectively slide relative to link (754) and pivot (758) to selectively advance/retract driver rod (753). As yet another merely illustrative example, an electromechanical feature (e.g., solenoid, etc.) may be used to selectively advance/retract driver rod (753) in an automated fashion or in a manual/independent fashion. Other suitable ways in which driver rod (753) may be actuated will be apparent to those of ordinary skill in the art in view of the teachings herein.

In use, anvil (740) is inserted into an interior lumen of tissue (2) in an anvil inserting direction. For instance, anvil (740) may be inserted trans-orally into esophagus (4) of a patient. Before anvil (740) is inserted, a portion of esophagus (4) may be resected and removed (e.g., using an endocutter type of linear cutting/stapling device), resulting in separation of upper esophagus (4A) from lower esophagus (4B). Anvil (740) may be fed down upper esophagus (4A) until it reaches the bottom end of upper esophagus (4A), where instrument (10) may be used to join upper esophagus (4A) and lower esophagus (4B) through an end-to-end anastomosis (6). Anvil (740) may be in positions shown in FIG. 30B or 30C while being inserted, for example, and prior to shaft portion (756) being secured to a trocar of a stapling head assembly, such as in the manner described above to attach anvil (40) to trocar (38) and stapling head assembly (20). In some versions, conventional surgical graspers are inserted through esophagus (4) to grasp shaft portion (756) and thereby pull anvil (740) to the anastomosis site via upper esophagus (4A).

Anvil (740) may be straightened into a position as shown in FIG. 30A prior to interacting with stapling head assembly (20) as described above. Stapling head assembly (20) is advanced toward anvil (740) through lower esophagus (4B) in a stapling direction that is opposite the anvil inserting direction. Shaft portion (756) is then coupled with trocar (38). The force deployed by the firing and stapling system as described above may straighten anvil (740) and shaft portion (756) into the position shown in FIG. 30A (for example, when instrument (10) clamps tissue between stapling head assembly (20) and anvil head (748)). The positions will be described further below with respect to a retraction of anvil (740). Anvil (740) may then be used as described above to staple tissue (2) with staples (66). FIG. 30A shows a position after which anvil (740) has been used to staple tissue (2) with staples (66), and after which knife (36) has severed tissue, thereby creating a secure anastomosis (6).

To retract anvil (740), driver rod (753) is distally advanced, causing anvil head (748) to pivot about head pivot (752) in the direction of arrow (A) shown in FIG. 30B. Remaining in an extended position, driver rod (753) assists to maintain anvil head (748) in the first flipped or tilted position shown in FIG. 30B in a manner as will be apparent to those of ordinary skill in the art in view of the teachings herein. For example, driver rod (753) may contain a laterally offset portion (not shown) that abuts against proximal face (750) when driver rod (753) is in the extended position. The laterally offset portion thus prevents anvil head (748) from rotating back to the position of anvil head (748) shown in FIG. 30A.

Shaft portion (756) is proximally retracted along the direction of arrow (C) to retract anvil (740) through the lumen defined by tissue (2) (such as the esophagus (4)). Load on anvil head (748) from this retraction may provide the pivoting at linking pivot (758). For example, anvil head (748) may abut inner surface walls of tissue (2), causing link (754) to pivot about linking pivot (758) at angles of from about 30 degrees to about 45 degrees with respect to shaft portion (756) as anvil (740) is retracted proximally. Further, anvil head (748) is pivoted about head pivot (752) such that anvil head (748) may be retracted within an internal passageway of tissue (2) with minimal interaction with the inner surface walls of tissue (2). In other words, the above-described tilting and pivoting may prevent the outer edge of anvil head (748) from scraping against the inner wall of esophagus as anvil (740) is transported through esophagus. In the position shown in FIG. 30C, for example, link (754) is tilted with respect to shaft portion (756) and anvil head (748) is tilted with respect to link (754) into a retraction position. A plane of anvil head (748) depicted as plane (PP) in FIG. 30C defines an acute angle with longitudinal axis (LLA) of shaft portion (756) of proximal shaft (742), with vertex (VV) of the angle being positioned lower than head pivot (752). In the retraction position, a retraction of anvil (740) in the direction of arrow (C) substantially avoids snagging a lowermost portion of anvil head (748), disposed closest to linking pivot (758), with an interior surface of tissue (2), and particularly with edges of anastomosis (6) that are shown as stapled together via staples (66).

Driver rod (753) may remain extended during retraction of anvil (740) as described above. Further, anvil head (748) may be lockable at either the position shown in FIG. 30B or the position shown in FIG. 30C to ease extraction of anvil head (748) from anastomosis (6) to reduce anastomosis trauma during the retraction of anvil (740). For example, an internal projection in link (754) may be received in an internal notch in shaft portion (756) laterally offset from linking pivot (758) and disposed at a location to lock link (754) at a desired tilting angle with respect to shaft portion (756). By way of example only, shaft portion (756) may selectively slide relative to link (754) and pivot (758) to selectively lock the tilted angle of link (754) at pivot (758).

In some versions, anvil head (748) is resiliently biased to tilt to the position shown in FIGS. 30B and 30C. In such versions, driver rod (753) may be omitted (or still be included). In addition or in the alternative, link (754) may be resiliently biased to tilt to the position shown in FIG. 30C. Various suitable ways in which such biases may be provided will be apparent to those of ordinary skill in the art in view of the teachings herein. It should also be understood that, in such versions, link (754) and anvil head (748) may eventually tilt to the positions shown in FIG. 30A once anvil (740) is coupled with trocar (38) and anvil (740) is retracted toward stapling head assembly (20). In other words, the internal axial passageway within stapling head assembly (20) may straighten link (754) and the distal face of stapling head assembly (20) may straighten anvil head (748). Other suitable ways in which an anvil may include a multi-pivot shaft will be apparent to those of ordinary skill in the art in view of the teachings herein.

Figure 31:
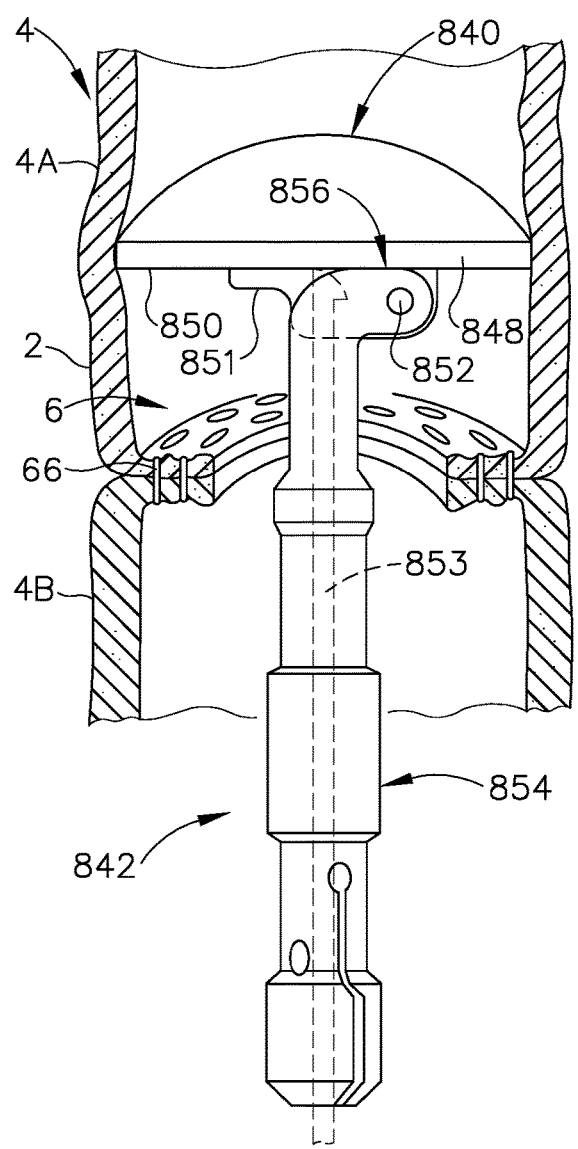
FIG. 31 depicts a partial cross-sectional, perspective view of another exemplary anvil in a first position in which the anvil has interacted with a stapling head assembly to create an anastomosis.
Figure 32:
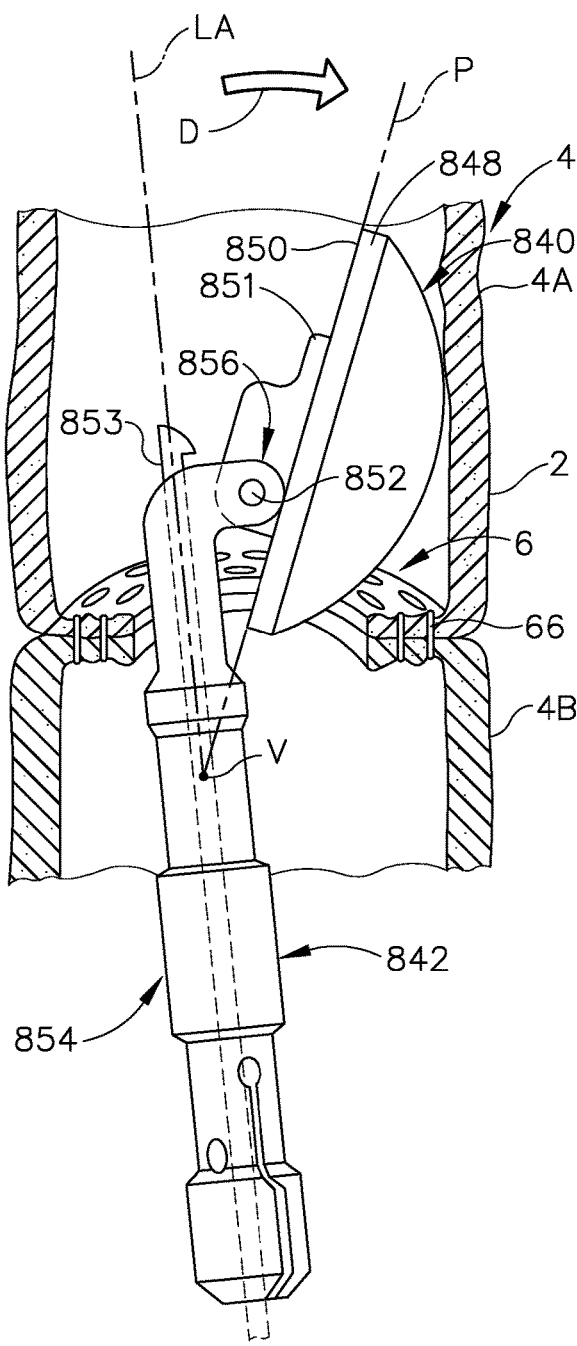
FIG. 32 depicts a partial cross-sectional, perspective view of the anvil of FIG. 8 in a second position in which an anvil head is tilted about an off-center pivot of an anvil shaft portion of the anvil.

FIGS. 31-32 show an exemplary second tilting anvil (840) including anvil head (848) and a proximal shaft (842) extending proximally from anvil head (848). Proximal shaft (842) is attachable to trocar (38) in a manner as described above with respect to proximal shaft (42) or as will be apparent to one of ordinary skill in the art in view of the teachings herein. Proximal shaft (842) comprises a flexible material, a rigid material, or any suitable material as will be apparent to one of ordinary skill in the art in view of the teachings herein. Anvil head (848) is similar to anvil head (48), described above, and includes a plurality of staple forming pockets (not shown) formed in a proximal face (850) of anvil head (848). Anvil head (848) operates with staples (66) in a similar manner as described above for anvil head (48).

Anvil head (848) includes linking connector (851), which connects anvil head (848) to proximal shaft (842). Anvil head (848) is linked to proximal shaft (842) via off-set head pivot (852). Anvil head (848) is rotatable about a longitudinal axis of head pivot (852) in the direction of arrow (D), as shown in FIG. 32. Driver rod (853) is disposed and translatable within proximal shaft (842) in a manner similar to that described for driver rod (753). Proximal shaft (842) includes a first portion (854) in which driver rod (853) is disposed and a second portion (856) extending laterally from a distal end of first portion (854) of proximal shaft (842). Head pivot (852) is disposed in second portion (856) and is off-set from the longitudinal axis of first portion (854). Head pivot (852) connects linking connector (851) of anvil head (848) to second portion (856) of proximal shaft (842), such that linking connector (851) and anvil head (848) are rotatable relative to second portion (856) about a longitudinal axis of head pivot (852).

In use, anvil (840) is inserted into an interior lumen of tissue (2) (e.g., upper esophagus (4A), etc.) in an anvil inserting direction in a manner similar to that described above for anvil (740). Anvil (840) may be in a position shown in FIG. 32 while being inserted, for example. When proximal shaft (842) is coupled with trocar (38), the clamping of tissue between stapling head assembly (20) and anvil (340) will straighten anvil (840) before a firing actuation as described above. Thus, the force deployed by the firing and stapling system as described above will straighten anvil (840) into the position shown in FIG. 31. Anvil (840) may then be used as described above to staple interior surfaces of tissue (2). FIG. 31 shows a position after which anvil (840) has been used to staple interior surfaces of a lumen of tissue (2) with staples (66) to create anastomosis (6).

To retract anvil (840), driver rod (853) is distally advanced, causing anvil head (848) to pivot about head pivot (852) in the direction of arrow (D) shown in FIG. 32. Driver rod (853) may remain advanced to assist in maintaining anvil head (748) in the tilted position shown in FIG. 32. Because second portion (856) is laterally off-set from first portion (854), anvil head (848) is able to rotate about head pivot (852) into a position in which anvil head (848) is at an obtuse angle with respect to a starting position of anvil head (848). In particular, anvil head (848) rotates more than 90 degrees with respect to proximal shaft (842) in the present example. A plane of anvil head (848) depicted as plane (P) in FIG. 32 defines an acute angle with longitudinal axis (LA) of proximal shaft (842), with the vertex (V) of the angle being at a position that is lower than head pivot (852). Thus, once flipped, a proximal end of anvil head (848) is disposed below second portion (856) and between ends of second portion (856) and first portion (854) of proximal shaft (842).

Anvil head (848) may be lockable at the obliquely angled position of FIG. 32 to ease extraction of anvil head (848) from anastomosis (6) in a manner similar to that described above to lock anvil head (748) as will be apparent to those of ordinary skill in the art in view of the teachings herein. For example, a projection on an interior surface of linking connector (851) may advance until receipt in a complementary notch disposed in an interior surface of second portion (856). Additionally or alternatively, a laterally projecting portion of drive rod (853) may be received into a notch disposed in an underside of linking connector (851). Other suitable ways in which drive rod (853) may be selectively locked in the distal position shown in FIG. 32 (or at least resiliently biased to the distal position shown in FIG. 32) will be apparent to those of ordinary skill in the art in view of the teachings herein.

First portion (854) is proximally retracted downwardly through esophagus (4) to retract anvil (840) from esophagus (4) in a manner as described above. Load on anvil head (848) from this retraction may cause proximal shaft (842) to tilt in a direction opposite arrow (D) while within esophagus (4), such that longitudinal axis (LA) of proximal shaft (842) is tilted relative to the axis of esophagus (4). With anvil head (848) and proximal shaft (842) tilted (as shown in FIG. 32), anvil head (848) may be retracted downwardly esophagus (4) with minimal interaction between the outer edge of anvil head (848) and the inner surface walls of esophagus (4). In other words, the above-described tilting and pivoting may prevent the outer edge of anvil head (848) from scraping against the inner wall of esophagus as anvil (840) is transported through esophagus.

Similarly, at least some of the teachings herein may be readily combined with one or more teachings of U.S. patent application Ser. No. 13/693,455, entitled "Circular Anvil Introduction System with Alignment Feature," filed Dec. 4, 2012, issued as U.S. Pat. No. 9,724,100 on Aug. 8, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,313, entitled "Circular Stapler with Selectable Motorized and Manual Control, Including a Control Ring," filed on Dec. 17, 2012, and issued as U.S. Pat. No. 9,532,783 on Jan. 3, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,318, entitled "Motor Driven Rotary Input Circular Stapler with Modular End Effector," filed on Dec. 17, 2012, and issued as U.S. Pat. No. 9,597,081 on Mar. 21, 2017, the disclosure of which is incorporated by reference herein. Various suitable ways in which such teachings may be combined will be apparent to those of ordinary skill in the art.

As described in U.S. patent application Ser. No. 13/716,318, issued as U.S. Pat. No. 9,597,081 on Mar. 21, 2017, FIGS. 33-40 show various features that are used to drive stapling head assembly (440) of the present example. In particular, these features include a first rotary drive element (450), a second rotary drive element (460), a drive nut (470), and a clamping driver (480). These components (450, 460, 470, 480) are coaxially aligned with drive shaft (432) and are all housed within a cartridge housing (600), which will be described in greater detail below. As can also be seen in FIG. 33, stapling head assembly (440) includes staple deck (442), a staple driver (443), and a cylindraceous knife (445). Staple driver (443) is operable to translate distally to drive staples (not shown) through openings in staple deck (442) and into staple forming pockets of proximal face (496) of anvil (490). Knife (445) translates distally with staple driver (443), thereby cutting tissue at substantially the same time that the adjacent tissue is being stapled.

Figure 34:
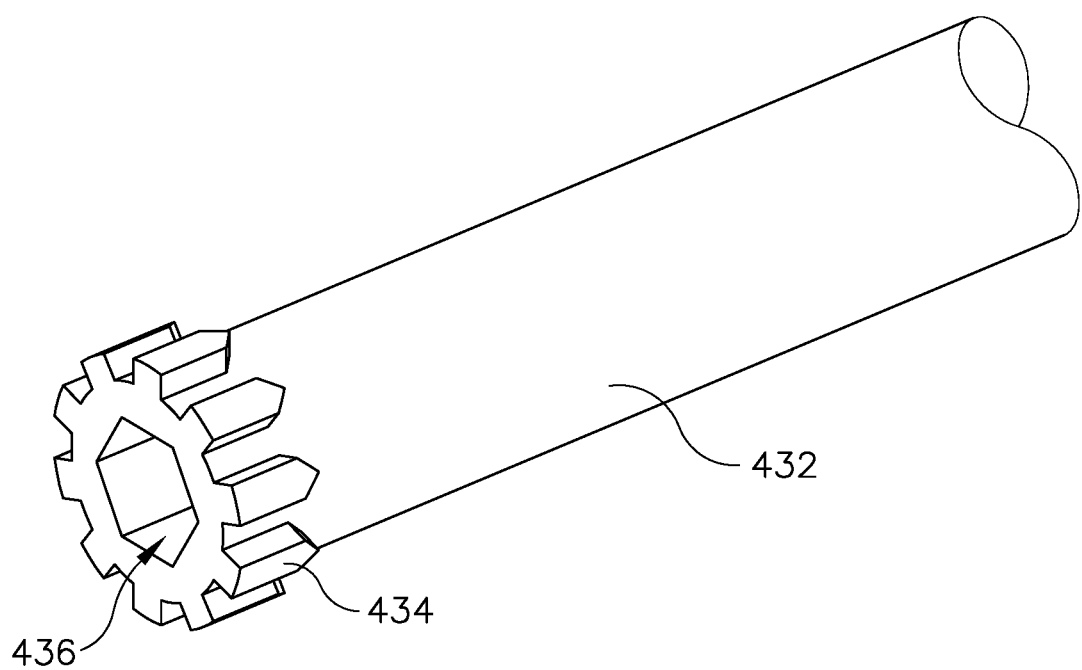
FIG. 34 depicts a partial perspective view of the distal end of the rotary drive shaft of the surgical instrument of FIG. 33.
Figure 35:
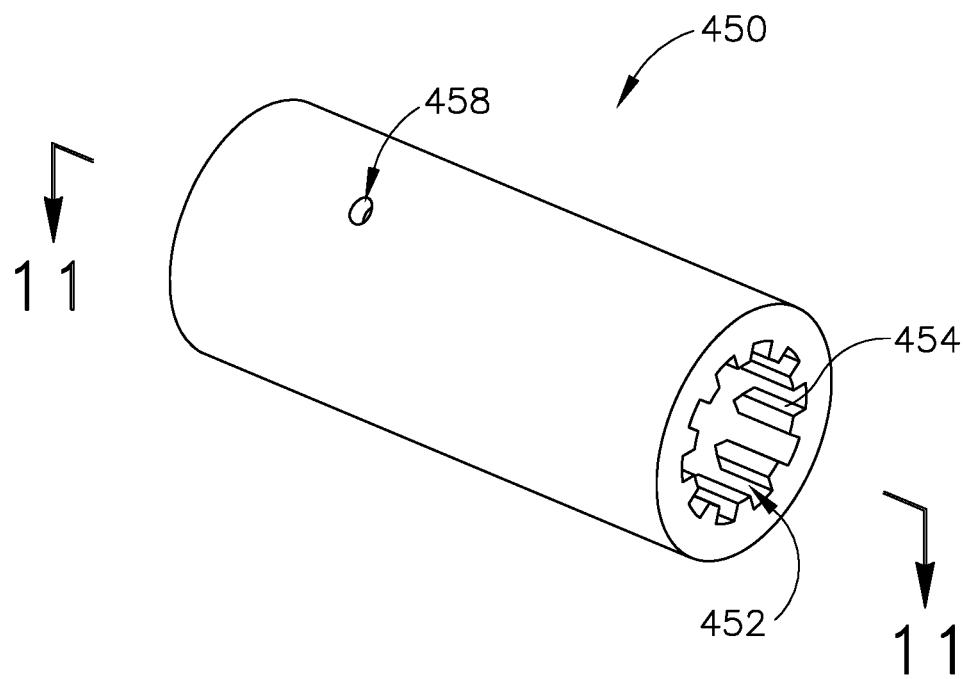
FIG. 35 depicts a perspective view of a first rotary drive element of the stapling head assembly of FIG. 33.
Figure 36:
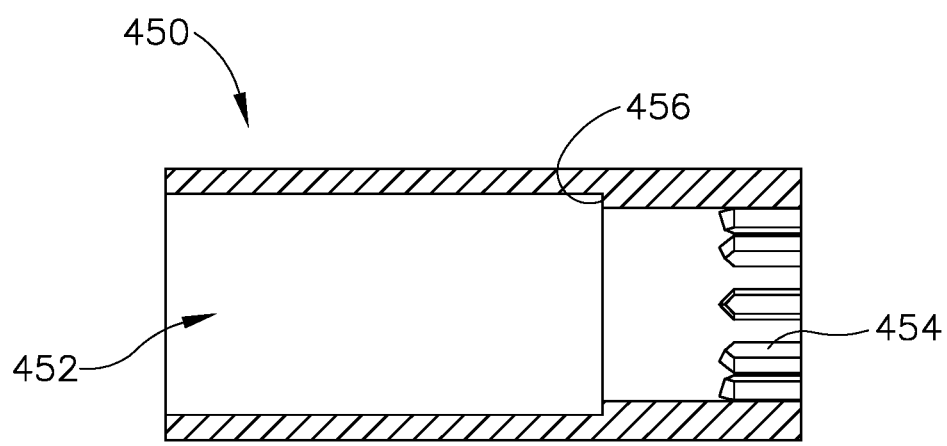
FIG. 36 depicts a cross-sectional view of the first rotary drive element of FIG. 35, taken along line 11-11 of FIG. 35.

As best seen in FIGS. 35-36, first rotary drive element (450) defines a bore (452) and includes a proximal set of inner splines (454). The diameter of bore (452) increases distal to inner splines (454), such that first rotary drive element (450) includes a distally facing annular shoulder (456). First rotary drive element (450) also includes a threaded opening (458) that extends transversely from the exterior of first rotary drive element (450) into bore (452). As shown in FIG. 34, the distal end of drive shaft (432) includes a set of outer splines (434) that complement inner splines (454) of first rotary drive element (450). Thus, when splines (434, 454) are at a common longitudinal position, rotation of drive shaft (432) rotates first rotary drive element (450). In the present example, splines (434, 454) are at a common longitudinal position when drive shaft (432) is in a proximal position. When drive shaft (432) is driven to a distal position (e.g., by sliding control ring (416) distally), splines (434, 435) disengage such that rotation of drive shaft (432) will not rotate first rotary drive element (450). As shown in FIGS. 34-36, splines (434, 454) have complementary tapered ends to promote positioning of splines (434) in the interstices between splines (454) when drive shaft (432) is translated back from the distal position to the proximal position.

Figure 37:
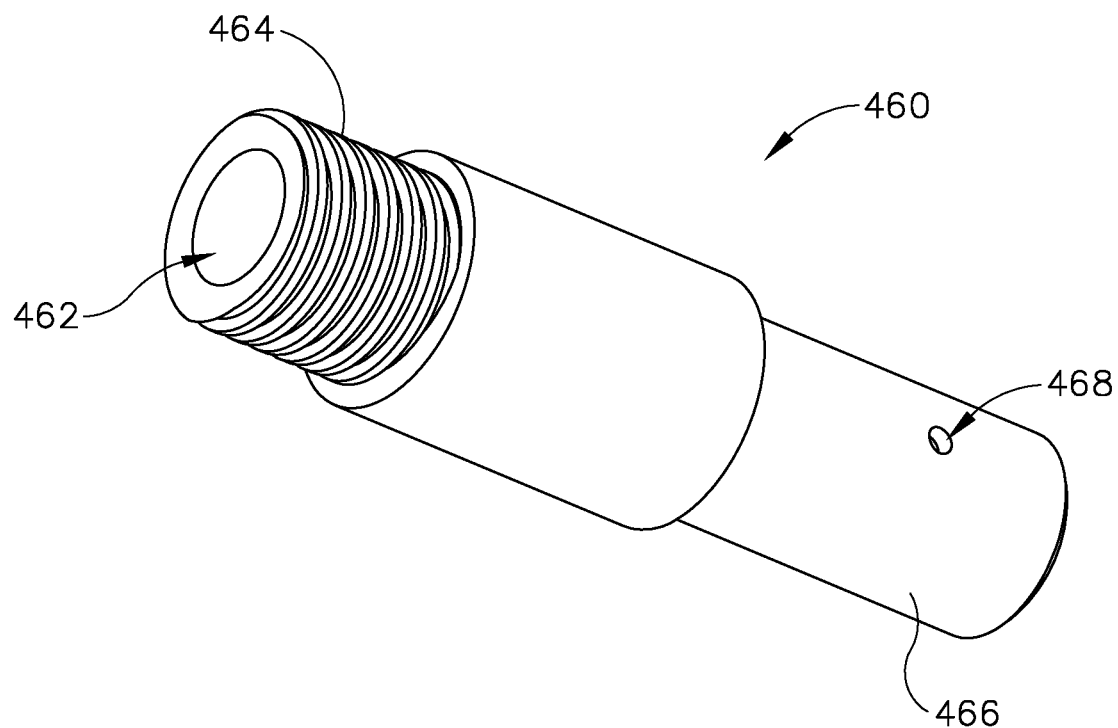
FIG. 37 depicts a perspective view of a second rotary drive element of the stapling head assembly of FIG. 33.

As best seen in FIG. 37, second rotary drive element (460) of the present example defines an inner bore (462), includes outer threading (464) at its distal end, and includes a necked-down proximal portion (466). A threaded opening (468) extends transversely from the exterior of second rotary drive element (460) into bore (462). Proximal portion (466) is configured to slidably fit within bore (462) of first rotary drive element (450). In particular, threaded openings (458, 468) align with each other when proximal portion (466) is disposed in bore (452), and a set screw is secured in threaded openings (458, 468) to secure first and second rotary drive elements (450, 460) together. First and second rotary drive elements (450, 460) will thus rotate together unitarily.

Figure 33:
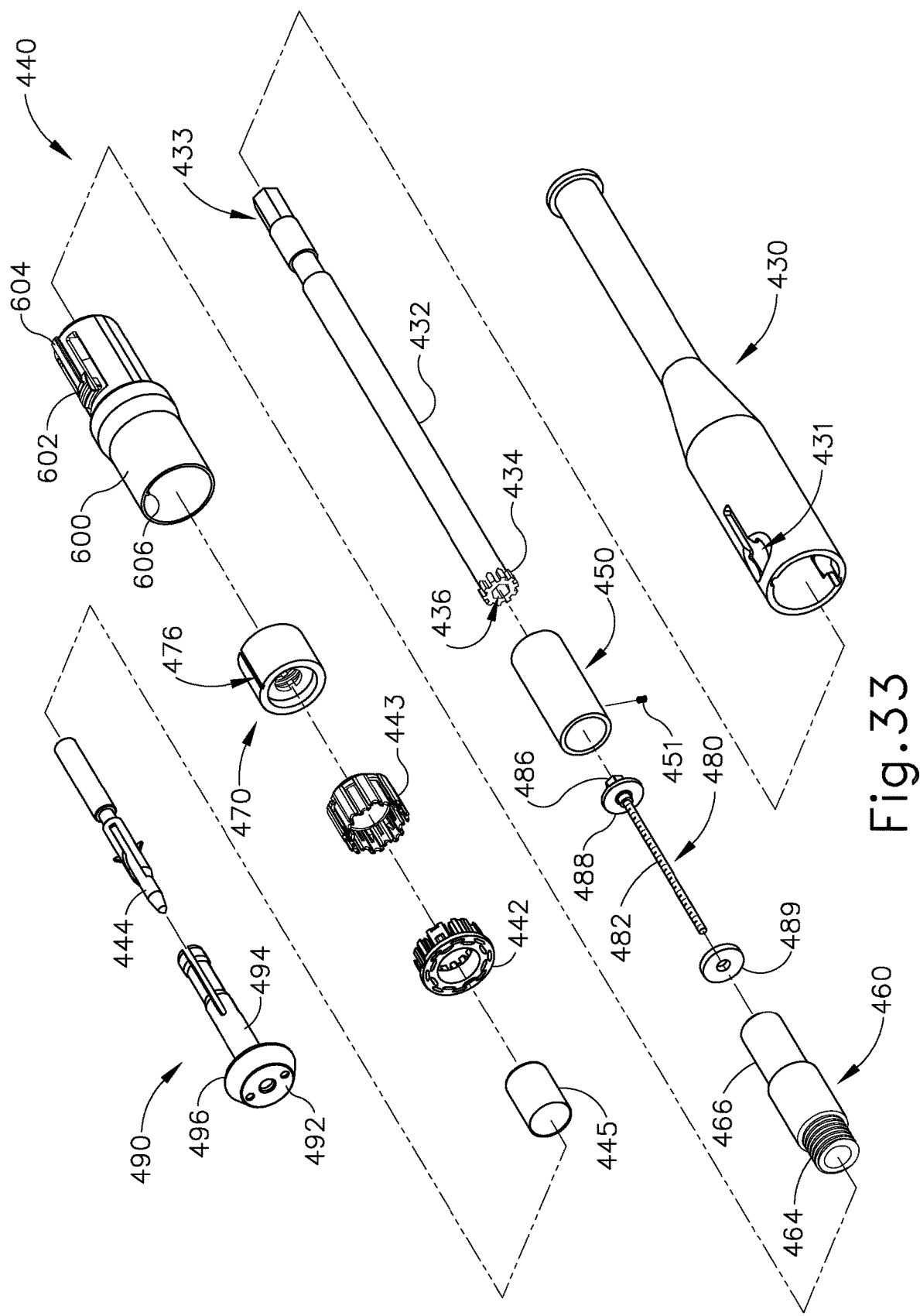
FIG. 33 depicts a partially exploded view of a surgical instrument, showing components of a stapling head assembly.
Figure 38:
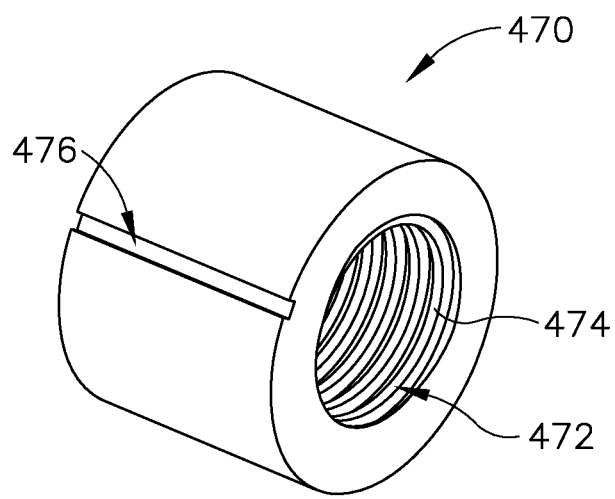
FIG. 38 depicts a perspective view of a drive nut of the stapling head assembly of FIG. 33.

As best seen in FIG. 38, drive nut (470) of the present example defines an inner bore (472), includes an inner threading (474), and includes an outer keyway (476). Bore (472) is configured to receive the distal end of second rotary drive element (460). In particular, threading (464) meshes with threading (474). Outer keyway (476) receives a key (606) that extends inwardly from cartridge housing (600) (as shown in FIG. 33). The relationship between keyway (476) and key (606) prevents drive nut (470) from rotating relative to cartridge housing (600); but permits drive nut (470) to translate relative to cartridge housing (600). It should therefore be understood that, when drive shaft (432) and rotary drive elements (450, 460) rotate together, the relationship between threading (464, 474) will cause drive nut (470) to translate distally or proximally within cartridge housing (600), depending on the direction in which drive shaft (432) and rotary drive elements (450, 460) are rotated. Staple driver (443) and knife (445) are fixedly secured to drive nut (470) in this example, such that staple driver (443) and knife (445) translate unitarily with drive nut (470) relative to staple deck (442) and relative to cartridge housing (600). It should therefore be understood that, when drive shaft (432) is at a proximal position and is rotated, such rotation will drive staple driver (443) and knife (445) distally or proximally relative to staple deck (442) and relative to cartridge housing (600), depending on the direction of rotation.

Figure 39:
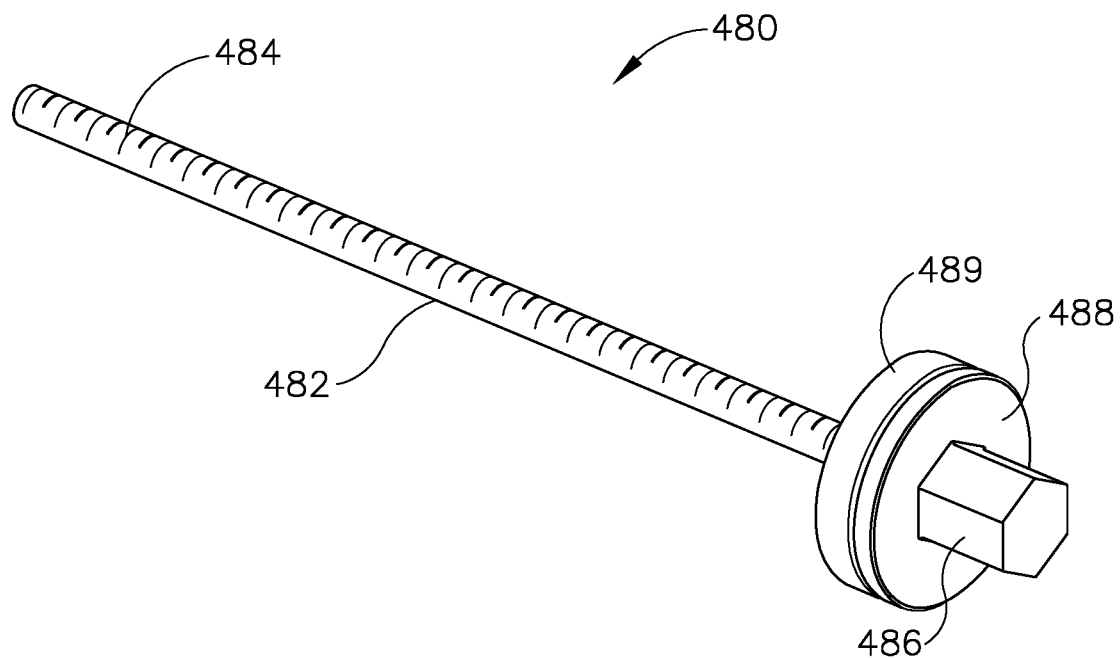
FIG. 39 depicts a perspective view of a clamping driver of the stapling head assembly of FIG. 33.
Figure 40:
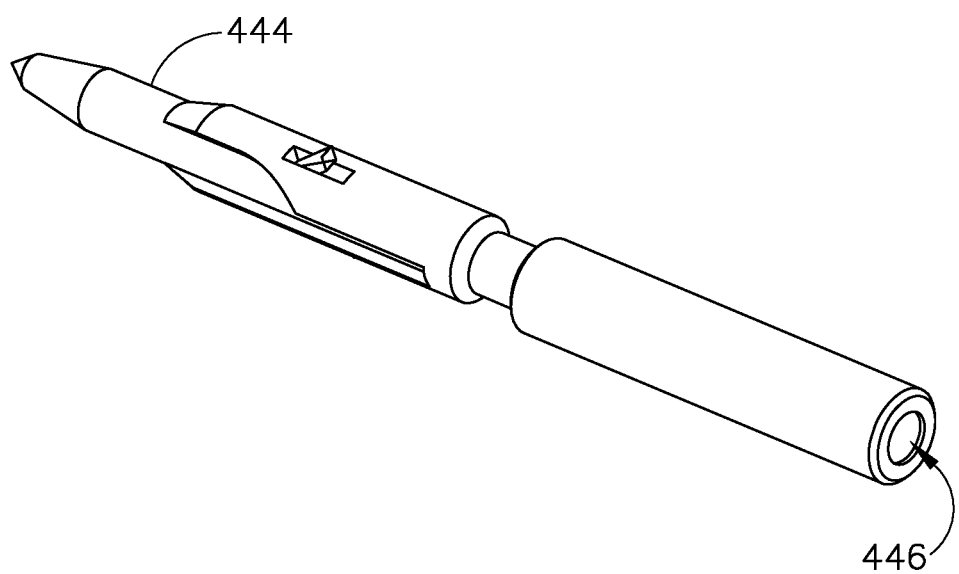
FIG. 40 depicts a perspective view of the trocar of the stapling head assembly of FIG. 33.

As best seen in FIG. 39, clamping driver (480) of the present example comprises a shaft (482) with threading (484) at the distal end of shaft (482). Clamping driver (480) also includes a proximal drive feature (486), an annular flange (488), and a thrust bearing (489) that is positioned about shaft (482) and distal to annular flange (488). As best seen in FIGS. 41A-41D, shaft (482) extends longitudinally through bores (452, 462, 472) to reach trocar (444). As best seen in FIG. 40, the proximal end of trocar (444) includes a threaded opening (446). Threaded opening (446) is configured to receive the distal end of shaft (482), thereby meshing with threading (484). Trocar (444) is operable to translate relative to cartridge housing (600) but not rotate relative to cartridge housing (600). Thus, trocar (444) will translate relative to cartridge housing (600) in response to rotation of clamping driver (480) relative to cartridge housing (600), due to interaction between threading (484) and threaded opening (446). As can also be seen in FIGS. 41A-41D, flange (488) and thrust bearing (489) are captured between shoulder (456) of first rotary drive element (450) and the proximal end (466) of second rotary drive element (460), such that rotary drive elements (450, 460) prevent clamping driver (480) from moving longitudinally.

Proximal drive feature (486) has a hexagonal cross-section in this example, and is thus configured to complement a hexagonal recess (436) formed at the distal end of drive shaft (432) as shown in FIG. 34. While hexagonal shapes are used in the present example, it should be understood that any other suitable shape may be used, including but not limited to rectangular, semicircular, triangular, elliptical, etc. When drive shaft (432) is at the distal position (e.g., when control ring (416) is in the distal position), proximal drive feature (486) is received in hexagonal recess (436), such that rotation of drive shaft (432) rotates clamping driver (480). When drive shaft (432) is at the proximal position (e.g., when control ring (416) is in the proximal position), proximal drive feature (486) is disengaged from hexagonal recess (436), such that rotation of drive shaft (432) does not rotate clamping driver (480).

It should be understood from the foregoing that, when drive shaft (432) is at the distal position, rotation of drive shaft (432) will rotate clamping driver (480) but not rotary drive elements (450, 460). When drive shaft (432) is in the proximal position, rotation of drive shaft (432) will rotate rotary drive elements (450, 460) but not clamping driver (480). Thus, drive shaft (432) may be rotated and translated in a particular sequence to provide clamping, cutting, and stapling of tissue. An example of such a sequence is shown in FIGS. 41A-41D.

Figure 41A:
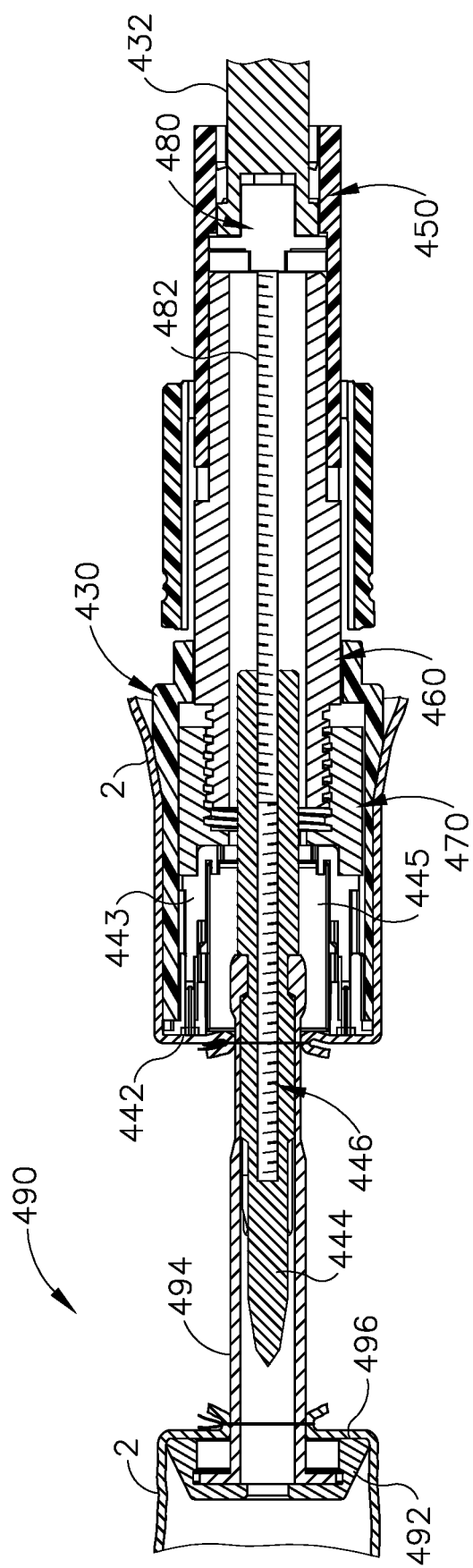
FIG. 41A depicts a cross-sectional side view of the stapling head assembly of FIG. 33, with the anvil in an open position and with the rotary drive shaft in a distal position.

In particular, FIG. 41A shows anvil (490) coupled with trocar (444) and drive shaft (432) in the distal position. It should be understood that control ring (416) is also in the distal position at this stage. Head (492) of anvil (490) is positioned in a first lumen defined by tissue (2), with shaft (494) of anvil (490) protruding from lumen. A suture is used to secure tissue (2) about shaft (494) in a purse-string fashion. In some uses, tissue (2) defines an upper section of a gastrointestinal tract, such as an upper colon portion or an upper esophagus portion. It should be understood that anvil (490) may travel proximally through lumen before being coupled with trocar (444). Stapling head assembly (440) is positioned within a second lumen defined by tissue (2). A suture is used to secure tissue (2) about trocar (444) in a purse-string fashion. In some uses, tissue (2) defines a lower section of a gastrointestinal tract, such as a lower colon portion or a lower esophagus portion. It should be understood that stapling head assembly (440) may travel distally through lumen before being coupled with anvil (490).

Figure 41B:
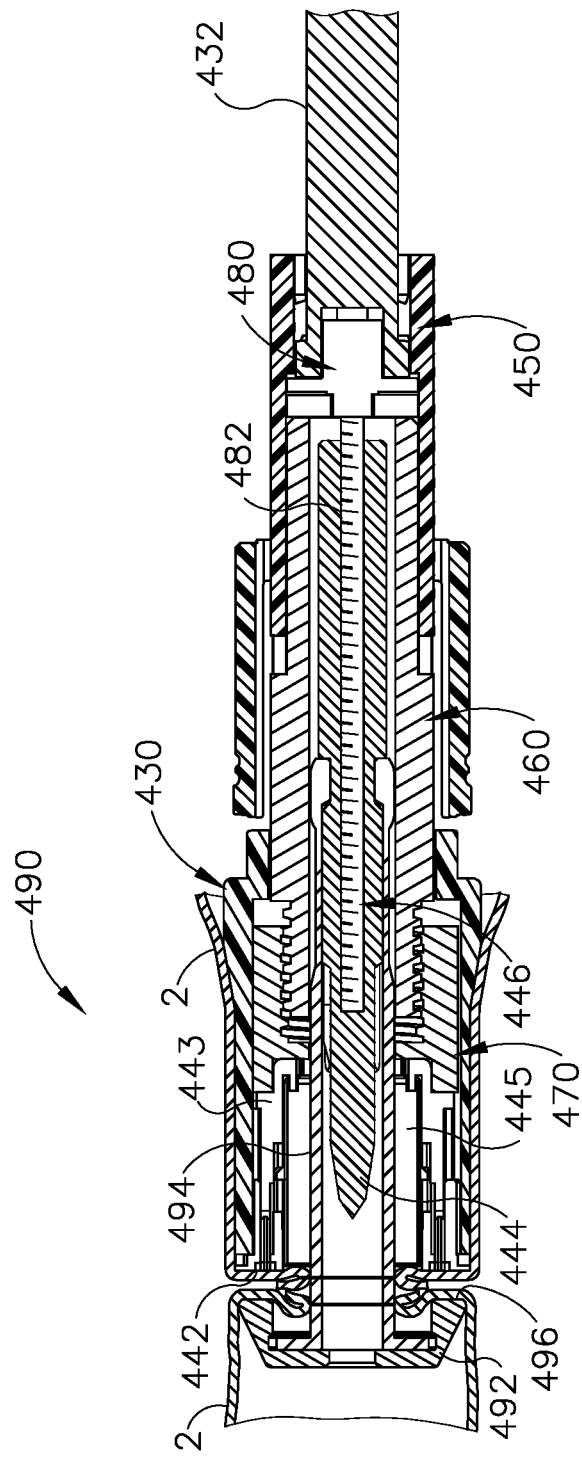
FIG. 41B depicts a cross-sectional side view of the stapling head assembly of FIG. 33, with the anvil in a closed position and with the rotary drive shaft in the distal position.

With anvil (490) and stapling head assembly (440) coupled and positioned within respective lumens, motor (422) may be activated to rotate drive shaft (432). If handle assembly (410) is in manual operation mode, control knob (414) may be manually rotated to rotate drive shaft (432). With drive shaft (432) being in the distal position, drive feature (486) of clamping driver (480) is seated in recess (436) of drive shaft (432), such that rotation of drive shaft (432) rotates clamping driver (480). This rotation retracts trocar (444) and anvil (490) proximally relative to stapling head assembly (440) as shown in FIG. 41B. This retraction provides clamping of tissue (2) between proximal face (496) of anvil head (492) and staple deck (442). Drive shaft (432) may be rotated until the desired gap between proximal face (496) and staple deck (442) is achieved. The gap may be indicated to the user in numerous ways. By way of example only, stapling instrument (400) may include an equivalent of indicator window as described above. As another merely illustrative example, an encoder or other feature may track rotation of drive shaft (432) and a control module may read such data and accordingly drive an LED display or other type of electronic display to indicate the gap distance to the user. Other suitable ways in which an operator may receive gap distance feedback will be apparent to those of ordinary skill in the art in view of the teachings herein.

Figure 41C:
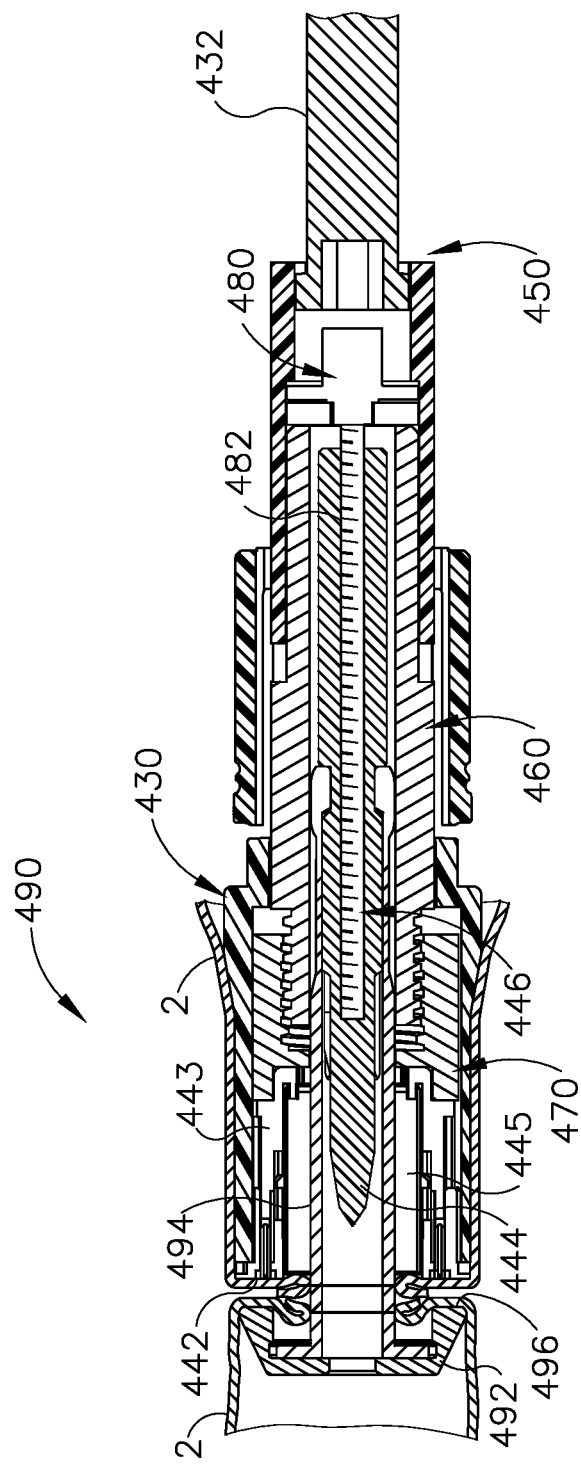
FIG. 41C depicts a cross-sectional side view of the stapling head assembly of FIG. 33, with the anvil in the closed position and with the rotary drive shaft shifted to a proximal position.

Once the operator has achieved the desired gap between proximal face (496) and staple deck (442), the user may translate drive shaft (432) proximally as shown in FIG. 41C. This may be done by translating control ring (416) proximally or in any other suitable fashion. When drive shaft (432) translates proximally (432), recess (436) disengages drive feature (486) and splines (434) engage splines (454). The translation of drive shaft (432) from the distal position to the proximal position thus shifts stapling head assembly (440) from a tissue clamping mode to a tissue cutting/stapling mode. In some other versions, stapling head assembly (440) is configured such that translating drive shaft from the distal position to the proximal position shifts stapling head assembly (440) from a tissue cutting/stapling mode to a tissue clamping mode; and vice-versa.

Figure 41D:
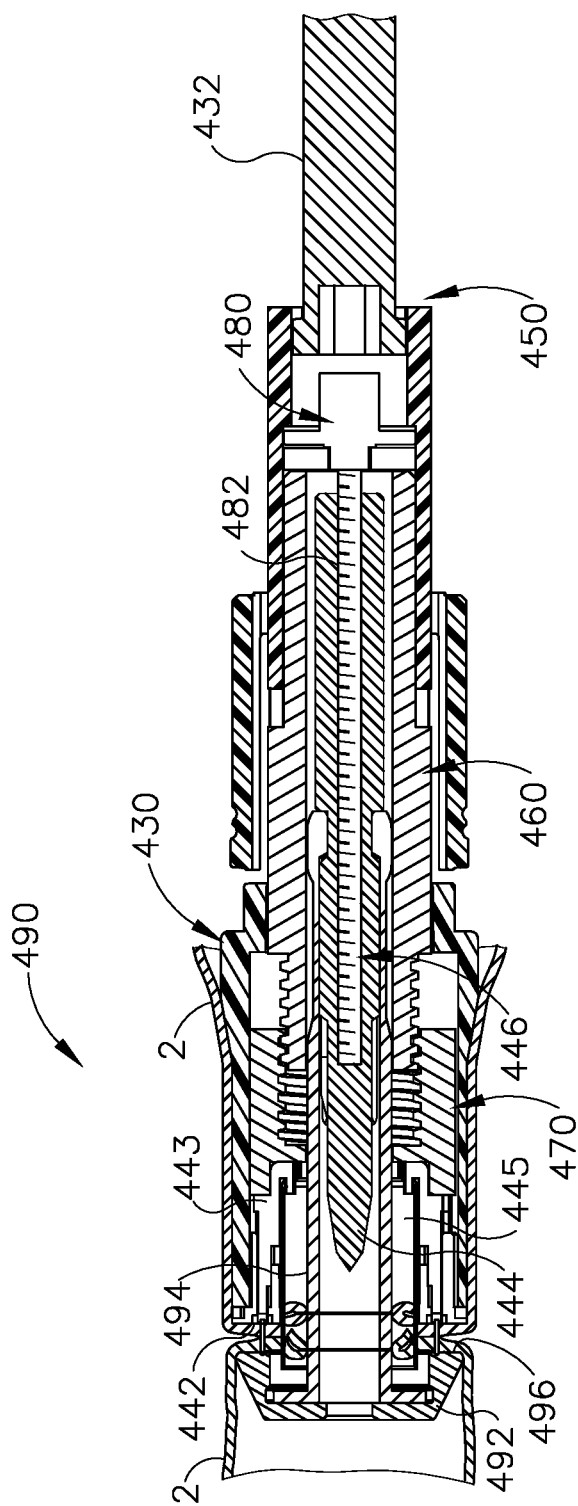
FIG. 41D depicts a cross-sectional side view of the stapling head assembly of FIG. 33, with the staple driver and blade in a fired position.

Once stapling head assembly (440) is shifted from tissue clamping mode to tissue cutting/stapling mode, drive shaft (432) may again be rotated. Again, this may be accomplished by activating motor (422); or by rotating control knob (414) manually if handle assembly (410) is in manual operation mode. In some instances, an operator may prefer to use handle assembly (410) in manual operation mode during tissue clamping (FIGS. 41A-41B), and then use handle assembly (410) in motorized mode during tissue cutting/stapling (FIGS. 41C-41D); or vice versa. In either case, when drive shaft (432) is rotated during tissue cutting/stapling mode, this rotation is communicated through rotary drive elements (450, 460). The rotation of rotary drive elements (450, 460) drives drive nut (470) distally as shown in FIG. 41D, due to engagement between threading (464, 474). This distal advancement of drive nut (470) advances staple driver (443), and knife (445) distally, thereby cutting and stapling tissue (2). An encoder, force sensor, timer, and/or any other suitable feature may be used determine when to stop motor (422) automatically upon sufficient advancement of drive nut (470), staple driver (443), and knife (445).

After tissue (2) has been stapled and cut, drive shaft (432) may be advanced distally again to engage clamping driver (480), then rotated in the opposite direction to drive anvil (490) slightly away from stapling head assembly (440). With anvil (490) still coupled with stapling head assembly (440), stapling instrument (400) may then be withdrawn proximally through lumen (2), leaving a secure and fluid tight anastomosis joining lumens together. Other suitable ways in which stapling instrument (400) may be used will be apparent to those of ordinary skill in the art in view of the teachings herein.

Figure 42A:
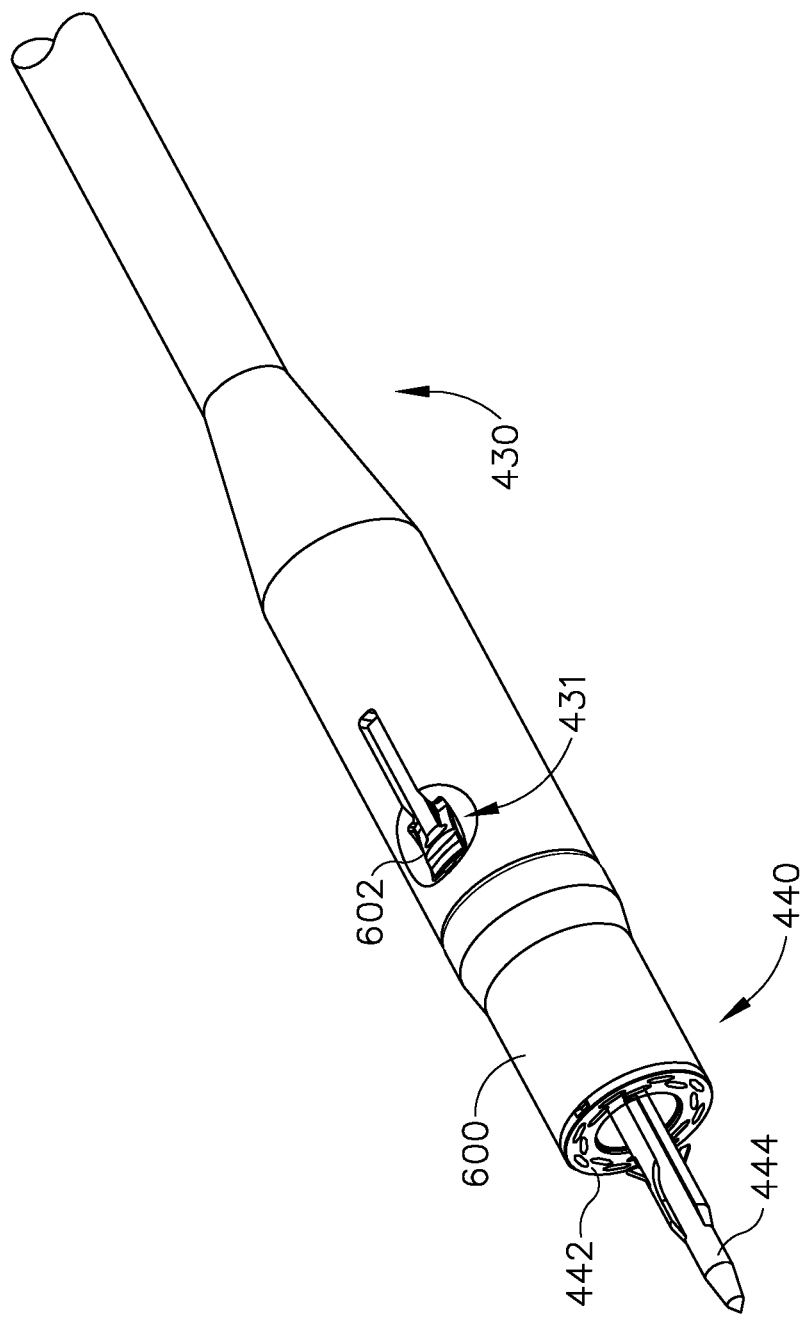
FIG. 42A depicts a perspective view of the stapling head assembly of FIG. 33, with the stapling head cartridge coupled with the shaft assembly.
Figure 42B:
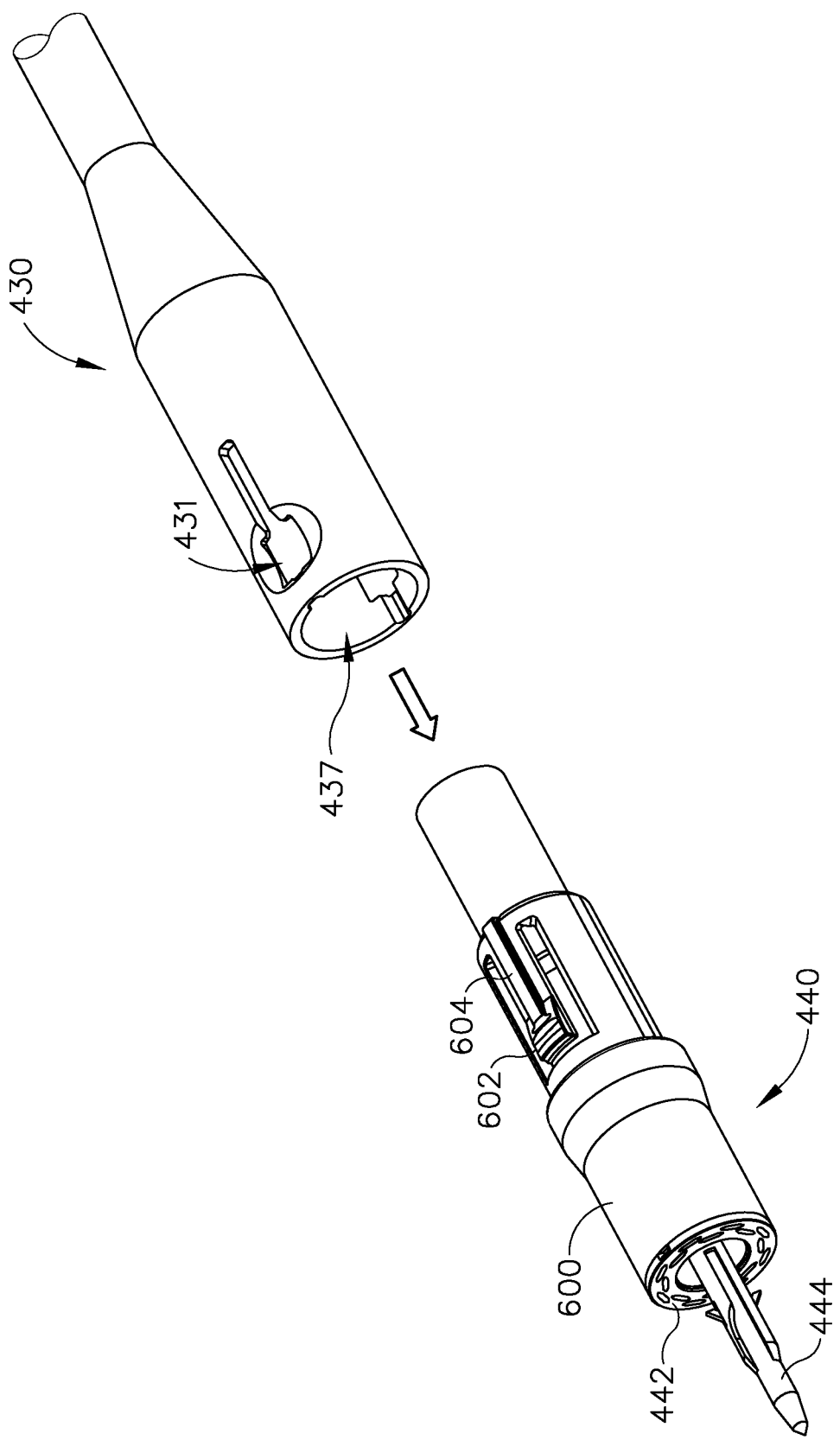
FIG. 42B depicts a perspective view of the stapling head assembly of FIG. 33, with the stapling head cartridge decoupled from the shaft assembly.
Figure 43:
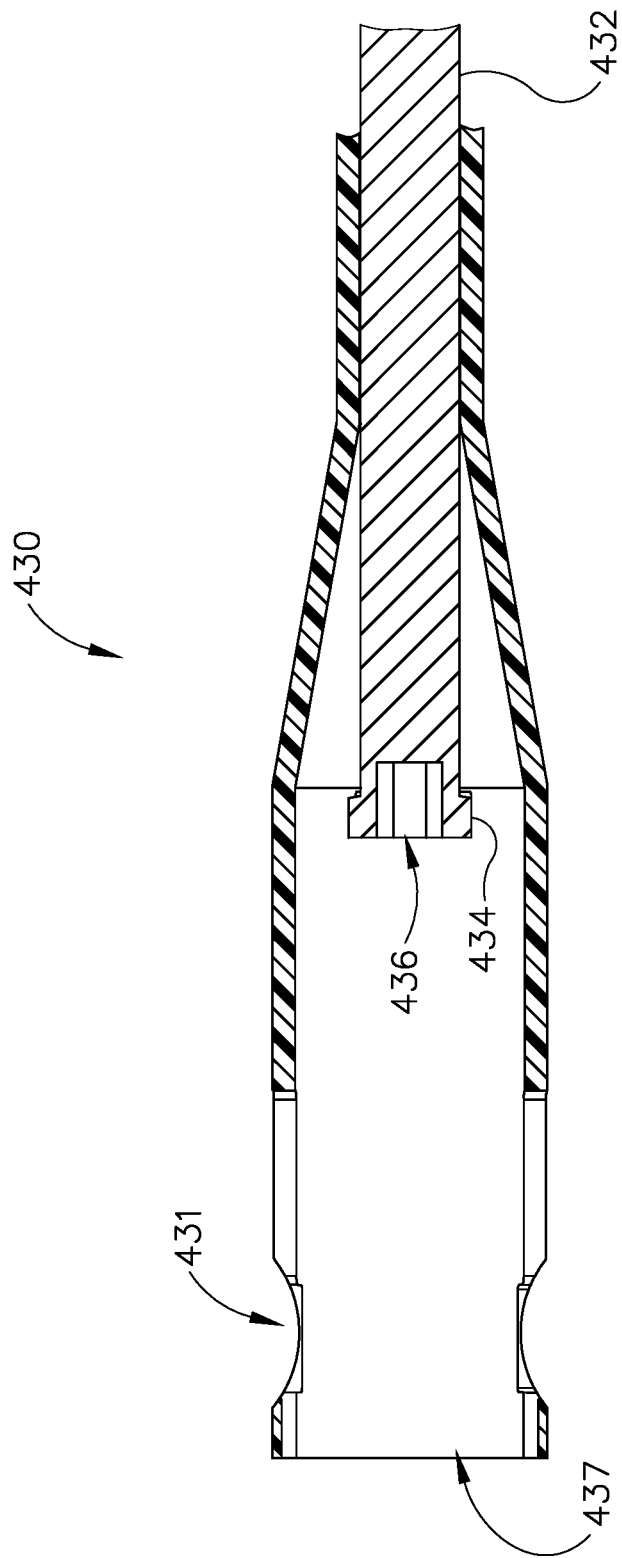
FIG. 43 depicts a cross-sectional view of the distal end of the shaft assembly of the surgical instrument of FIG. 33.

In some instances, it may be desirable to permit removal of at least part of stapling head assembly (440) from the rest of stapling instrument (400). FIGS. 42A-43 show exemplary features that are incorporated into stapling head assembly (440) and shaft assembly (430) of the present example to enable removal of stapling head assembly (440) from shaft assembly (430). In particular, FIGS. 42A-43 show stapling head assembly (440) being provided in a cartridge housing (600) that is removable from the distal end of shaft assembly (430). Cartridge housing (600) includes a first locking features, such as a pair of outwardly extending tabs (602) that are positioned at the free ends of respective resilient arms (604). The distal end of shaft assembly (430) presents a socket (437) that receives cartridge housing (600). Socket (437) includes a pair of lateral openings (431) that correspond with tabs (602) of cartridge housing (602). In particular, resilient arms (604) are configured to resiliently bias tabs (602) into openings (431) when cartridge housing (600) is fully seated in socket (437), thereby locking cartridge housing (600) in place relative to shaft assembly (430). As best shown in FIG. 43, the distal end of drive shaft (432) is positioned within socket (437), such that the distal end of drive shaft (432) will enter bore (452) of first rotary drive element (450) when cartridge housing (600) is fully seated in socket (437).

In order to remove cartridge housing (600) from socket (437), and thereby decouple stapling head assembly (440) from shaft assembly (430), a user may depress both tabs (602) inwardly to decouple tabs (602) from openings (431). While holding tabs (602) in these depressed positions, the user may then pull cartridge housing (600) distally away from shaft assembly (430) as shown in the transition from FIG. 42A to FIG. 42B. At some point thereafter, another cartridge housing (600) may be inserted into socket (437). In some instances, this may be performed during a single surgical procedure. For instance, if the operator made a mistake during an initial attempt at securing an anastomosis and failed to properly deploy staples from stapling head assembly (440), the operator may withdraw stapling head assembly from the surgical site and re-load shaft assembly (430) with another stapling head assembly (440) to try completing the anastomosis again with the same stapling instrument (400). The operator would thus avoid the need to dispose of the entire stapling instrument (400) and use a completely new stapling instrument (400).

As another merely illustrative example, stapling instrument (400) may be provided as a partially reusable device. For instance, after being used in a surgical procedure, a nurse or other personnel may remove stapling head assembly (440) from shaft assembly (430) and dispose of the used stapling head assembly (440). The rest of stapling instrument (400) may then be sent to a sterilization process or other reclamation process. In instances where stapling instrument (400) includes a power source (420), motor (422), and/or other electronic components, such components may be removed for separate processing while the remainder of shaft assembly (430) and handle assembly (410) are sterilized in any suitable fashion. After processing, the previously used shaft assembly (430) and handle assembly (410) may be combined with a new stapling head assembly (440) for use in another surgical procedure. Various other suitable ways in which components of stapling instrument (400) may be handle before, during, and after surgical procedures will be apparent to those of ordinary skill in the art in view of the teachings herein.

Of course, the modular cartridge configuration of stapling head assembly (440) in the present example is merely optional. Other suitable ways in which at least part of stapling head assembly (440) may be provided in a cartridge or modular form will be apparent to those of ordinary skill in the art in view of the teachings herein. It should also be understood that some versions of stapling head assembly (440) may simply be unitary with shaft assembly (430), such that stapling head assembly (440) may not be removed from shaft assembly (430). By way of example only, some such versions of stapling instrument (400) may be configured for a single use only, such that the entire stapling instrument (400), including stapling head assembly (440), is disposed of after a single use. Other suitable variations will be apparent to those of ordinary skill in the art in view of the teachings herein.

Similarly, at least some of the teachings herein may be readily combined with one or more teachings of U.S. patent application Ser. No. 13/716,323, entitled "Motor Driven Rotary Input Circular Stapler with Lockable Flexible Shaft," filed on Dec. 17, 2012 and issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," issued Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A powered circular stapling device, comprising:
    (a) a handle assembly comprising:
        (i) a housing,
        (ii) a motor disposed within the housing,
        (iii) a battery configured to energize the motor, and
        (iv) a manual rotatable body rotatably coupled with the housing;
    (b) a shaft assembly comprising a proximal portion and a distal portion, wherein the proximal portion of the shaft assembly is associated with the handle assembly;
    (c) a removable cartridge configured to selectively attach to the distal portion of the shaft assembly, wherein the removable cartridge comprises:
        (i) a trocar configured to translate between a proximal trocar position and a distal trocar position when the removable cartridge is attached to the distal portion of the shaft assembly, and
        (ii) a stapling assembly configured to translate between an unactuated position and an actuated position when the removable cartridge is attached to the distal portion of the shaft assembly; and
    (d) a clutch assembly configured to transition between a power actuation mode and a manual actuation mode, wherein the motor is configured to translate the trocar in the power actuation mode, wherein the manual rotatable body is configured to translate the trocar in the manual actuation mode.

2. The powered circular stapling device of claim 1, wherein the shaft assembly comprises a rotary drive actuator configured to rotate to thereby drive translation of the trocar.

3. The powered circular stapling device of claim 2, wherein the clutch assembly comprises a first gear fixed relative to the manual rotating body and a second gear rotatably disposed and longitudinally fixed within the housing.

4. The powered circular stapling device of claim 3, wherein the second gear defines a distally presented opening, wherein the rotary drive is deposed within the distally presented opening such that rotation of the second gear drives rotation of the rotary drive.

5. The powered circular stapling device of claim 4, wherein the second gear comprises a motor coupling feature and a first gear coupling feature, wherein the second gear is configured to couple the rotary drive with the motor via the motor coupling feature in the power actuation mode, wherein the second gear is configured to couple the rotary drive with the manual rotating body via the first gear coupling feature in the manual actuation mode.

6. The powered circular stapling device of claim 5, wherein the motor coupling feature comprises a proximally presented opening configured to receive a drive shaft of the motor.

7. The powered circular stapling device of claim 6, wherein the first gear coupling feature comprises a plurality of spines configured to mesh with the first gear.

8. The powered circular stapling device of claim 2, wherein the rotary drive actuator is configured to rotate to thereby drive actuation of the stapling assembly.

9. The powered circular stapling device of claim 8, wherein the rotary drive actuator is configured to translate between a staple drive position and a trocar drive position.

10. The powered circular stapling drive of claim 9, further comprising a firing ring configured to actuate relative to the housing in order to translate the rotary drive actuator between the staple drive position and the trocar drive position.

11. The powered circular stapling device of claim 1, wherein the clutch assembly is biased toward the powered actuation mode.

12. The powered circular stapling device of claim 1, wherein the manual rotating body comprises a plurality of splines configured to engage the housing when the clutch assembly is in the powered actuation mode.

13. The powered circular stapling device of claim 1, wherein the clutch assembly is configured to decouple the battery from the motor in the manual actuation mode.

14. The powered circular stapling device of claim 1, further comprising a motor housing rotatably disposed within the housing.

15. The powered circular stapling device of claim 14, wherein the motor housing is fixed to the manual rotatably body.

16. A powered circular stapling device, comprising:
    (a) a handle assembly comprising:
        (i) a housing,
        (ii) a motor disposed within the housing, and
        (iii) a manual rotatable body rotatably coupled with the housing;
    (b) a shaft assembly comprising a proximal portion and a distal portion, wherein the proximal portion of the shaft assembly is associated with the handle assembly;

(c) a removable cartridge configured to selectively attach to the distal portion of the shaft assembly, wherein the removable cartridge comprises a trocar configured to translate between a proximal trocar position and a distal trocar position when the removable cartridge is attached to the distal portion of the shaft assembly; and (d) a clutch assembly configured to transition between a power actuation mode and a manual actuation mode, wherein the motor is configured to translate the trocar in the power actuation mode, wherein the manual rotatable body is configured to translate the trocar in the manual actuation mode.

17. The powered circular stapling device of claim 16, wherein the shaft assembly comprises a rotatable drive shaft configured to rotate in order to translate the trocar.

18. The powered circular stapling device of claim 17, wherein the motor is configured to rotate the rotatably drive shaft in the power actuation mode, wherein the manual rotatable body is configured to rotate the rotatable drive shaft in the manual actuation mode.

19. A powered circular stapling device, comprising:
(a) a handle assembly comprising:
 (i) a housing,
 (ii) a motor disposed within the housing, and
 (iii) a manual rotatable body rotatably coupled with the housing;
(b) a shaft assembly comprising a proximal portion and a distal portion, wherein the proximal portion of the shaft assembly is associated with the handle assembly, wherein the shaft assembly comprises a rotating drive shaft;
(c) a removable cartridge configured to selectively attach to the distal portion of the shaft assembly, wherein the removable cartridge comprises a trocar configured to translate between a proximal trocar position and a distal trocar position when the removable cartridge is attached to the distal portion of the shaft assembly, wherein the rotating drive is configured to translate the trocar when the removable cartridge is attached to the distal portion of the shaft assembly; and
(d) a clutch assembly configured to transition between a power actuation mode and a manual actuation mode, wherein the motor is configured to translate the trocar in the power actuation mode, wherein the manual rotatable body is configured to translate the trocar in the manual actuation mode.

20. The powered circular stapler of claim 19, wherein the clutch assembly is biased toward the power actuation mode.

* * * * *